US009061966B2

(12) United States Patent
Laria et al.

(10) Patent No.: US 9,061,966 B2
(45) Date of Patent: Jun. 23, 2015

(54) CYCLOPROPYLAMINE INHIBITORS OF OXIDASES

(75) Inventors: Julio Castro-Palomino Laria, Premià de Mar (ES); Matthew Colin Thor Fyfe, Chipping Norton (GB); Marc Martinell Pedemonte, Barcelona (ES); Alberto Ortega Muñoz, Barcelona (ES); Núrla Valls Vidal, Barcelona (ES)

(73) Assignee: ORYZON GENOMICS S.A., Cornella de Llobregat, Barcelona (ES)

( * ) Notice: Subject to any disclaimer, the term of this patent is extended or adjusted under 35 U.S.C. 154(b) by 0 days.

(21) Appl. No.: 13/877,919

(22) PCT Filed: Oct. 7, 2011

(86) PCT No.: PCT/EP2011/067608
§ 371 (c)(1),
(2), (4) Date: Jul. 15, 2013

(87) PCT Pub. No.: WO2012/045883
PCT Pub. Date: Apr. 12, 2012

(65) Prior Publication Data
US 2013/0289076 A1    Oct. 31, 2013

(30) Foreign Application Priority Data
Oct. 8, 2010  (EP) ..................... 10187039

(51) Int. Cl.
| C07D 401/12 | (2006.01) |
| C07D 213/74 | (2006.01) |
| A61K 31/136 | (2006.01) |
| C07C 211/52 | (2006.01) |
| C07C 211/53 | (2006.01) |
| C07C 211/55 | (2006.01) |
| C07C 211/56 | (2006.01) |
| C07C 217/92 | (2006.01) |
| C07C 237/30 | (2006.01) |
| C07C 255/58 | (2006.01) |

(52) U.S. Cl.
CPC .............. *C07C 211/52* (2013.01); *C07C 211/53* (2013.01); *C07C 211/55* (2013.01); *C07C 211/56* (2013.01); *C07C 217/92* (2013.01); *C07C 237/30* (2013.01); *C07C 255/58* (2013.01); *C07D 213/74* (2013.01); *C07D 401/12* (2013.01)

(58) Field of Classification Search
USPC .......................................... 514/357; 546/329
See application file for complete search history.

(56) References Cited

U.S. PATENT DOCUMENTS

| 3,106,578 | A | 10/1963 | Kaiser et al. |
| 3,365,458 | A | 1/1968 | Biel et al. |
| 3,471,522 | A | 10/1969 | Biel et al. |
| 3,532,712 | A | 10/1970 | Biel et al. |
| 3,532,749 | A | 10/1970 | Biel et al. |
| 3,758,684 | A | 9/1973 | Elion et al. |
| 4,409,243 | A | 10/1983 | Lieb |
| 4,522,811 | A | 6/1985 | Eppstein et al. |
| 4,530,901 | A | 7/1985 | Weissmann |
| 6,043,393 | A | 3/2000 | de Meijere et al. |
| 6,211,244 | B1 | 4/2001 | Van Wagenen et al. |
| 6,337,074 | B1 | 1/2002 | Marsden et al. |
| 6,809,120 | B1 | 10/2004 | Warrington et al. |
| 7,399,825 | B2 | 7/2008 | Lipps et al. |
| 7,611,704 | B2 | 11/2009 | Thorpe et al. |
| 7,628,993 | B2 | 12/2009 | Vilalta et al. |
| 7,799,782 | B2 | 9/2010 | Munson et al. |
| 8,524,717 | B2 | 9/2013 | Guibourt et al. |
| 8,722,743 | B2 | 5/2014 | Ortega-Munoz et al. |
| 2003/0008844 | A1 | 1/2003 | Spero et al. |
| 2003/0236225 | A1 | 12/2003 | Protopopova et al. |
| 2004/0019117 | A1 | 1/2004 | Protopopova et al. |
| 2004/0033986 | A1 | 2/2004 | Protopopova et al. |
| 2004/0048802 | A1 | 3/2004 | Ripka et al. |
| 2004/0132820 | A1 | 7/2004 | Gosselin et al. |
| 2004/0147741 | A1 | 7/2004 | Sundermann et al. |

(Continued)

FOREIGN PATENT DOCUMENTS

| EP | 1193268 | 4/2002 |
| EP | 1704859 | 9/2006 |

(Continued)

OTHER PUBLICATIONS

Dorwald; "Side Reactions in Organic Synthesis: A Guide to Successful Synthesis Design" 2005 Wiley-VCH Verlag GmbH & Co. KGaA, Wienheim, Chapter 1.*
S. Mimasu et al, "Structurally designed trans-2-phenylcyclopropylamine derivatives potently inhibit histone demethylase LSD1/KDM1", Biochemistry, 2010, 49(30): 6494-6503.
International Search Report of PCT/EP2011/067608, Mar. 15, 2012.
International Preliminary Report on Patentability of PCT/EP2011/067608, Apr. 9, 2013.
Ahmed et al, "Ticagrelor: a new reversible oral antiplatelet agent" Int Research Journal of Pharmacy, 2010, 1(1), 62-69.
Arya et al, "Synthesis of 5H-dibenzo[a,d]cycloheptene derivatives with diverse biological activities", Indian J Chemistry B, 1978, 16B,220-225.

(Continued)

Primary Examiner — John Mabry
Assistant Examiner — Daniel Carcanague
(74) Attorney, Agent, or Firm — Finnegan, Henderson, Farabow, Garrett & Dunner

(57) ABSTRACT

The invention relates to cyclopropylamine compounds, in particular the compounds of Formula (I) as described and defined herein, and their use in therapy, including, e.g., the treatment or prevention of cancer.

(I)

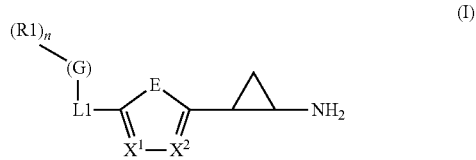

22 Claims, No Drawings

(56) References Cited

U.S. PATENT DOCUMENTS

| | | | |
|---|---|---|---|
| 2004/0162287 | A1 | 8/2004 | Sundermann et al. |
| 2004/0176469 | A1 | 9/2004 | Thomas |
| 2004/0229872 | A1 | 11/2004 | Friderichs et al. |
| 2004/0254158 | A1 | 12/2004 | Qiao et al. |
| 2005/0009832 | A1 | 1/2005 | Sun et al. |
| 2005/0154056 | A1 | 7/2005 | Yang et al. |
| 2006/0116370 | A1 | 6/2006 | Dollinger et al. |
| 2006/0148904 | A1 | 7/2006 | Protopopova et al. |
| 2006/0211709 | A1 | 9/2006 | Buhr et al. |
| 2006/0270673 | A1 | 11/2006 | Duggan et al. |
| 2006/0275366 | A1 | 12/2006 | Malcom et al. |
| 2006/0287287 | A1 | 12/2006 | Gerritz et al. |
| 2007/0213338 | A1 | 9/2007 | Lebsack et al. |
| 2008/0139665 | A1 | 6/2008 | Schuele et al. |
| 2008/0242698 | A1 | 10/2008 | Flor et al. |
| 2008/0269228 | A1 | 10/2008 | Moore et al. |
| 2009/0203750 | A1 | 8/2009 | Kozikowski et al. |
| 2009/0247530 | A1 | 10/2009 | Nolte et al. |
| 2010/0016262 | A1 | 1/2010 | Mehal et al. |
| 2010/0240649 | A1 | 9/2010 | Zhang |
| 2010/0292225 | A1 | 11/2010 | Chamoin et al. |
| 2010/0324147 | A1* | 12/2010 | McCafferty et al. .......... 514/647 |
| 2012/0202810 | A1 | 8/2012 | Nolte et al. |
| 2013/0197095 | A1 | 8/2013 | Nolte et al. |

FOREIGN PATENT DOCUMENTS

| | | |
|---|---|---|
| EP | 1741708 | 1/2007 |
| EP | 2233495 | 9/2010 |
| GB | 1307341 | 2/1973 |
| JP | 2001354563 | 12/2001 |
| SU | 230169 | 10/1968 |
| WO | WO94/27947 | 12/1994 |
| WO | WO96/38141 | 12/1996 |
| WO | WO98/18459 | 5/1998 |
| WO | WO99/05142 | 2/1999 |
| WO | WO99/05143 | 2/1999 |
| WO | WO99/31072 | 6/1999 |
| WO | WO99/54440 | 10/1999 |
| WO | WO99/67203 | 12/1999 |
| WO | WO00/34283 | 6/2000 |
| WO | WO01/92264 | 12/2001 |
| WO | WO02/079152 | 10/2002 |
| WO | WO03/087064 | 10/2003 |
| WO | WO03/093297 | 11/2003 |
| WO | WO03/096989 | 11/2003 |
| WO | WO2004/020415 | 3/2004 |
| WO | WO2004/055010 | 7/2004 |
| WO | WO2004/062601 | 7/2004 |
| WO | WO2004/065367 | 8/2004 |
| WO | WO2004/072086 | 8/2004 |
| WO | WO2005/009941 | 2/2005 |
| WO | WO2005/023761 | 3/2005 |
| WO | WO2005/025558 | 3/2005 |
| WO | WO2005/037843 | 4/2005 |
| WO | WO2005/058808 | 6/2005 |
| WO | WO2005/058883 | 6/2005 |
| WO | WO2005/058884 | 6/2005 |
| WO | WO2005/103003 | 11/2005 |
| WO | WO2006/071608 | 7/2006 |
| WO | WO2006/087206 | 8/2006 |
| WO | WO2007/000248 | 1/2007 |
| WO | WO2007/005896 | 1/2007 |
| WO | WO2007/015824 | 2/2007 |
| WO | WO2007/025144 | 3/2007 |
| WO | WO2007/025709 | 3/2007 |
| WO | WO2007/021839 | 7/2007 |
| WO | WO2007/106016 | 9/2007 |
| WO | WO2007/134799 | 11/2007 |
| WO | WO2008/033466 | 3/2008 |
| WO | WO2008/116156 | 9/2008 |
| WO | WO2008/127734 | 10/2008 |
| WO | WO2009/001132 | 12/2008 |
| WO | WO2009/023179 | 2/2009 |
| WO | WO2009/039134 | 3/2009 |
| WO | WO2009/052078 | 4/2009 |
| WO | WO2009/097278 | 8/2009 |
| WO | WO2009/109991 | 9/2009 |
| WO | WO2009/117515 | 9/2009 |
| WO | WO2009/145856 | 12/2009 |
| WO | WO2009/153197 | 12/2009 |
| WO | WO2010/011845 | 1/2010 |
| WO | WO2010/014921 | 2/2010 |
| WO | WO2010/030592 | 3/2010 |
| WO | WO2010/043721 A1 | 4/2010 |
| WO | WO2010/084160 | 7/2010 |
| WO | WO2010/085749 | 7/2010 |
| WO | WO2010/099527 | 9/2010 |
| WO | WO2010/139784 | 12/2010 |
| WO | WO2010/143582 | 12/2010 |
| WO | WO2011/022489 | 2/2011 |
| WO | WO2011/031934 | 3/2011 |
| WO | WO 2011035941 * | 3/2011 |
| WO | WO 2011042217 * | 4/2011 |
| WO | WO2011/057262 | 5/2011 |
| WO | WO2011/106105 | 9/2011 |
| WO | WO2011/106106 | 9/2011 |
| WO | WO2011/113005 | 9/2011 |
| WO | WO2011/131576 | 10/2011 |
| WO | WO2011/131697 | 10/2011 |
| WO | WO2011/132083 | 10/2011 |
| WO | WO2012/001531 | 1/2012 |
| WO | WO2012/013727 | 2/2012 |
| WO | WO2012/013728 | 2/2012 |
| WO | WO2012/034116 | 3/2012 |
| WO | WO2012/045883 | 4/2012 |
| WO | WO 2012042042 * | 4/2012 |
| WO | WO2012/072713 | 6/2012 |
| WO | WO2012/107498 | 8/2012 |
| WO | WO2012/107499 | 8/2012 |
| WO | WO2012/135113 | 10/2012 |
| WO | WO2012/156531 | 11/2012 |
| WO | WO2012/156537 | 11/2012 |
| WO | WO2013/057320 | 4/2013 |
| WO | WO2013/057322 | 4/2013 |

OTHER PUBLICATIONS

Bar-am et al, "Regulation of Bcl-2 family proteins, neurotrophic factors, and APP processing in the neurorescue activity of propargylamine". FASEB J, 2005, 19(13), 1899-1901.

Barlesi et al, "Global histone modifications predict prognosis of resected non small-cell lung cancer",J Clin Oncol,2007,25, 4358-4364.

Benelkebir et al, "Enantioselective synthesis of tranylcypromine analogues as lysine demethylase (LSD1) inhibitors", Bioorg Med Chem, 2011, 19(12),3709-3716.

Biljak et al,"Platelet count, mean platelet volume and smoking status in stable chronic obstructive pulmonary disease", Platelets, 2011,22(6), 466-70.

Binda et al, "Biochemical, structural, and biological evaluation of tranylcypromine derivatives as inhibitors of histone demethylases LSD1 and LSD2", J Am Chem Soc,2010, 132(19),6827-6833.

Bisi et al, "Multidrug resistance reverting activity and antitumor profile of new phenothiazine derivatives", Bioorg Med Chem, 2008, 16(13), 6474-6482.

Boilard et al, "Platelets amplify inflammation in arthritis via collagen-dependent microparticle production", Science, 2010,327(5965), 580-583.

Bolesov et al, "Cyclopropanes and cyclobutanes LXIX", Zhurnal Organicheskoi Khimii (English Translation), 1974, 10(10), 2122-2128.

Bolesov et al, "Cyclopropanes and cyclobutanes LXVIII. N-mono and N,N-disubstituted 1-amino-2-phenylcyclopropanes",Zhurnal Organicheskoi Khimii (English Translation), 1974, 10(6), 1678-84.

Brand and Perrimon, "Targeted gene expression as a means of altering cell fates and generating dominant phenotypes", 1993, Development, 118, 401-415.

Brydon et al, "Platelets, coronary heart disease and stress", Brain, Behavior and Immunity,2006,20(2), 113-119.

(56) References Cited

OTHER PUBLICATIONS

Burakova et al, "N- and O-alkylation of 3-indolylcyclopropylacetic acid derivatives", Russian Chemical Bulletin, 2002, 51(10) 1829-1840.

Burk et al, "Cognitive deficits in spinocerebellar ataxia 2", Brain, 1999, 122(4), 769-777.

Cakmak et al, "Platelets: indicator of inflammation in COPD", Int J Med Med Sci, 2009, 1(5), 227-229.

Calogero et al, "Inhibition of cell growth by EGR-1 in human primary cultures from malignant glioma",Cancer Cell International,2004,4, 1.

Casero et al, "Recent advances in the development of polyamine analogues as antitumor agents", J Med Chem, 2009, 52(15),4551-4573.

Chen et al, "Association of insulin resistance and hematologic parameters: study of a middle-aged and elderly chinese population in Taiwan", J Chin Med Assoc,2006, 69(6), 248-253.

Chimenti et al "Synthesis, Stereochemical Identification, and Selective Inhibitory Activity against Human Monoamine Oxidase-B of 2-Methylcyclohexylidene-(4-arylthiazol-2-yl)hydrazones". (2008) J. Med. Chem. 51 (16), 4874-4880.

Choi et al "Histone demethylase LSD1 is required to induce skeletal muscle differentiation by regulating myogenic factors" (2010) Biochemical and Biophysical Research Communications 401(3), 327-332.

Choo et al, "Genetic organization and diversity of the hepatitis C virus", Proc Natl Acad Sci,1991, 88,2451-2455.

Culhane et al, A mechanism-based inactivator for histone demethylase LSD1, J Am Chem Soc, 2006, 128(14), 4536-4537.

Culhane et al, "Comparative analysis of small molecules and histone substrate analogues as LSD1 lysine demethylase inhibitors", J Am Chem Soc, 2010,132(9),3164-3176.

Danese et al, "Platelets in inflammatory bowel disease: clinical, pathogenic and therapeutic implications", Am J Gastroenterol, 2004,99(5), 938-45.

Di Stefano et al, Mutation of *Drosophila* Lsd1 disrupts H3—K4 methylation, resulting in tissue-specific defects during development, Curr Biol,2007, 17(9), 808-12.

East et al, "An orally bioavailable positive allosteric modulator of the mGlu4 receptor with efficacy in an animal model of motor dysfunction", Bioorg Med Chem Lett, 2010, 20(16), 4901-5.

Ellis et al, "Expression of *Drosophila* glass protein and evidence for negative regulation of its activity in non-neuronal cells by another DNA-binding protein",Development,1993, 119, 855-865.

Elsheikh et al "Global histone modifications in breast cancer correlate with tumor phenotypes, prognostic factors and patient outcome", Canc Res, 2009,69, 3802-3809.

Erazo et al, "Varicella-zoster virus open reading frame 66 protein kinase is required for efficient viral growth in primary human corneal stromal fibroblast cells", J Virol, 2008,82, 7653-7665.

Faler et al, "The Kulinkovich reaction in the synthesis of constrained N,N-dialkyl neurotransmitter analogues", Organic Letters 2007,9(10),1987-1990.

Ferlay et al, "Estimates of the cancer incidence and mortality in Europe in 2006", Annals of Oncology 2007,18(3), 581-92.

Ferraro et al. "EGR1 predicts PTEN and survival in patients with non-small-cell lung cancer", J Clin Oncol, 2005, 23(9), 1921-26.

Fischer et al, "Recovery of learning and memory is associated with chromatin remodelling", Nature, 2007,447, 178-182.

Forneris et al "LSD1: oxidative chemistry for multifaceted functions in chromatin Regulation." Trends in Biochemical Sciences 2008,33(4), 181-189.

Gawaz et al, "Platelets in inflammation and atherogenesis", J Clin Invest, 2005,115(12), 3378-3384.

Gooden et al, "Facile synthesis of substituted trans-2-arylcyclopropylamine inhibitors of the human historic demethylase LSD1 and monoamine oxidases A and B", Bioorg Med Chem Lett 2008, 18(10), 3047-51.

Han et al "Modulation of breast cancer resistance protein (BCRP/ABCG2) by non-basic chalcone analogues" Eur. J. Pharma. 2008, 35(1-2) 30-41.

Han et al, "Antidepressants reveal differential effect against 1-methyl-4-phenylpyridinium toxicity in differentiated PC12 cells", Eur J Pharmacol, 2009, 604 (1-3),36-44.

Hayami et al, "Overexpression of LSD1 contributes to human carcinogenesis through chromatin regulation in various cancers", Int J Cancer, 2011, 128(3), 574-86.

Hruschka et al, "Fluorinated phenylcyclopropylamines. Part 5:Effect of electron-withdrawing or -donating aryl substituents on the inhibition of monoamine oxidases A and B by 2-aryl-2-fluoro-cyclopropylamines", Bioorg Med Chem,2008, 16(15), 7148-7166.

Huang et al, "Novel oligoamine analogues inhibit lysine-specific demethylase 1 (LSD1) and induce re-expression of epigeneticall silenced genes",Clin Cancer Res,2009, 15(23), 7217-28.

Huang et al, "p53 is regulated by the lysine demethylase LSD1",Nature,2007,449, 105-108.

Huang et al,"Inhibition of lysine-specific demethylase 1 by polyamine analogues results in reexpression of aberrantly silenced genes", PNAS,2007, 104(19), 8023-8028.

Jackson et al, "Polyglutamine-expanded human Huntingtin transgenes induce degeneration of *Drosophila* photoreceptor neurons", Neuron, 1998, 21, 633-642.

Kahl et al,"Androgen receptor coactivators lysine-specific histone demethylase 1 and four and a half LIM domain protein 2 predict risk of prostate cancer recurrence", Cancer Res,2006,66 (23), 11341-11347.

Kaiser et al, "2-substituted cyclopropylamines. I. Derivatives and analogs of 2-phenylcyclopropylamine", J Med Pharm Chem (ACS), 1962, 5, 1243-1265.

Kiefmann et al, "Red blood cells induce hypoxic lung inflammation", Blood, 2008, 111(10),5205-14.

Kim et al, "Flavin chemical models for monoamine oxidase inactivation by cyclopropylamines, α-silylamines, and hydrazines", J Am Chem Soc 1995, 117, 100-105.

Kinzel et al, "Identification of MK-5710 ((8aS)-8a-methyl-1,3-dioxo-2-[(1S,2R)-2-phenylcyclopropyl]-N-(1-phenyl-1H-pyrazol-5-yl)hexahydro-imidazo[1,5-a]pyrazine-7-(1H)-carboxamide), a potent smoothened antagonist for use in Hedgehog pathway dependent malignancies. Part 2", Bioorg Med Chem Lett 2011, 21(15), 4429-4435.

Kornerup et al, "The role of platelets in the pathophysiology of asthma" Platelets, 2007, 18(5), 319-28.

Krieger et al, "Enhancement of hepatitis C virus RNA replication by cell culture-adaptive mutations", J Virol, 2001,75, 4614-4624.

Lan et al "Mechanisms involved in the regulation of histone lysine demethylases". Current Opinion in Cell Biology, 2008,20, 316-325.

Lee et al, "Combinatorial lead optimization of [1,2]-diamines based on ethambutol as potential antituberculosis preclinical candidates", J Comb Chem, 2003, 5(2), 172-187.

Lee et al, "Histone H3 lysine 4 demethylation is a target of nonselective antidepressive medications",Chem Biol, 2006,13(6), 563-567.

Li et al, "Association between inflammatory mediators and angiographic morphologic features indicating thrombus formation in patients with acute myocardial infarction", Chin Med J, 2009,122(15), 1738-42.

Liang at al, "Inhibition of the histone demethylase LSD1 blocks alpha-herpesvirus lytic replication and reactivation from latency",Nat Med, 2009,15 (11), 1312-1317.

Lim et al, "Lysine-specific demethylase 1 (LSD1) is highly expressed in ER-negative breast cancers and a biomarker predicting aggressive biology", Carcinogenesis,2010, 31(3), 512-20.

Lucerna at al, "Sustained expression of early growth response protein-1 blocks angiogenesis and tumor growth",Cancer Research,2006, 66,6708-6713.

Lupu Roxana, "Up-to-date in the hematological malignancies treatment", Maedica, 2006,1(1), 63-65.

Maclay et al, "Increased platelet activation in patients with stable and acute exacerbation of COPD", Thorax, 2011,66(9), 769-74.

(56) References Cited

OTHER PUBLICATIONS

Mannaioni et al, "Platelets and inflammation: role of platelet-derived growth factor, adhesion molecules and histamine", Inflamm Res, 1997,46(1), 4-18.

McNicol et al, "Beyond hemostasis: the role of platelets in inflammation, malignancy and infection",Cardiovascular & Haematological Disorders—Drug Targets, 2008,8, 99-117.

Meanwell, "Synopsis of some recent tactical application of bioisosteres in drug design", J Med Chem, 2011, 54(8),2529-91.

Metzger et al, "LSD1 demethylates repressive histone marks to promote androgen-receptor-dependent transcription",Nature,2005, 437(7057),436-9.

Mimasu et al "Crystal structure of histone demethylase LSD1 and tranylcypromine at 2.25 A" Biochemical and Biophysical Research Communications ,2008,366, 15-22.

Moritani et al, "Activation of platelets in bronchial asthma", Chest, 1998,113, 452-458.

Nabil Aboul-Enein et al, "Synthesis of some 4-substituted amino-1-methylpiperidines structurally related to antihistaminics", Pharmaceutica Acta Helvetiae, 1973, 48(3): 151-156.

Neelamegan et al, "Brain-penetrant LSD1 inhibitors can block memory consolidation", ACS Chem Neurosci, 2012, 3(2), 120-128.

Ogasawara et al, "Synthesis and biological activity of optically active NCL-1, a lysine-specific demethylase 1 selective inhibitor",Bioorg Med Chem, 2011, doi:10.1016/j.bmc.2010.12.024.

O'Sullivan et al, "The inflammatory role of platelets in cystic fibrosis", Am J Respir Crit Care Med, 2006,173, 483-90.

Pannala et al "Synthesis and structure—activity relationship of 4-(2-aryl-cyclopropylamino)-quinoline-3-carbonitriles as EGFR tyrosine kinase inhibitors". Bioorg & Med Chem Lett ,2017,17 (21), 5978-5082.

Pitchford et al, "Platelet P-selectin is required for pulmonary eosinophil and lymphocyte recruitment in a murine model of allergic inflammation", Blood, 2005,105, 2074-2081.

Pollock et al, Lysine-specific histone demethylase 1 inhibitors control breast cancer proliferation in ERalpha-dependent and -independent manners, ACS Chem Biol 2012,7,1221-1231.

Ravina et al, "The relationship between CAG repeat length and clinical progression in Huntington's disease", Movement Disorders,2008,23(9), 1223-7.

Reddy et al, "Role of lysine-specific demethylase 1 in the proinflammatory phenotype of vascular smooth muscle cells of diabetic mice",Circ Res,2008,103, 615-23.

Riley et al, "Absolute configuration of (+)- and (-)-trans-2-phenylcyclopropylamine hydrochloride",J Med Chem, 1972,15(11), 1187-1188.

Rinder et al, "Correlation of thrombosis with increased platelet turnover in thrombocytosis", Blood, 1998,91(4), 1288-1294.

Schmidt et al,"trans-2-phenylcyclopropylamine is a mechanism-based inactivator of the histone demethylase LSD1", Biochemistry, 2007,46(14),4408-4416.

Schulte et al, "Lysine-specific demethylase 1 is strongly expressed in poorly differentiated neuroblastoma: implications for therapy", Cancer Res,2009,69(5),2065-71.

Scoumanne et al "Protein methylation: a new mechanism of p53 tumor suppressor regulation" Histol Histopathol 2008,23, 1143-1149.

Scoumanne et al, "The lysine-specific demethylase 1 is required for cell proliferation in both p53-dependent and -independent manners", J Biol Chem, 2007,282(21), 15471-5.

Seligson et al, "Global histone modification patterns predict risk of prostate cancer recurrence",Nature, 2005,435, 1262-1266.

Seligson et al,"Global levels of histone modifications predict prognosis in different cancers" ,Am J Path, 2009,174,1619-28.

Sharma et al, "(Bis)urea and (bis)thiourea inhibitors of lysine-specific demethylase 1 as epigenetic modulators", J Med Chem, 2010,53(14), 5197-5212.

Shi et al,"Histone demethylation mediated by the nuclear amine oxidase homolog LSD1", Cell, 2004,119,941-953.

Shi, "Histone lysine demethylases: emerging roles in development, physiology and disease", Nature Reviews Genetics 2007, 8:829-833.

Stephens et al, "The determination of the absolute configurations of chiral molecules using vibrational circular dichroism (VCD) spectroscopy",Chirality, 2008,20(5), 643-663.

Stoffel et al, "Leukocyte count and risk of thrombosis in patients undergoing haematopoietic stem cell transplantation or intensive chemotherapy",Thromb Haemost, 2010,103(6), 1228-32.

Stratmann et al, "Pathobiology and cell interactions of platelets in diabetes", Diabetes & Vascular Disease Research,2005, 2(1), 16-23.

Szewczuk et al, "Mechanistic analysis of a suicide inactivator of histone demethylase LSD1", Biochemistry, 2007,46, 6892-6902.

Tamagawa-Mineoka et al, "Elevated platelet activation in patients with atopic dermatitis and psoriasis: increased plasma levels of beta-thromboglobulin and platelet factor 4", Allergology International,2008, 57, 391-396.

Taylor et al,"Roscovitine,a cyclin-dependent kinase inhibitor, prevents replication of varicella-zoster virus", J Virol, 2004,78, 2853-2862.

Thaulow et al, "Blood platelet count and function are related to total and cardiovascular death in apparently healtht men", Circulation, 1991,84, 613-617.

Ueda et al, "Identification of cell-active lysine specific demethylase 1-selective inhibitors",J Am Chem Soc, 2009,131(48), 17536-17537.

Vagner et al, "Peptidomimetics, a synthetic tool of drug discovery", Current Opinion on Chemical Biology, 2008, 12:292-296.

Wagner et al, "Platelets in inflammation and thrombosis", Arteriosclerosis, Thrombosis and Vascular Biology, 2003,23, 2131-2137.

Wang et al, Novel histone demethylase LSD1 inhibitors selectively target cancer cells with pluripotent stem cell properties, Cancer Research, 2011, 71(23):7238-49.

Wang et al "LSD1 is a Subunit of the NuRD Complex and Targets the Metastasis Programs in Breast Cancer" Cell 2009, 138, 660-672.

Wang et al, "The lysine demethylase LSD1 (KDM1) is required for maintenance of global DNA methylation", Nature Genetics, 2009,41(1), 125-129.

Weinreb et al, "Novel neuroprotective mechanism of action of rasagiline is associated with its propargyl moiety: interaction of Bcl-2 family members with PKC pathway", Ann NY Acad Sci. 2005,1053, 348-55.

Wermuth, "Molecular variations based on isosteric replacements", The Practice of Medicinal Chemistry (2nd edition), Academic Press, London, 2003, pp. 189-214.

Westland et al , "N-substituted derivatives of 2-aminoethanethiol and 2-hydraxinoethanethiol", JMedChem 1968, 11(4),824-829.

Whitlow et al,"Recruitment of the transcriptional coactivator HCF-1 to viral immediate-early promoters during initiation of reactivation from latency of herpes simplex virus type 1", J Virol, 2009,83(18):9591-5.

Willoughby et al, "Platelets and cardiovascular disease",Eur J Cardiovasc Nursing,2002,1, 273-288.

XP002568777 Database chemcats, database accession No. 2088922753, order No. kbsb-0063197, Aurora screening library, Aug. 20, 2009.

Yang et al "Structural Basis for the Inhibition of the LSD1 Histone Demethylase by the Antidepressant trans-2-Phenylcyclopropylamine" Biochemistry 2007,46 (27), 8058-8065.

Yang et al "Structural basis of histone demethylation by LSD1 revealed by suicide inactivation" Nature Structural & Molecular Biology 2007, 14(6), 535-539.

Yoshida et al, "Fluorinated phenylcyclopropylamines. Part 3: inhibition of monoamine oxidase A and B",Bioorg Med Chem,2004,12(10),2645-2652.

Youdim et al, "Bifunctional drug derivatives of MAO-B inhibitor rasagiline and iron chelator VK-28 as a more effective approach to treatment of brain ageing and ageing neurodegenerative diseases", Mechanisms of Ageing and Development, 2005, 126: 317-326.

Zirkle et al, "2-substituted cyclopropylamines. II. Effect of structure upon monoamine oxidase-inhibitory activity as measured in vivo by potentiation of tryptamine convulsions", J Med Pharm Chem (ACS), 1962, 5, 1265-84.

"Definition of Cancer"—MedicineNetcom Medical references for patients, http://www.medterms.com, 2005.

(56) References Cited

OTHER PUBLICATIONS

Johnson et al, CAPLUS, Document No. 157:576967, "Preparation of cyclopropylamines as LSD1 inhibitors in the treatment of cancer", 2012.
Delorme et al, HCAPLUS, Document No. 132:49802, "Preparation of 1-(N-substituted aminomethyl)-4-guanidinomethylcyclohexanes useful in pain management", 1999.
CAS Registry No. RN220351-33-7, entered STN Mar. 11, 1999.
CAS Registry No. RN844655-03-4, entered STN Mar. 9, 2005.
CAS Registry No. RN846596-02-9, entered STN Mar. 22, 2005.
CAS Registry No. RN848204-13-7, entered STN Apr. 11, 2005.
CAS Registry No. RN848732-87-6, entered STN Apr. 19, 2005.
CAS Registry No. RN848742-47-2, entered STN Apr. 19, 2005.
CAS Registry No. RN848753-47-9, entered STN Apr. 19, 2005.
CAS Registry No. RN903487-42-3, entered STN Aug. 23, 2006.
CAS Registry No. RN918305-55-2, entered STN Jan. 24, 2007.
CAS Registry No. RN959071-98-8, entered STN Dec. 20, 2007.
CAS Registry No. RN1026299-47-7, entered STN Jun. 8, 2008.
CAS Registry No. RN1157140-28-7, entered STN Jun. 14, 2009.
CAS Registry No. RN1218057-33-0, entered STN Apr. 11, 2010.
CAS Registry No. RN1247564-27-7, entered STN Oct. 27, 2010.
CAS Registry No. RN1247717-42-5, entered STN Oct. 27, 2010.
CAS Registry No. RN1247999-77-4, entered STN Oct. 28, 2010.
CAS Registry No. RN1248611-33-7, entered STN Oct. 29, 2010.
CAS Registry No. RN1248913-30-5, entered STN Nov. 1, 2010.
CAS Registry No. RN1248971-98-3, entered STN Nov. 1, 2010.
CAS Registry No. RN1250045-89-6, entered STN Nov. 1, 2010.
CAS Registry No. RN1250199-20-2, entered STN Nov. 1, 2010.
CAS Registry No. RN1250332-49-0, entered STN Nov. 1, 2010.
CAS Registry No. RN1251130-23-0, entered STN Nov. 3, 2010.
CAS Registry No. RN1270634-53-1, entered STN Mar. 27, 2011.
CAS Registry No. RN1273738-91-2, entered STN Apr. 3, 2011.
CAS Registry No. RN1274124-27-4, entered STN Apr. 3, 2011.
CAS Registry No. RN1274681-54-7, entered STN Apr. 4, 2011.
CAS Registry No. RN1280568-04-8, entered STN Apr. 15, 2011.
CAS Registry No. RN1280602-35-8, entered STN Apr. 15, 2011.
CAS Registry No. RN1281516-77-5, entered STN Apr. 17, 2011.
CAS Registry No. RN1281556-75-9, entered STN Apr. 17, 2011.
CAS Registry No. RN1281596-19-7, entered STN Apr. 17, 2011.
CAS Registry No. RN1281615-78-8, entered STN Apr. 17, 2011.
CAS Registry No. RN1281856-83-4, entered STN Apr. 18, 2011.
CAS Registry No. RN1281886-96-1, entered STN Apr. 18, 2011.
CAS Registry No. RN1282014-65-6, entered STN Apr. 18, 2011.
CAS Registry No. RN1282165-83-6, entered STN Apr. 19, 2011.
CAS Registry No. RN1282245-50-4, entered STN Apr. 19, 2011.
CAS Registry No. RN1282292-27-6, entered STN Apr. 19, 2011.
CAS Registry No. RN1282425-35-7, entered STN Apr. 19, 2011.
CAS Registry No. RN1282679-60-0, entered STN Apr. 20, 2011.
CAS Registry No. RN1282773-23-2, entered STN Apr. 20, 2011.
CAS Registry No. RN1282804-36-7, entered STN Apr. 20, 2011.
CAS Registry No. RN1282928-27-1, entered STN Apr. 20, 2011.
CAS Registry No. RN1283337-81-4, entered STN Apr. 21, 2011.
CAS Registry No. RN1283356-05-7, entered STN Apr. 21, 2011.
CAS Registry No. RN1283449-65-9, entered STN Apr. 21, 2011.
CAS Registry No. RN1283533-13-0, entered STN Apr. 21, 2011.
CAS Registry No. RN1283662-53-2, entered STN Apr. 21, 2011.
CAS Registry No. RN1283728-98-2, entered STN Apr. 21, 2011.
CAS Registry No. RN1283887-44-4, entered STN Apr. 22, 2011.
CAS Registry No. RN1284036-80-1, entered STN Apr. 22, 2011.
CAS Registry No. RN1284049-14-4, entered STN Apr. 22, 2011.
CAS Registry No. RN1284310-21-9, entered STN Apr. 22, 2011.
CAS Registry No. RN1285070-57-6, entered STN Apr. 24, 2011.
CAS Registry No. RN1285129-34-1, entered STN Apr. 24, 2011.
CAS Registry No. RN1285144-86-6, entered STN Apr. 24, 2011.
CAS Registry No. RN1285176-99-9, entered STN Apr. 24, 2011.
CAS Registry No. RN1285178-46-2, entered STN Apr. 24, 2011.
CAS Registry No. RN1285235-05-3, entered STN Apr. 24, 2011.
CAS Registry No. RN1285348-65-3, entered STN Apr. 25, 2011.
CAS Registry No. RN1285612-69-2, entered STN Apr. 25, 2011.
CAS Registry No. RN1290805-79-6, entered STN May 6, 2011.
CAS Registry No. RN1290906-73-8, entered STN May 6, 2011.
CAS Registry No. RN1290912-35-4, entered STN May 6, 2011.
CAS Registry No. RN1290912-36-5, entered STN May 6, 2011.
CAS Registry No. RN1290949-23-3, entered STN May 6, 2011.
CAS Registry No. RN1290949-24-4, entered STN May 6, 2011.
CAS Registry No. RN1290949-25-5, entered STN May 6, 2011.
CAS Registry No. RN1290971-74-2, entered STN May 6, 2011.
CAS Registry No. RN1290972-32-5, entered STN May 6, 2011.
CAS Registry No. RN1291186-57-6, entered STN May 8, 2011.
CAS Registry No. RN1291186-59-8, entered STN May 8, 2011.
CAS Registry No. RN1291186-62-3, entered STN May 8, 2011.
CAS Registry No. RN1291186-64-5, entered STN May 8, 2011.
CAS Registry No. RN1291230-78-8, entered STN May 8, 2011.
CAS Registry No. RN1291273-81-8, entered STN May 8, 2011.
CAS Registry No. RN1291273-82-9, entered STN May 8, 2011.
CAS Registry No. RN1291273-84-1, entered STN May 8, 2011.
CAS Registry No. RN1291273-86-3, entered STN May 8, 2011.
CAS Registry No. RN1291273-87-4, entered STN May 8, 2011.
CAS Registry No. RN1292446-11-7, entered STN May 10, 2011.
CAS Registry No. RN1304214-87-6, entered STN Jun. 2, 2011.
CAS Registry No. RN1304214-96-7, entered STN Jun. 2, 2011.
CAS Registry No. RN1304214-97-8, entered STN Jun. 2, 2011.
CAS Registry No. RN1304215-06-2, entered STN Jun. 2, 2011.
CAS Registry No. RN1304827-17-5, entered STN Jun. 3, 2011.
CAS Registry No. RN1304845-37-1, entered STN Jun. 3, 2011.
CAS Registry No. RN1304845-55-3, entered STN Jun. 3, 2011.
CAS Registry No. RN1304845-63-3, entered STN Jun. 3, 2011.
CAS Registry No. RN1304845-67-7, entered STN Jun. 3, 2011.
CAS Registry No. RN1304845-70-2, entered STN Jun. 3, 2011.
CAS Registry No. RN1304845-72-4, entered STN Jun. 3, 2011.
CAS Registry No. RN1304845-83-7, entered STN Jun. 3, 2011.
CAS Registry No. RN1305397-75-4, entered STN Jun. 5, 2011.
CAS Registry No. RN1305397-86-7, entered STN Jun. 5, 2011.
CAS Registry No. RN1305398-16-6, entered STN Jun. 5, 2011.
CAS Registry No. RN1306275-88-6, entered STN Jun. 5, 2011.
CAS Registry No. RN1306275-95-5, entered STN Jun. 5, 2011.
CAS Registry No. RN1306276-35-6, entered STN Jun. 5, 2011.
CAS Registry No. RN1306322-57-5, entered STN Jun. 6, 2011.
CAS Registry No. RN1306373-68-1, entered STN Jun. 6, 2011.
CAS Registry No. RN1306589-39-8, entered STN Jun. 6, 2011.
CAS Registry No. RN1307573-60-9, entered STN Jun. 8, 2011.
CAS Registry No. RN1307574-08-8, entered STN Jun. 8, 2011.
Co-pending U.S. Appl. No. 13/138,143, filed Jul. 11, 2011.
Co-pending U.S. Appl. No. 13/497,994, filed Mar. 23, 2012.
Co-pending U.S. Appl. No. 13/500,687, filed Apr. 6, 2012.
Co-pending U.S. Appl. No. 13/580,553, filed Aug. 22, 2012.
Co-pending U.S. Appl. No. 13/580,710, filed Aug. 23, 2012.
Co-pending U.S. Appl. No. 13/812,366, filed Jan. 25, 2013.
Co-pending U.S. Appl. No. 13/812,386, filed Jan. 25, 2013.
Co-pending U.S. Appl. No. 13/876,485, filed Mar. 28, 2013.
Co-pending U.S. Appl. No. 13/983,844, filed Aug. 6, 2013.
Co-pending U.S. Appl. No. 14/118,323, filed Nov. 18, 2013.
Co-pending U.S. Appl. No. 14/118,330, filed Nov. 18, 2013.
Co-pending U.S. Appl. No. 14/096,557, filed Dec. 4, 2013.
Co-pending U.S. Appl. No. 14/184,745, filed Feb. 19, 2014.
Co-pending U.S. Appl. No. 14/228,083, filed Mar. 27, 2014.
Co-pending U.S. Appl. No. 14/352,719, filed Apr. 18, 2014.
Co-pending U.S. Appl. No. 14/352,711, filed Apr. 18, 2014.

\* cited by examiner

CYCLOPROPYLAMINE INHIBITORS OF OXIDASES

The invention relates to cyclopropylamine compounds, in particular the compounds of Formula (I) as described and defined herein, and their use in therapy, including, e.g., the treatment or prevention of cancer.

Aberrant gene expression in affected tissue as compared to normal tissue is a common characteristic of many human diseases. This is true for cancer and many neurological diseases which are characterized by changes in gene expression patterns. Gene expression patterns are controlled at multiple levels in the cell. Control of gene expression can occur through modifications of DNA: DNA promoter methylation is associated with suppression of gene expression. Several inhibitors of DNA methylation are approved for clinical use including the blockbuster Vidaza™. Another class of modifications involve histones which form the protein scaffold that DNA is normally associated with (coiled around) in eukaryotic cells. Histones play a crucial role in organizing DNA and the regulated coiling and uncoiling of DNA around the histones is critical in controlling gene expression—coiled DNA is typically not accessible for gene transcription. A number of histone modification have been discovered including histone acetylation, histone lysine methylation, histone arginine methylation, histone ubiquinylation, and histone sumoylation, many of which modify accessibility to the associated DNA by the cells transcriptional machinery. These histone marks serve to recruit various protein complexes involved in transcription and repression. An increasing number of studies are painting an intricate picture of how various combinations of histone marks control gene expression in cell-type specific manner and a new term has been coined to capture this concept: the histone code.

The prototypical histone mark is histone acetylation. Histone acetyl transferase and histone deacetylases are the catalytic machines involved in modulation of this histone mark although typically these enzymes are parts of multiprotein complexes containing other proteins involved in reading and modifying histone marks. The components of these protein complexes are typically cell type and typically comprise transcriptional regulators, repressors, co-reppresors, receptors associated with gene expression modulation (e.g., estrogen or androgen receptor). Histone deacetylase inhibitors alter the histone acetylation profile of chromatin. Accordingly, histone deacetylase inhibitors like SAHA, TSA, and many others have been shown to alter gene expression in various in vitro and in vivo animal models. Clinically, histone deacetylase inhibitor have demonstrated activity in the cancer setting and are being investigated for oncology indications as well as for neurological conditions and other diseases.

Another modification that is involved in regulating gene expression is histone methylation including lysine and arginine methylation. The methylation status of histone lysines has recently been shown to be important in dynamically regulating gene expression.

A group of enzymes known as histone lysine methyl transferases and histone lysine demethylases are involved histone lysine modifications. One particular human histone lysine demethylase enzyme called Lysine Specific Demethylase-1 (LSD1) was recently discovered (Shi et al. (2004) *Cell* 119: 941) to be involved in this crucial histone modification. LSD1 has a fair degree of structural similarity, and amino acid identity/homology to polyamine oxidases and monoamine oxidases, all of which (i.e., MAO-A, MAO-B and LSD1) are flavin dependent amine oxidases which catalyze the oxidation of nitrogen-hydrogen bonds and/or nitrogen carbon bonds.

Several groups have reported LSD1 inhibitors in the literature. Sharma et al. recently reported a new series of urea and thiourea analogs based on an earlier series of polyamines which were shown to inhibit LSD1 and modulate histone methylation and gene expression in cells (J Med Chem. 2010 PMID: 20568780 [PubMed—as supplied by publisher]). Sharma et al. note that "To date, only a few existing compounds have been shown to inhibit LSD1." Some efforts were made to make analogs of the histone peptide that is methylated by the enzyme, other efforts have focused on more small molecule like molecules based on known MAO inhibitors. Gooden et al. reported trans-2-arylcyclopropylamine analogues that inhibit LSD1 with Ki values in the range of 188-566 micromolar (Gooden et al. ((2008) *Bioorg. Med. Chem. Let.* 18:3047-3051)). Most of these compounds were more potent against MAO-A as compared to MAO-B. Ueda et al. ((2009) J. Am. Chem. Soc. 131(48):17536-17537) reported cyclopropylamine analogs selective for LSD1 over MAO-A and MAO-B that were designed based on reported X-ray crystal structures of these enzymes with a phenylcyclopropylamine-FAD adduct and a FAD-N-propargyl lysine peptide. The reported IC50 values for phenylcyclopropylamine were about 32 micromolar for LSD1 whereas compounds 1 and 2 had values of 2.5 and 1.9 micromolar respectively.

Binda et al. examined a series of phenylcyclopropylamine derivatives in relation to their inhibitory activity against LSD1 and LSD2 as well as examining stereochemical issues in relation to the cyclopropyl ring (*J Am Chem Soc.* 2010 May 19; 132(19):6827-33). Binda et al. reported that their para substituted phenylcyclopropylamine derivatives are non-selective which as a group appear to be better MAO-A inhibitors than MAO-B inhibitors. Furthermore, their inhibitory activities against MAO-A and LSD1 were roughly the same.

Mimasu et al. disclose a series of phenylcyclopropylamine derivatives have benzoyl substitutions at the ortho-position ((2010) Biochemistry June 22. [Epub ahead of print] PMID: 20568732 [PubMed—as supplied by publisher]. Ortho-substituted compounds from this series without a benzoyl group in the ortho-position e.g., phenyl, alkoxy, or having a combination of ortho- and para-substitution appeared to be less potent inhibitors of LSD1 than those compounds having benzoyl substituents in the ortho-position. The most active compounds from this series had a benzoyl group at the ortho-position and one or two meta fluoro substitutions: biphenyls like S1310 and compounds having large groups in the para position were less effective LSD1 inhibitors.

The phenylcyclopropylamines have been the subject of many studies designed to elucidate a SAR for MAO inhibition. Kaiser et al. ((1962) *J. Med. Chem.* 5:1243-1265); Zirkle et al. ((1962) *J. Med. Chem.* 1265-1284; U.S. Pat. Nos. 3,365, 458; 3,471,522; 3,532,749) have disclosed the synthesis and activity of a number of phenylcyclopropylamine related compounds. Other phenylcyclopropylamine type compounds are disclosed in Bolesov et al. ((1974) *Zhurnal Organicheskoi Khimii* 10:8 1661-1669) and Russian Patent No. 230169 (19681030).

Studies have been conducted with phenylcyclopropylamine related compounds to determine selectivity for MAO-A versus MAO-B since MAO-A inhibitors can cause dangerous side-effects (see e.g., Yoshida et al. (2004) *Bioorg. Med Chem.* 12(10):2645-7652; Hruschka et al. (2008) *Biorg Med Chem.* (16):7148-7166; Folks et al. (1983) *J. Clin. Psychopharmacol.* (3)249; and Youdim et al. (1983) *Mod. Probl. Pharmacopsychiatry* (19):63).

In view of the lack of adequate treatments for conditions such as cancer and neurodegeneration, there is a desperate need for disease modifying drugs and drugs that work by inhibiting novel targets. There is a need for the development of better LSD1 selective inhibitors particularly those which selectively inhibit LSD1 and LSD1 in combination with MAO-B:

The present invention relates to the identification of compounds and their use in treating or preventing diseases. The present invention provides a compound of Formula (I) or a pharmaceutically acceptable salt or solvate thereof, pharmaceutical compositions comprising a compound of Formula (I) or a pharmaceutically acceptable salt or solvate thereof, and a pharmaceutically acceptable carrier, and their uses for treating or preventing diseases. One use of the compound of Formula (I) is for treating or preventing cancer. Another use for the compound of Formula (I) is to inhibit LSD1. The present invention thus relates to a compound of Formula (I) or an enantiomer, a diastereomer, or a mixture thereof, or a pharmaceutically acceptable salt or solvate thereof for use in treating or preventing cancer and other diseases associated to LSD1.

Accordingly, the present invention provides a compound of Formula (I) or a pharmaceutically acceptable salt or solvate thereof and, furthermore, relates to its use in treating or preventing disease (e.g., human disease):

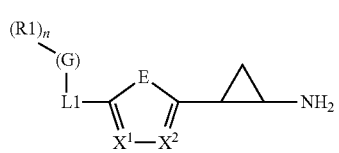

wherein:
E is —N(R3)-, —S—, —O— or —X³=X⁴—;
X¹ and X² are each independently C(R2) or N;
X³ and X⁴, when present, are each independently C(R2) or N;
L1 is —NH— or —NH—CH₂—;
G is a cyclyl group (as shown in formula (I), the cyclyl group G has n substituents R1);
each R1 is independently chosen from alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl;
each R2 is independently chosen from —H, alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each R2 group has 1, 2, or 3 independently chosen optional substituents, and further wherein two R2 groups bound to adjacent carbon atoms can be taken together to form a heterocyclyl or aryl group having 1, 2, or 3 independently chosen optional substituents; wherein said optional substituents are each independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfinyl, sulfonyl, sulfonamide, urea or carbamate;
R3 is —H or an (C1-C6)alkyl group;
each L2 is independently chosen from alkylene or heteroalkylene; and
n is 0, 1, 2, 3, 4 or 5.

Also included within the scope of the invention are all isomers, including all stereoisomers, and mixtures thereof, of a compound of formula I, as well as all salts and solvates thereof. Also included within the scope of the invention are all physical forms (including polymorphic forms and amorphous forms) of any such compounds.

The compounds of the invention, in particular the compounds of Formula (I), are useful in the treatment or prevention of a disease or disorder, e.g., in a mammal and, in particular, in a human. The disease or disorder to be treated or prevented is preferably chosen from cancer, a neurological condition or disease, or a viral infection.

In a related aspect, the invention provides a pharmaceutical composition comprising a compound of Formula (I) or an enantiomer, a diastereomer, or a mixture thereof, or a pharmaceutically acceptable salt or solvate thereof as defined below and a pharmaceutically acceptable carrier. Preferred embodiments of the compound of Formula (I) for use in the composition are defined and described herein below in more detail.

In another aspect, the invention provides a method of treating or preventing a disease, disorder or condition comprising administering, to a patient/subject (preferably a human) in need of such treatment or prevention, a therapeutically effective amount of a pharmaceutical composition comprising a compound of Formula (I) as described above or as in the embodiments thereof as described below, or a pharmaceutically acceptable salt thereof, and a pharmaceutically acceptable carrier. This aspect can be reformulated as a compound of Formula (I) as defined above in the first aspect of the invention for use as a medicine. Accordingly, the invention relates to the compound of Formula (I) or an enantiomer, a diastereomer, or a mixture thereof, or a pharmaceutically acceptable salt or solvate thereof, or a pharmaceutical composition comprising any of the aforementioned entities and a pharmaceutically acceptable carrier, for use as a medicament.

In a related aspect, the invention, provides a pharmaceutical composition for use in treating or preventing a disease, disorder or condition wherein said composition comprises a therapeutically effective amount of a compound of Formula (I) sufficient for treating or preventing said disease, disorder or condition. In a more specific embodiment the invention provides a compound of Formula (I) or an enantiomer, a diastereomer, or a mixture thereof, or a pharmaceutically acceptable salt or solvate thereof, or a pharmaceutical composition comprising any of the aforementioned entities and a pharmaceutically acceptable carrier for use in the treatment or prevention of a disease associated with LSD1. In another embodiment, the invention provides the use of a compound of Formula (I) or an enantiomer, a diastereomer, or a mixture thereof, or a pharmaceutically acceptable salt or solvate thereof, for the manufacture of a medicament for the treatment or prevention of a disease associated with LSD1.

In yet another aspect, the invention provides a method of inhibiting LSD1 activity comprising administering, to a patient in need of such treatment, a therapeutically effective amount of a pharmaceutical composition comprising a compound of Formula (I) or a pharmaceutically acceptable salt thereof, and a pharmaceutically acceptable carrier sufficient to inhibit LSD1 activity. Preferably the patient is a human. This aspect can be reformulated as a compound of Formula (I) as herein defined for use as a LSD1 inhibitor. In a related aspect, a method for treating an individual is provided, said method comprising identifying an individual in need of treatment or prevention and administering to said individual a therapeutically effective amount of a compound of Formula (I). In a preferred aspect, the therapeutically effective amount of a compound of Formula (I) is an amount sufficient to inhibit LSD1. In another preferred aspect, the therapeutically effective amount is an amount sufficient to modulate histone methylation levels. In another preferred aspect, the therapeutically effective amount is an amount sufficient to modulate histone-3 lysine-4 methylation levels. In another preferred aspect, the therapeutically effective amount is an amount sufficient to modulate histone-3 lysine-9 methylation levels. In another preferred aspect, the therapeutically effective amount is an amount sufficient to modulate gene expression levels. Preferred embodiments of the compounds of Formula (I) for use in the composition and method of this aspect of the invention are as described in more detail herein.

In again another aspect, the invention provides a method of treating or preventing cancer comprising administering, to a patient (e.g., a human) in need of such treatment or prevention, a therapeutically effective amount of a pharmaceutical composition comprising a compound of Formula (I) as defined above or as defined in the embodiments described in more detail herein, and a pharmaceutically acceptable carrier. This aspect can be reformulated as a compound of Formula (I) as defined above in the first aspect of the invention for use in the treatment or prevention of cancer. In a related aspect, the invention provides the use of a compound of Formula (I) as defined above in the first aspect of the invention for the manufacture of a medicament for the treatment or prevention of cancer. In a related aspect, the invention provides a pharmaceutical composition for use in treating or preventing cancer wherein said composition comprises a therapeutically effective amount of a compound of Formula (I) sufficient for treating or preventing cancer. In another related aspect, the invention provides a compound of Formula (I) or a pharmaceutical composition for use in the treatment or prevention of a cancer wherein said cancer is chosen from breast cancer, lung cancer, prostate cancer, colorectal cancer, brain cancer, skin cancer, blood cancer (e.g., leukemia) and lymphoma, wherein said composition comprises a therapeutically effective amount of a compound of Formula (I) sufficient for treating or preventing said cancer. In a preferred aspect, the therapeutically effective amount of a compound of Formula (I) is an amount sufficient to inhibit LSD1. In another preferred aspect, the therapeutically effective amount is an amount sufficient to modulate histone methylation levels. In another preferred aspect, the therapeutically effective amount is an amount sufficient to modulate histone-3 lysine-4 methylation levels. In another preferred aspect, the therapeutically effective amount is an amount sufficient to modulate histone-3 lysine-9 methylation levels. In another preferred aspect, the therapeutically effective amount is an amount sufficient to modulate gene expression levels In again another aspect, the invention provides a method of treating or preventing a neurological disease or condition comprising administering, to a patient (e.g., a human) in need of such treatment or prevention, a therapeutically effective amount of a pharmaceutical composition comprising a compound of Formula (I) as defined above or as defined in the embodiments described in more detail herein, and a pharmaceutically acceptable carrier. This aspect can be reformulated as a compound of Formula (I) as defined above for use in the treatment or prevention of a neurological condition or disease. This related aspect, the invention provides the use of a compound of Formula (I) as defined above for the manufacture of a medicament for the treatment or prevention of a neurological condition or disease. In a related aspect, the invention provides a pharmaceutical composition for use in treating or preventing a neurological condition or disease wherein said composition comprises a therapeutically effective amount of a compound of Formula (I) sufficient for treating or preventing said neurological disease or condition. In another related aspect, the invention provides a compound of Formula (I) or a pharmaceutical composition for use in the treatment or prevention of a neurological disease or condition wherein said neurological disease or condition is chosen from depression, Alzheimer disease, Huntington disease, Parkinson disease, or Dementia with Lewy Bodies, wherein said composition comprises a therapeutically effective amount of a compound of Formula (I) sufficient for treating or preventing said disease or condition. In a preferred aspect, the therapeutically effective amount of a compound of Formula (I) is an amount sufficient to inhibit LSD1. In another preferred aspect, the therapeutically effective amount is an amount sufficient to modulate histone methylation levels. In another preferred aspect, the therapeutically effective amount is an amount sufficient to modulate histone-3 lysine-4 methylation levels. In another preferred aspect, the therapeutically effective amount is an amount sufficient to modulate histone-3 lysine-9 methylation levels. In another preferred aspect, the therapeutically effective amount is an amount sufficient to modulate gene expression levels.

Thus, in one embodiment of the invention, the pharmaceutical composition comprising a LSD1 inhibitor of Formula (I), or a pharmaceutically acceptable salt thereof is useful for treating and/or preventing a disease in an individual. In one aspect, a therapeutically effective amount of the composition is administered to an individual, the amount being sufficient to prevent or treat a disease. In a more specific aspect, the disease is cancer. In an even more specific aspect, the disease is a cancer chosen from prostate cancer, brain cancer, colorectal cancer, lung cancer, breast cancer, skin cancer, blood cancer (e.g., leukemia), or lymphoma. In one specific aspect, the cancer is prostate cancer. In one specific aspect, the cancer is lung cancer. In one specific aspect, the cancer is brain cancer. In one specific aspect, the cancer is blood cancer (e.g., leukemia). In one specific aspect, the cancer is breast cancer. In one specific aspect, the cancer is colorectal cancer. In one specific aspect, the cancer is lymphoma. In another preferred aspect, the therapeutically effective amount is an amount sufficient to inhibit LSD1. In another preferred aspect, the therapeutically effective amount is an amount sufficient to modulate histone methylation levels. In another preferred aspect, the therapeutically effective amount is an amount sufficient to modulate histone-3 lysine-4 methylation levels. In another preferred aspect, the therapeutically effective amount is an amount sufficient to modulate histone-3 lysine-9 methylation levels. In another preferred aspect, the therapeutically effective amount is an amount sufficient to modulate gene expression levels.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Other features and advantages of the invention will be apparent from the following detailed description, and from the claims.

The present invention relates to the identification of compounds and their use in treating or preventing diseases. The present invention provides compounds of Formula (I) or salts and solvates thereof, preferably pharmaceutically acceptable salts or solvates thereof, pharmaceutical compositions comprising a compound of Formula (I) or a pharmaceutically acceptable salt or solvate thereof and a pharmaceutically acceptable carrier, and their use for treating or preventing diseases. One use of the compounds of Formula (I) is for treating or preventing cancer. In particular it was found that the cyclylpropylamine (in particular, phenylcyclopropylamine and pyridinylcyclopropylamine) compounds of Formula (I) are unexpectedly potent LSD1 inhibitors. The compounds of Formula (I) as described and defined herein are generally better inhibitors of LSD1 by a factor of about 20 or more as compared to tranylcypromine, with improved selectivity against MAO-A.

Accordingly, the invention provides a compound of Formula (I) or a pharmaceutically acceptable salt or solvate thereof and, furthermore, relates to its use in treating or preventing a disease or disorder (such as, e.g., cancer):

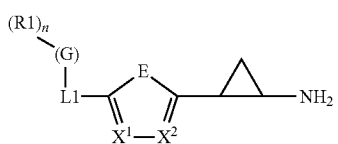

(I)

The compound of Formula (I) is described in more detail in the following.

E is —N(R3)-, —S—, —O— or —X$^3$═X$^4$—. Preferably, E is —X$^3$═X$^4$—.

X$^1$ and X$^2$ are each independently C(R2) or N.

X$^3$ and X$^4$, when present, are each independently C(R2) or N.

In a preferred embodiment, the ring moiety containing E, X$^1$ and X$^2$ is chosen from:
a ring wherein E is —X$^3$═X$^4$—, one of X$^1$, X$^2$, X$^3$, and X$^4$ is N or C(R2) and the other ones of X$^1$, X$^2$, X$^3$, and X$^4$ are each independently C(R2);
(ii) a ring wherein E is —S— and X$^1$ and X$^2$ are independently C(R2),
(iii) a ring wherein E is —S—, X$^1$ is N and X$^2$ is C(R2); and
(iv) a ring wherein E is —S—, X$^1$ is C(R2) and X$^2$ is N.

Preferably, E is —X$^3$═X$^4$—, one of X$^1$, X$^2$, X$^3$, and X$^4$ is N or C(R2) and the other ones of X$^1$, X$^2$, X$^3$, and X$^4$ are each independently C(R2) (in particular, the other ones of X$^1$, X$^2$, X$^3$, and X$^4$ may each be CH). Accordingly, it is preferred that the ring moiety comprising E, X$^1$ and X$^2$ is a pyridinyl or phenyl ring.

More preferably, one of X$^1$, X$^2$, X$^3$, and X$^4$ is N and the other ones of X$^1$, X$^2$, X$^3$, and X$^4$ are each independently C(R2) (in particular, the other ones of X$^1$, X$^2$, X$^3$, and X$^4$ may each be CH). Accordingly, it is preferred that the ring moiety comprising E, X$^1$ and X$^2$ is a pyridinyl ring.

In a more preferred embodiment, X$^1$ is N, and X$^2$, X$^3$ and X$^4$ are each independently C(R2) (in particular, X$^2$, X$^3$ and X$^4$ may each be CH). In another preferred embodiment, X$^2$ is N and X$^1$, X$^3$ and X$^4$ are each independently C(R2) (in particular, X$^1$, X$^3$ and X$^4$ may each be CH).

L1 is —NH— or —NH—CH$_2$—.

It is to be understood that the group —NH—CH$_2$— can be present in either orientation. Accordingly, if L1 is —NH—CH$_2$—, the NH moiety in —NH—CH$_2$— can be bound to the ring moiety containing E, X$^1$ and X$^2$, and the CH$_2$ moiety in —NH—CH$_2$— can be bound to the group G. Alternatively, the NH moiety in —NH—CH$_2$— can be bound to the group G, and the CH$_2$ moiety in —NH—CH$_2$— can be bound to the ring moiety containing E, X$^1$ and X$^2$.

If L1 is —NH—CH$_2$—, it is preferred that the NH moiety in —NH—CH$_2$— is bound to the ring moiety containing E, X$^1$ and X$^2$, and that the CH$_2$ moiety in —NH—CH$_2$— is bound to the group G.

Preferably L1 is —NH— or NH—CH$_2$— wherein the NH moiety in —NH—CH$_2$— is hound to the ring moiety containing E, X$^1$ and X$^2$ and the CH$_2$ moiety in —NH—CH$_2$— is bound to the group G. In another embodiment, L1 is —NH—. In another embodiment L1 is —NH—CH$_2$— wherein the NH moiety in —NH—CH$_2$— is bound to the ring moiety containing E, X$^1$ and X$^2$ and the CH$_2$ moiety in —NH—CH$_2$— is bound to the group G.

G is a cyclyl group. As shown in Formula (I), the cyclyl group G has n substituents R1. Preferably, G is an aryl group or a heterocyclyl group, and more preferably G is an aryl or heteroaryl group.

In one preferred embodiment, G is a heterocyclyl group, more preferably G is a heteroaryl group (such as, e.g., thiophenyl, benzothiophenyl, indolyl or indazolyl), and even more preferably G is indolyl (in particular but without limitation, 1H-indolyl, such as, e.g., 1-H-indol-7-yl) or indazolyl (in particular but without limitation, 1H-indazolyl, such as, e.g., 1H-indazol-7-yl).

In another preferred embodiment, G is an aryl group (such as, e.g., phenyl or naphthyl), and more preferably G is phenyl.

In another embodiment, G is phenyl, indolyl or indazolyl, and preferably G is phenyl, 1H-indolyl or 1H-indazolyl.

Each R1 is independently chosen from alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl.

Preferably, each R1 is independently chosen from alkyl, alkynyl, aryl, amino, amido, nitro, halo, haloalkyl, haloalkoxy, cyano, heterocyclyl (e.g., heteroaryl), sulfonyl, sulfonamide, hydroxyl, or alkoxy.

More preferably, each R1 is independently chosen from lower alkyl, lower alkynyl, lower aryl, amino, amido, nitro, halo, lower haloalkyl, cyano, heterocyclyl, sulfonyl, sulfonamide, hydroxyl, or alkoxy.

More preferably, each R1 is independently chosen from lower alkyl, lower alkynyl, amido, halo, lower haloalkyl, cyano, hydroxyl, or alkoxy.

Even more preferably, each R1 is independently chosen from —CF$_3$, —OCH$_3$, halo (in particular, —Cl), —CN, —CH$_3$, —OH, ethynyl or —C(═O)NH$_2$.

Each R2 is independently chosen from —H, alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Each R2 group has 1, 2, or 3 independently chosen optional substituents (i.e., each R2 group optionally has 1, 2, or 3 independently chosen substituents as defined below). Furthermore, two R2 groups bound to adjacent carbon atoms (i.e., adjacent ring carbon atoms of the ring moiety comprising E, X$^1$ and X$^2$; the adjacent carbon atoms can thus be X$^1$ and X$^2$ or can be X$^3$ and X$^4$) can be taken together to form a heterocyclyl or aryl group having 1, 2, or 3 independently chosen optional substituents.

Said optional substituents (i.e., said optional substituents bound to the R2 group or said optional substituents bound to the heterocyclyl or aryl group formed from two R2 groups bound to adjacent carbon atoms) are each independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfinyl, sulfonyl, sulfonamide, urea or carbamate. Preferably, the optional substituents are each independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio.

Preferably, each R2 is independently chosen from —H, hydroxyl; haloalkyl, alkoxy, halo, amido, arylalkyl, heterocyclylalkyl, arylalkoxy, or heterocyclylalkoxy, wherein each R2 has 1, 2, or 3 optional substituents (as defined and described herein above).

More preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents independently chosen from lower alkyl, lower haloalkyl, lower haloalkoxy, amino(C1-C6)alkyl, halo, lower alkoxy, or amido.

Even more preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents independently chosen from chloro, fluoro, —CH$_2$NH$_2$, —CH$_2$CH$_2$NH$_2$, or —OCH$_3$.

Preferably, each R2 is —H or 1 or 2 groups R2 are not —H. In one embodiment, each R2 is —H. It is to be understood that, if R2 is H, this group does not have any optional substituents. In another embodiment, 1 or 2 groups R2 are different from —H.

R3 is –H or an (C1-C6)alkyl group.

Preferably, R3 is —H or (C1-C4)alkyl. More preferably, R3 is —H, methyl or ethyl. Even more preferably, R3 is —H.

Each L2 is independently chosen from alkylene or heteroalkylene.

Said alkylene is, for example, a (C1-C6)alkylene (including, e.g., methylene, ethylene, propylene, butylene, pentylene, or hexylene), in particular a linear (C1-C6)alkylene. Said heteroalkylene is, for example, chosen from —CH$_2$OCH$_2$—, —CH$_2$SCH$_2$—, —CH$_2$NHCH$_2$—, —CH$_2$S—, or —CH$_2$NCH(CH$_3$)CH$_2$—. Preferably, each L2 is independently chosen from (C1-C6)alkylene, more preferably from linear (C1-C6)alkylene.

n is 0, 1, 2, 3, 4 or 5. Preferably, n is 0, 1, 2, 3, or 4. More preferably, n is 0, 1, 2, or 3. Even more preferably, n is 1 or 2. Even more preferably, n is 1.

It is to be understood that, if n is 0, the group G is not substituted with any group R1 (i.e., the group G is substituted with hydrogen instead of R1 in that case).

Preferably, the compound of Formula (I) is in the trans configuration in respect of the cyclopropyl ring, i.e., the amino group bound to the cyclopropyl ring and the ring moiety comprising E, X$^1$ and X$^2$, which ring moiety is bound to the cyclopropyl ring, are in trans orientation in respect of the cyclopropyl ring. Accordingly, it is preferred that the compound of Formula (I) is a compound of the following formula:

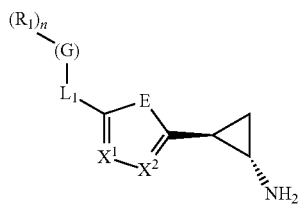

or a pharmaceutically acceptable salt or solvate thereof, wherein E, X$^1$, X$^2$, L1 (shown as L$_1$ in the above formula), G, R1, and n have the meanings or the preferred meanings described and defined herein for the compound of Formula (I).

Preferably, the compound of Formula (I) comprises a racemic mixture of compounds of Formula (I). Accordingly, it is preferred that the compound of Formula (I) is a mixture of compounds of Formula (I) in the (1S,2R) and (1R,2S) configurations in respect of the cyclopropyl ring, i.e., the amino group bound to the cyclopropyl ring and the ring moiety comprising E, X$^1$ and X$^2$, which ring moiety is bound to the cyclopropyl ring, are in (1S,2R) and (1R,2S) configuration in respect of the cyclopropyl ring.

More preferably, the compound of Formula (I) is in one enantiomeric configuration. Accordingly, it is preferred that the compound of Formula (I) is in the (1S,2R) or in the (1R,2S) configuration in respect of the cyclopropyl ring, i.e., the amino group bound to the cyclopropyl ring and the ring moiety comprising E, X$^1$ and X$^2$, which ring moiety is bound to the cyclopropyl ring, are in (1S,2R) or (1R,2S) orientation in respect of the cyclopropyl ring. Thus, in one preferred embodiment the compound of Formula (I) is (1S,2R) with substantially little or no (1R,2S) wherein substantially little or no (1R,2S) refers to a compound of Formula (I) having 90% or more, preferably, 95% or more, and even more preferably 99% or more (1S,2R) and preferably less than 10%, more preferably less than 5% and even more preferably less than 1% (1R,2S). In another preferred embodiment the compound of Formula (I) is (1R,2S) with substantially little or no (1S,2R) wherein substantially little or no (1S,2R) refers to a compound of Formula (I) having 90% or more, preferably, 95% or more, and even more preferably 99% or more (1R,2S) and preferably less than 10%, more preferably less than 5% and even more preferably less than 1% (1S,2R).

Thus, in one embodiment, the invention provides a compound of Formula (I) or a pharmaceutically acceptable salt or solvate thereof, wherein L1 is —NH— and E is —X$^3$═X$^4$—. In a preferred aspect of this embodiment, X$^1$ is N and X$^2$, X$^3$ and X$^4$ are each —CH— and G is phenyl optionally having 1, 2, 3, or 4 substituents R1 which are each independently chosen from alkyl, alkynyl, aryl, amino, amido, nitro, halo, haloalkyl, haloalkoxy, cyano, heterocyclyl, sulfonyl, sulfonamide, hydroxyl, or alkoxy. It is furthermore preferred that each substituent R1 is independently chosen from —CF$_3$, —OCH$_3$, —Cl, —CN, —CH$_3$, —OH, ethynyl or —C(═O)NH$_2$.

In one embodiment, the invention provides a compound of Formula (I) or a pharmaceutically acceptable salt or solvate thereof, wherein L1 is —NH— and E is —X$^3$═X$^4$—. In a preferred aspect of this embodiment, X$^1$ is N and X$^2$, X$^3$ and X$^4$ are each —CH— and G is a heterocyclyl. Preferably G is indolyl or indazolyl.

In one embodiment, the invention provides a compound of Formula (I) or a pharmaceutically acceptable salt or solvate thereof, wherein E is —X$^3$═X$^4$— and L1 is —NH—CH$_2$— (wherein it is preferred that the NH moiety of said —NH—

CH$_2$— is bound to the ring moiety comprising E, X$^1$ and X$^2$, and that the CH$_2$ moiety of said —NH—CH$_2$— is bound to the group G). In a preferred aspect of this embodiment, X$^1$ is N and X$^2$, X$^3$ and X$^4$ are each —CH— and G is phenyl optionally having 1, 2, 3, or 4 substituents R1 which are each independently chosen from alkyl, alkynyl, aryl, amino, amido, nitro, halo, haloalkyl, haloalkoxy, cyano, heterocyclyl, sulfonyl, sulfonamide, hydroxyl, or alkoxy. It is furthermore preferred that each substituent R1 is independently chosen from —CF$_3$, —OCH$_3$, —Cl, —CN, —CH$_3$, —OH, ethynyl or —C(=O)NH$_2$.

In one embodiment, the invention provides a compound of Formula (I) or a pharmaceutically acceptable salt or solvate thereof; wherein the groups E, X$^2$, X$^3$, X$^4$, L1, G, R1, R2, L2, and n have the following meanings.

E is —X$^3$=X$^4$—.

X$^1$ is N.

X$^2$, X$^3$ and X$^4$ are each independently C(R2). Preferably, X$^2$, X$^3$ and X$^4$ are each CH.

L1 is —NH—.

G is phenyl. As shown in Formula (I), the group G has n substituents R1.

Each R1 is independently chosen from alkyl, alkenyl, alkynyl, cyclyl, -L2-cyclyl, -L2-amino, L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each R1 is independently chosen from alkyl, alkynyl, aryl, amino, amido, nitro, halo, haloalkyl, haloalkoxy, cyano, heterocyclyl (e.g., heteroaryl), sulfonyl, sulfonamide, hydroxyl, or alkoxy. More preferably, each R1 is independently chosen from lower alkyl, lower alkynyl, lower aryl, amino, amido, nitro, halo, lower haloalkyl, cyano, heterocyclyl, sulfonyl, sulfonamide, hydroxyl, or alkoxy. Even more preferably, each R1 is independently chosen from —CF$_3$, —OCH$_3$, halo (in particular, —Cl), —CN, —CH$_3$, —OH, ethynyl, or —C(=O)NH$_2$.

Each R2 is independently chosen from —H, alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Each R2 group has 1, 2, or 3 independently chosen optional substituents (i.e., each R2 group optionally has 1, 2, or 3 independently chosen substituents as defined below). Furthermore, two R2 groups bound to adjacent carbon atoms (i.e., adjacent ring carbon atoms of the ring moiety comprising E, X$^1$ and X$^2$; the adjacent carbon atoms may thus be X$^1$ and X$^2$ or may be X$^3$ and X$^4$) can be taken together to form a heterocyclyl or aryl group having 1, 2, or 3 independently chosen optional substituents. Said optional substituents (i.e., said optional substituents bound to the R2 group or said optional substituents bound to the heterocyclyl or aryl group formed from two R2 groups bound to adjacent carbon atoms) are each independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfinyl, sulfonyl, sulfonamide, urea or carbamate. Preferably, the optional substituents are each independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio.

Preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents (as defined and described herein above). More preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents independently chosen from lower alkyl, lower haloalkyl, lower haloalkoxy, amino(C1-C6)alkyl, halo, lower alkoxy, or amido. Even more preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents independently chosen from chloro, fluoro, —CH$_2$NH$_2$, —CH$_2$CH$_2$NH$_2$, or —OCH$_3$. Even more preferably, each R2 is —H.

Each L2 is independently chosen from alkylene or heteroalkylene. Said alkylene is, for example, a (C1-C6)alkylene (including, e.g., methylene, ethylene, propylene, butylene, pentylene, or hexylene), in particular a linear (C1-C6)alkylene. Said heteroalkylene is, for example, chosen from —CH$_2$OCH$_2$—, —CH$_2$SCH$_2$—, —CH$_2$NHCH$_2$—, —CH$_2$S—, or CH$_2$NCH(CH$_3$)CH$_2$—. Preferably, each L2 is independently chosen from (C1-C6)alkylene, more preferably from linear (C1-C6)alkylene.

n is 0, 1, 2, 3, 4 or 5. Preferably, n is 0, 1, 2, 3, or 4. More preferably, n is 0, 1, 2, or 3. Even more preferably, n is 1 or 2. Even more preferably, n is 1.

The invention further relates to the compound of Formula (I) or a pharmaceutically acceptable salt or solvate thereof, as defined in the above described embodiment, for use as a medicament, for use in the treatment or prevention of cancer (such as, e.g., breast cancer, lung cancer, prostate cancer, colorectal cancer, brain cancer, skin cancer, blood cancer, leukemia or lymphoma), for use in the treatment or prevention of a neurological disease or condition (such as, e.g., depression, Alzheimer disease, Huntington disease, Parkinson disease, or Dementia with Lewy Bodies), for use in the treatment or prevention of a viral infection (such as, e.g., a viral infection caused by and/or associated with HIV, or a herpesvirus infection which may be caused by and/or may be associated with a herpesvirus chosen from HSV-1, HSV-2, or Epstein-Barr virus) or for use in treating or preventing viral reactivation after latency (such as, e.g., reactivation of a herpesvirus after latency, or reactivation of a herpesvirus chosen from HSV-1, HSV-2, and Epstein-Barr virus.).

In one embodiment, the invention provides a compound of Formula (I) or a pharmaceutically acceptable salt or solvate thereof, wherein the groups E, X$^1$, X$^2$, X$^3$, X$^4$, L1, G, R1, R2, L2, and n have the following meanings.

E is —X$^3$=X$^4$—.

X$^1$ is N.

X$^2$, X$^3$ and X$^4$ are each independently C(R2). Preferably, X$^2$, X$^3$ and X$^4$ are each CH.

L1 is —NH—.

G is a heterocyclyl group. Preferably, G is a heteroaryl group. More preferably, G is selected from thiophenyl, benzothiophenyl, indolyl or indazolyl. Even more preferably, G is indolyl (in particular but without limitation, 1H-indolyl, such as, e.g., 1-H-indol-7-yl) or indazolyl (in particular but without limitation, 1H-indazolyl, such as, e.g., 1H-indazol-7-yl). As shown in Formula (I), the group G has n substituents R1.

Each R1 is independently chosen from alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each R1 is independently chosen from alkyl, alkynyl, aryl, amino, amido, nitro, halo, haloalkyl, haloalkoxy, cyano, heterocyclyl (e.g., heteroaryl), sulfonyl, sulfonamide, hydroxyl, or alkoxy. More preferably, each R1 is independently chosen from lower alkyl, lower alkynyl, lower aryl, amino, amido, nitro, halo, lower haloalkyl, cyano, heterocyclyl, sulfonyl, sulfonamide, hydroxyl, or alkoxy. Even more preferably, each R1 is independently chosen from —CF$_3$, —OCH$_3$, halo (in particular, —Cl), —CN, —CH$_3$, —OH, ethynyl, or —C(=O)NH$_2$.

Each R2 is independently chosen from —H, alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Each R2 group has 1, 2, or 3 independently chosen optional substituents (i.e., each R2 group optionally has 1, 2, or 3 independently chosen substituents as defined below). Furthermore, two R2 groups bound to adjacent carbon atoms (i.e., adjacent ring carbon atoms of the ring moiety comprising E, $X^1$ and $X^2$; the adjacent carbon atoms may thus be $X^1$ and $X^2$ or may be $X^3$ and $X^4$) can be taken together to form a heterocyclyl or aryl group having 1, 2, or 3 independently chosen optional substituents. Said optional substituents (i.e., said optional substituents bound to the R2 group or said optional substituents bound to the heterocyclyl or aryl group formed from two R2 groups bound to adjacent carbon atoms) are each independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfinyl, sulfonyl, sulfonamide, urea or carbamate. Preferably, the optional substituents are each independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio.

Preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents (as defined and described herein above). More preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents independently chosen from lower alkyl, lower haloalkyl, lower haloalkoxy, amino(C1-C6)alkyl, halo, lower alkoxy, or amido. Even more preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents independently chosen from chloro, fluoro, —CH$_2$NH$_2$, —CH$_2$CH$_2$NH$_2$, or —OCH$_3$. Even more preferably, each R2 is —H.

Each L2 is independently chosen from alkylene or heteroalkylene. Said alkylene is, for example, a (C1-C6)alkylene (including, e.g., methylene, ethylene, propylene, butylene, pentylene, or hexylene), in particular a linear (C1-C6)alkylene. Said heteroalkylene is, for example, chosen from —CH$_2$OCH$_2$—, —CH$_2$SCH$_2$—, —CH$_2$NHCH$_2$—, —CH$_2$S—, or —CH$_2$NCH(CH$_3$)CH$_2$—. Preferably, each L2 is independently chosen from (C1-C6)alkylene, more preferably from linear (C1-C6)alkylene.

n is 0, 1, 2, 3, 4 or 5. Preferably, n is 0, 1, 2, 3, or 4. More preferably, n is 0, 1, 2, or 3. Even more preferably, n is 1 or 2. Even more preferably, n is 1.

The invention further relates to the compound of Formula (I) or a pharmaceutically acceptable salt or solvate thereof, as defined in the above described embodiment, for use as a medicament, for use in the treatment or prevention of cancer (such as, e.g., breast cancer, lung cancer, prostate cancer, colorectal cancer, brain cancer, skin cancer, blood cancer, leukemia or lymphoma), for use in the treatment or prevention of a neurological disease or condition (such as, e.g., depression, Alzheimer disease, Huntington disease, Parkinson disease, or Dementia with Lewy Bodies), for use in the treatment or prevention of a viral infection (such as, e.g., a viral infection caused by and/or associated with HIV, or a herpesvirus infection which may be caused by and/or may be associated with a herpesvirus chosen from HSV-1, HSV-2, or Epstein-Barr virus), or for use in treating or preventing viral reactivation after latency (such as, e.g., reactivation of a herpesvirus after latency, or reactivation of a herpesvirus chosen from HSV-1, HSV-2, and Epstein-Barr virus.).

In one embodiment, the invention provides a compound of Formula (I) or a pharmaceutically acceptable salt or solvate thereof, wherein the groups E, $X^1$, $X^2$, $X^3$, $X^4$, L1, G, R1, R2, L2, and n have the following meanings.

E is —$X^3$=$X^4$—.

$X^1$ is N.

$X^2$, $X^3$ and $X^4$ are each independently C(R2). Preferably, $X^2$, $X^3$ and $X^4$ are each CH.

L1 is —NH—CH$_2$—.

The group —NH—CH$_2$— may be present in either orientation. Accordingly, the NH moiety in —NH—CH$_2$— can be bound to the ring moiety containing E, $X^1$ and $X^2$, and the CH$_2$ moiety in —NH—CH$_2$— can be bound to the group G. Alternatively, the NH moiety in —NH—CH$_2$— can be bound to the group G, and the CH$_2$ moiety in —NH—CH$_2$— can be bound to the ring moiety containing E, $X^1$ and $X^2$. Preferably, the NH moiety in —NH—CH$_2$— is bound to the ring moiety containing E, $X^1$ and $X^2$, and that the CH$_2$ moiety in —NH—CH$_2$— is bound to the group G.

G is phenyl. As shown in Formula (I), the group G has n substituents R1.

Each R1 is independently chosen from alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each R1 is independently chosen from alkyl, alkynyl, aryl, amino, amido, nitro, halo, haloalkyl, haloalkoxy, cyano, heterocyclyl (e.g., heteroaryl), sulfonyl, sulfonamide, hydroxyl, or alkoxy. More preferably, each R1 is independently chosen from lower alkyl, lower alkynyl, lower aryl, amino, amido, nitro, halo, lower haloalkyl, cyano, heterocyclyl, sulfonyl, sulfonamide, hydroxyl, or alkoxy. Even more preferably, each R1 is independently chosen from —CF$_3$, —OCH$_3$, halo (in particular, —Cl), —CN, —CH$_3$, —OH, ethynyl, or —C(=O)NH$_2$.

Each R2 is independently chosen from —H, alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Each R2 group has 1, 2, or 3 independently chosen optional substituents (i.e., each R2 group optionally has 1, 2, or 3 independently chosen substituents as defined below). Furthermore, two R2 groups bound to adjacent carbon atoms (i.e., adjacent ring carbon atoms of the ring moiety comprising E, $X^1$ and $X^2$; the adjacent carbon atoms may thus be $X^1$ and $X^2$ or may be $X^3$ and $X^4$) can be taken together to form a heterocyclyl or aryl group having 1, 2, or 3 independently chosen optional substituents. Said optional substituents (i.e., said optional substituents bound to the R2 group or said optional substituents bound to the heterocyclyl or aryl group formed from two R2 groups bound to adjacent carbon atoms) are each independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfinyl, sulfonyl, sulfonamide, urea or carbamate. Preferably, the optional substituents are each independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio.

Preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents (as defined and described herein above). More preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents independently chosen from lower alkyl, lower haloalkyl, lower haloalkoxy, amino(C1-C6)alkyl, halo, lower alkoxy, or amido. Even more preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents independently chosen from chloro, fluoro, —CH$_2$NH$_2$, —CH$_2$CH$_2$NH$_2$, or —OCH$_3$. Even more preferably, each R2 is —H.

Each L2 is independently chosen from alkylene or heteroalkylene. Said alkylene is, for example, a (C1-C6)alkylene (including, e.g., methylene, ethylene, propylene, butylene, pentylene, or hexylene), in particular a linear (C1-C6)alkylene. Said heteroalkylene is, for example, chosen from —CH$_2$OCH$_2$—, —CH$_2$SCH$_2$—, —CH$_2$NHCH$_2$—, —CH$_2$S—, or —CH$_2$NCH(CH$_3$)CH$_2$—. Preferably, each L2 is independently chosen from (C1-C6)alkylene, more preferably from linear (C1-C6)alkylene.

n is 0, 1, 2, 3, 4 or 5. Preferably, n is 0, 1, 2, 3, or 4. More preferably, n is 0, 1, 2, or 3. Even more preferably, n is 1 or 2. Even more preferably, n is 1.

The invention further relates to the compound of Formula (I) or a pharmaceutically acceptable salt or solvate thereof, as defined in the above described embodiment, for use as a medicament, for use in the treatment or prevention of cancer (such as, e.g., breast cancer, lung cancer, prostate cancer, colorectal cancer, brain cancer, skin cancer, blood cancer, leukemia or lymphoma), for use in the treatment or prevention of a neurological disease or condition (such as, e.g., depression, Alzheimer disease, Huntington disease, Parkinson disease, or Dementia with Lewy Bodies), for use in the treatment or prevention of a viral infection (such as, e.g., a viral infection caused by and/or associated with HIV, or a herpesvirus infection which may be caused by and/or may be associated with a herpesvirus chosen from HSV-1, HSV-2, or Epstein-Barr virus), or for use in treating or preventing viral reactivation after latency (such as, e.g., reactivation of a herpesvirus after latency, or reactivation of a herpesvirus chosen from HSV-1, HSV-2, and Epstein-Barr virus).

In one embodiment, the invention provides a compound of Formula (I) or a pharmaceutically acceptable salt or solvate thereof, wherein the groups E, $X^1$, $X^2$, $X^3$, $X^4$, L1, G, R1, R2, L2, and n have the following meanings.

E is —$X^3$═$X^4$—.

$X^1$ is N.

$X^2$, $X^3$ and $X^4$ are each independently C(R2). Preferably, $X^2$, $X^3$ and $X^4$ are each CH.

L1 is —NH—CH$_2$—:

The group —NH—CH$_2$— may be present in either orientation. Accordingly, the NH moiety in —NH—CH$_2$— can be bound to the ring moiety containing E, $X^1$ and $X^2$, and the CH$_2$ moiety in —NH—CH$_2$— can be bound to the group G. Alternatively, the NH moiety in —NH—CH$_2$— can be bound to the group G, and the CH$_2$ moiety in —NH—CH$_2$— can be bound to the ring moiety containing E, $X^1$ and $X^2$. Preferably, the NH moiety in —NH—CH$_2$— is bound to the ring moiety containing E, $X^1$ and $X^2$, and that the CH$_2$ moiety in —NH—CH$_2$— is bound to the group G.

G is a heterocyclyl group. Preferably, G is a heteroaryl group. More preferably, G is selected from thiophenyl, benzothiophenyl, indolyl or indazolyl. Even more preferably, G is indolyl (in particular but without limitation, 1H-indolyl, such as, e.g., 1-H-indol-7-yl) or indazolyl (in particular but without limitation, 1H-indazolyl, such as, e.g., 1H-indazol-7-yl). As shown in Formula (I), the group G has n substituents R1.

Each R1 is independently chosen from alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each R1 is independently chosen from alkyl, alkynyl, aryl, amino, amido, nitro, halo, haloalkyl, haloalkoxy, cyano, heterocyclyl (e.g., heteroaryl), sulfonyl, sulfonamide, hydroxyl, or alkoxy. More preferably, each R1 is independently chosen from lower alkyl, lower alkynyl, lower aryl, amino, amido, nitro, halo, lower haloalkyl, cyano, heterocyclyl, sulfonyl, sulfonamide, hydroxyl, or alkoxy. Even more preferably, each R1 is independently chosen from —CF$_3$, —OCH$_3$, halo (in particular, —Cl), —CN, —CH$_3$, —OH, ethynyl, or —C(═O)NH$_2$.

Each R2 is independently chosen from —H, alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Each R2 group has 1, 2, or 3 independently chosen optional substituents (i.e., each R2 group optionally has 1, 2, or 3 independently chosen substituents as defined below). Furthermore, two R2 groups bound to adjacent carbon atoms (i.e., adjacent ring carbon atoms of the ring moiety comprising E, $X^1$ and $X^2$; the adjacent carbon atoms may thus be $X^1$ and $X^2$ or may be $X^3$ and $X^4$) can be taken together to form a heterocyclyl or aryl group having 1, 2, or 3 independently chosen optional substituents. Said optional substituents (i.e., said optional substituents bound to the R2 group or said optional substituents bound to the heterocyclyl or aryl group formed from two R2 groups bound to adjacent carbon atoms) are each independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfinyl, sulfonyl, sulfonamide, urea or carbamate. Preferably, the optional substituents are each independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio.

Preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents (as defined and described herein above). More preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents independently chosen from lower alkyl, lower haloalkyl, lower haloalkoxy, amino(C1-C6)alkyl, halo, lower alkoxy, or amido. Even more preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents independently chosen from chloro, fluoro, —CH$_2$NH$_2$, —CH$_2$CH$_2$NH$_2$, or —OCH$_3$. Even more preferably, each R2 is —H.

Each L2 is independently chosen from alkylene or heteroalkylene. Said alkylene is, for example, a (C1-C6)alkylene (including, e.g., methylene, ethylene, propylene, butylene, pentylene, or hexylene), in particular a linear (C1-C6)alkylene. Said heteroalkylene is, for example, chosen from —CH$_2$OCH$_2$—, —CH$_2$SCH$_2$—, —CH$_2$NHCH$_2$—, —CH$_2$S—, or —CH$_2$NCH(CH$_3$)CH$_2$—. Preferably, each L2 is independently chosen from (C1-C6)alkylene, more preferably from linear (C1-C6)alkylene.

n is 0, 1, 2, 3, 4 or 5. Preferably, n is 0, 1, 2, 3, or 4. More preferably, n is 0, 1, 2, or 3. Even more preferably, n is 1 or 2. Even more preferably, n is 1.

The invention further relates to the compound of Formula (I) or a pharmaceutically acceptable salt or solvate thereof, as defined in the above described embodiment, for use as a medicament, for use in the treatment or prevention of cancer (such as, e.g., breast cancer, lung cancer, prostate cancer, colorectal cancer, brain cancer, skin cancer, blood cancer, leukemia or lymphoma), for use in the treatment or prevention of a neurological disease or condition (such as, e.g., depression, Alzheimer disease, Huntington disease, Parkinson disease, or Dementia with Lewy Bodies), for use in the treatment or prevention of a viral infection (such as, e.g., a viral infection caused by and/or associated with HIV, or a herpesvirus infection which may be caused by and/or may be associated with a herpesvirus chosen from HSV-1, HSV-2, or Epstein-Barr virus), or for use in treating or preventing viral reactivation after latency (such as, e.g., reactivation of a herpesvirus after latency, or reactivation of a herpesvirus chosen from HSV-1, HSV-2, and Epstein-Barr virus.).

In one embodiment, the invention provides a compound of Formula (I) or a phaiinaceutically acceptable salt or solvate thereof, wherein the groups E, X$^1$, X$^2$, X$^3$, X$^4$, L1, G, R1, R2, L2, and n have the following meanings.

E is —X$^3$=X$^4$—.

X$^2$ is N.

X$^1$, X$^3$ and X$^4$ are each independently C(R2). Preferably, X$^1$, X$^3$ and X$^4$ are each CH.

L1 is —NH—.

G is phenyl. As shown in Formula (I), the group G has n substituents R1.

Each R1 is independently chosen from alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each R1 is independently chosen from alkyl, alkynyl, aryl, amino, amido, nitro, halo, haloalkyl, haloalkoxy, cyano, heterocyclyl (e.g., heteroaryl), sulfonyl, sulfonamide, hydroxyl, or alkoxy. More preferably, each R1 is independently chosen from lower alkyl, lower alkynyl, lower aryl, amino, amido, nitro, halo, lower haloalkyl, cyano, heterocyclyl, sulfonyl, sulfonamide, hydroxyl, or alkoxy. Even more preferably, each R1 is independently chosen from —CF$_3$, —OCH$_3$, halo (in particular, —Cl), —CN, —CH$_3$, —OH, ethynyl, or —C(=O)NH$_2$.

Each R2 is independently chosen from —H, alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Each R2 group has 1, 2, or 3 independently chosen optional substituents (i.e., each R2 group optionally has 1, 2, or 3 independently chosen substituents as defined below). Furthermore, two R2 groups bound to adjacent carbon atoms (i.e., adjacent ring carbon atoms of the ring moiety comprising E, X$^1$ and X$^2$; the adjacent carbon atoms may thus be X$^1$ and X$^2$ or may be X$^3$ and X$^4$) can be taken together to form a heterocyclyl or aryl group having 1, 2, or 3 independently chosen optional substituents. Said optional substituents (i.e., said optional substituents bound to the R2 group or said optional substituents bound to the heterocyclyl or aryl group formed from two R2 groups bound to adjacent carbon atoms) are each independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfinyl, sulfonyl, sulfonamide, urea or carbamate. Preferably, the optional substituents are each independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio.

Preferably, each R2 is independently chosen from hydroxyl, haloalkyl, alkoxy, halo, amido, arylalkyl, heterocyclylalkyl, arylalkoxy, or heterocyclylalkoxy, wherein each R2 has 1, 2, or 3 optional substituents (as defined and described herein above). More preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents independently chosen from lower alkyl, lower haloalkyl, lower haloalkoxy, amino(C1-C6)alkyl, halo, lower alkoxy, or amido. Even more preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents independently chosen from chloro, fluoro, —CH$_2$NH$_2$, —CH$_2$CH$_2$NH$_2$, or —OCH$_3$. Even more preferably, each R2 is —H.

Each L2 is independently chosen from alkylene or heteroalkylene. Said alkylene is, for example, a (C1-C6)alkylene (including, e.g., methylene, ethylene, propylene, butylene, pentylene, or hexylene), in particular a linear (C1-C6)alkylene. Said heteroalkylene is, for example, chosen from —CH$_2$OCH$_2$—, —CH$_2$SCH$_2$—, —CH$_2$NHCH$_2$—, —CH$_2$S—, or —CH$_2$NCH(CH$_3$)CH$_2$—. Preferably, each L2 is independently chosen from (C1-C6)alkylene, more preferably from linear (C1-C6)alkylene.

n is 0, 1, 2, 3, 4 or 5. Preferably, n is 0, 1, 2, 3, or 4. More preferably, n is 0, 1, 2, or 3. Even more preferably, n is 1 or 2. Even more preferably, n is 1.

The invention further relates to the compound of Formula (I) or a pharmaceutically acceptable salt or solvate thereof, as defined in the above described embodiment, for use as a medicament, for use in the treatment or prevention of cancer (such as, e.g., breast cancer, lung cancer, prostate cancer, colorectal cancer, brain cancer, skin cancer, blood cancer, leukemia or lymphoma), for use in the treatment or prevention of a neurological disease or condition (such as, e.g., depression, Alzheimer disease, Huntington disease, Parkinson disease, or Dementia with Lewy Bodies), for use in the treatment or prevention of a viral infection (such as, e.g., a viral infection caused by and/or associated with HIV, or a herpesvirus infection which may be caused by and/or may be associated with a herpesvirus chosen from HSV-1, HSV-2, or Epstein-Barr virus), or for use in treating or preventing viral reactivation after latency (such as, e.g., reactivation of a herpesvirus after latency, or reactivation of a herpesvirus chosen from HSV-1, HSV-2, and Epstein-Barr virus).

In one embodiment, the invention provides a compound of Formula (I) or a pharmaceutically acceptable salt or solvate thereof, wherein the groups E, $X^1$, $X^2$, $X^3$, $X^4$, L1, G, R1, R2, L2, and n have the following meanings.

E is —$X^3$=$X^4$—.

$X^2$ is N.

$X^1$, $X^3$ and $X^4$ are each independently C(R2). Preferably, $X^1$, $X^3$ and $X^4$ are each CH.

L1 is —NH—.

G is a heterocyclyl group. Preferably, G is a heteroaryl group. More preferably, G is selected from thiophenyl, benzothiophenyl, indolyl or indazolyl. Even more preferably, G is indolyl (in particular but without limitation, 1H-indolyl, such as, e.g., 1-H-indol-7-yl) or indazolyl (in particular but without limitation, 1H-indazolyl, such as, e.g., 1H-indazol-7-yl). As shown in Formula (I), the group G has n substituents R1.

Each R1 is independently chosen from alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each R1 is independently chosen from alkyl, alkynyl, aryl, amino, amido, nitro, halo, haloalkyl, haloalkoxy, cyano, heterocyclyl (e.g., heteroaryl), sulfonyl, sulfonamide, hydroxyl, or alkoxy. More preferably, each R1 is independently chosen from lower alkyl, lower alkynyl, lower aryl, amino, amido, nitro, halo, lower haloalkyl, cyano, heterocyclyl, sulfonyl, sulfonamide, hydroxyl, or alkoxy. Even more preferably, each R1 is independently chosen from —$CF_3$, —$OCH_3$, halo (in particular, —Cl), —CN, —$CH_3$, —OH, ethynyl, or —C(=O)$NH_2$.

Each R2 is independently chosen from —H, alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Each R2 group has 1, 2, or 3 independently chosen optional substituents (i.e., each R2 group optionally has 1, 2, or 3 independently chosen substituents as defined below). Furthermore, two R2 groups bound to adjacent carbon atoms (i.e., adjacent ring carbon atoms of the ring moiety comprising E, $X^1$ and $X^2$; the adjacent carbon atoms may thus be $X^1$ and $X^2$ or may be $X^3$ and $X^4$) can be taken together to form a heterocyclyl or aryl group having 1, 2, or 3 independently chosen optional substituents. Said optional substituents (i.e., said optional substituents bound to the R2 group or said optional substituents bound to the heterocyclyl or aryl group formed from two R2 groups bound to adjacent carbon atoms) are each independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfinyl, sulfonyl, sulfonamide, urea or carbamate. Preferably, the optional substituents are each independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio.

Preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents (as defined and described herein above). More preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents independently chosen from lower alkyl, lower haloalkyl, lower haloalkoxy, amino(C1-C6)alkyl, halo, lower alkoxy, or amido. Even more preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents independently chosen from chloro, fluoro, —$CH_2NH_2$, —$CH_2CH_2NH_2$, or —$OCH_3$. Even more preferably, each R2 is —H.

Each L2 is independently chosen from alkylene or heteroalkylene. Said alkylene is, for example, a (C1-C6)alkylene (including, e.g., methylene, ethylene, propylene, butylene, pentylene, or hexylene), in particular a linear (C1-C6)alkylene. Said heteroalkylene can, for example, chosen from —$CH_2OCH_2$—, —$CH_2SCH_2$—, —$CH_2NHCH_2$—, —$CH_2S$—, or —$CH_2NCH(CH_3)CH_2$—. Preferably, each L2 is independently chosen from (C1-C6)alkylene, more preferably from linear (C1-C6)alkylene.

n is 0, 1, 2, 3, 4 or 5. Preferably, n is 0, 1, 2, 3, or 4. More preferably, n is 0, 1, 2, or 3. Even more preferably, n is 1 or 2. Even more preferably, n is 1.

The invention further relates to the compound of Formula (I) or a pharmaceutically acceptable salt or solvate thereof, as defined in the above described embodiment, for use as a medicament, for use in the treatment or prevention of cancer (such as, e.g., breast cancer, lung cancer, prostate cancer, colorectal cancer, brain cancer, skin cancer, blood cancer, leukemia or lymphoma), for use in the treatment or prevention of a neurological disease or condition (such as, e.g., depression, Alzheimer disease, Huntington disease, Parkinson disease, or Dementia with Lewy Bodies), for use in the treatment or prevention of a viral infection (such as, e.g., a viral infection caused by and/or associated with HIV, or a herpesvirus infection which may be caused by and/or may be associated with a herpesvirus chosen from HSV-1, HSV-2, or Epstein-Barr virus), or for use in treating or preventing viral reactivation after latency (such as, e.g., reactivation of a herpesvirus after latency, or reactivation of a herpesvirus chosen from HSV-1, HSV-2, and Epstein-Barr virus).

In one embodiment, the invention provides a compound of Formula (I) or a pharmaceutically acceptable salt or solvate thereof, wherein the groups E, $X^1$, $X^2$, $X^3$, $X^4$, L1, G, R1, R2, L2, and n have the following meanings.

E is $-X^3=X^4-$.

$X^2$ is N.

$X^1$, $X^3$ and $X^4$ are each independently C(R2). Preferably, $X^1$, $X^3$ and $X^4$ are each CH.

L1 is $-NH-CH_2-$.

The group $-NH-CH_2-$ may be present in either orientation. Accordingly, the NH moiety in $-NH-CH_2-$ can be bound to the ring moiety containing E, $X^1$ and $X^2$, and the $CH_2$ moiety in $-NH-CH_2-$ can be bound to the group G. Alternatively, the NH moiety in $-NH-CH_2-$ can be bound to the group G, and the $CH_2$ moiety in $-NH-CH_2-$ can be bound to the ring moiety containing E, $X^1$ and $X^2$. Preferably, the NH moiety in $-NH-CH_2-$ is bound to the ring moiety containing E, $X^1$ and $X^2$, and that the $CH_2$ moiety in $-NH-CH_2-$ is bound to the group G.

G is phenyl. As shown in Formula (I), the group G has n substituents R1.

Each R1 is independently chosen from alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each R1 is independently chosen from alkyl, alkynyl, aryl, amino, amido, nitro, halo, haloalkyl, haloalkoxy, cyano, heterocyclyl (e.g., heteroaryl), sulfonyl, sulfonamide, hydroxyl, or alkoxy. More preferably, each R1 is independently chosen from lower alkyl, lower alkynyl, lower aryl, amino, amido, nitro, halo, lower haloalkyl, cyano, heterocyclyl, sulfonyl, sulfonamide, hydroxyl, or alkoxy. Even more preferably, each R1 is independently chosen from $-CF_3$, $-OCH_3$, halo (in particular, $-Cl$), $-CN$, $-CH_3$, $-OH$, ethynyl, or $-C(=O)NH_2$.

Each R2 is independently chosen from $-H$, alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Each R2 group has 1, 2, or 3 independently chosen optional substituents (i.e., each R2 group optionally has 1, 2, or 3 independently chosen substituents as defined below). Furthermore, two R2 groups bound to adjacent carbon atoms (i.e., adjacent ring carbon atoms of the ring moiety comprising E, $X^1$ and $X^2$; the adjacent carbon atoms may thus be $X^1$ and $X^2$ or may be $X^3$ and $X^4$) can be taken together to form a heterocyclyl or aryl group having 1, 2, or 3 independently chosen optional substituents. Said optional substituents (i.e., said optional substituents bound to the R2 group or said optional substituents bound to the heterocyclyl or aryl group formed from two R2 groups bound to adjacent carbon atoms) are each independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonyl, sulfonyl, sulfonamide, urea or carbamate. Preferably, the optional substituents are each independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio.

Preferably, each R2 is independently chosen from $-H$, hydroxyl, haloalkyl, alkoxy, halo, amido, arylalkyl, heterocyclylalkyl, arylalkoxy, or heterocyclylalkoxy, wherein each R2 has 1, 2, or 3 optional substituents (as defined and described herein above). More preferably, each R2 is independently chosen from $-H$, hydroxyl, haloalkyl, alkoxy, halo, amido, arylalkyl, heterocyclylalkyl, arylalkoxy, or heterocyclylalkoxy, wherein each R2 has 1, 2, or 3 optional substituents independently chosen from lower alkyl, lower haloalkyl, lower haloalkoxy, amino(C1-C6)alkyl, halo, lower alkoxy, or amido. Even more preferably, each R2 is independently chosen from $-H$, hydroxyl, haloalkyl, alkoxy, halo, amido, arylalkyl, heterocyclylalkyl, arylalkoxy, or heterocyclylalkoxy, wherein each R2 has 1, 2, or 3 optional substituents independently chosen from chloro, fluoro, $-CH_2NH_2$, $-CH_2CH_2NH_2$, or $-OCH_3$. Even more preferably, each R2 is $-H$.

Each L2 is independently chosen from alkylene or heteroalkylene. Said alkylene is, for example, a (C1-C6)alkylene (including, e.g., methylene, ethylene, propylene, butylene, pentylene, or hexylene), in particular a linear (C1-C6)alkylene. Said heteroalkylene is, for example, chosen from $-CH_2OCH_2-$, $-CH_2SCH_2-$, $-CH_2NHCH_2-$, $-CH_2S-$, or $-CH_2NCH(CH_3)CH_2-$. Preferably, each L2 is independently chosen from (C1-C6)alkylene, more preferably from linear (C1-C6)alkylene.

n is 0, 1, 2, 3, 4 or 5. Preferably, n is 0, 1, 2, 3, or 4. More preferably, n is 0, 1, 2, or 3. Even more preferably, n is 1 or 2. Even more preferably, n is 1.

The invention further relates to the compound of Formula (I) or a pharmaceutically acceptable salt or solvate thereof, as defined in the above described embodiment, for use as a medicament, for use in the treatment or prevention of cancer (such as, e.g., breast cancer, lung cancer, prostate cancer, colorectal cancer, brain cancer, skin cancer, blood cancer, leukemia or lymphoma), for use in the treatment or prevention of a neurological disease or condition (such as, e.g., depression, Alzheimer disease, Huntington disease, Parkinson disease, or Dementia with Lewy Bodies), for use in the treatment or prevention of a viral infection (such as, e.g., a viral infection caused by and/or associated with HIV, or a herpesvirus infection which may be caused by and/or may be associated with a herpesvirus chosen from HSV-1, HSV-2, or Epstein-Barr virus), or for use in treating or preventing viral reactivation after latency (such as, e.g., reactivation of a herpesvirus after latency, or reactivation of a herpesvirus chosen from HSV-1, HSV-2, and Epstein-Barr virus).

In one embodiment, the invention provides a compound of Formula (I) or a pharmaceutically acceptable salt or solvate thereof, wherein the groups E, $X^1$, $X^2$, $X^3$, $X^4$, L1, G, R1, R2, L2, and n have the following meanings.

E is $-X^3=X^4-$.

$X^2$ is N.

$X^1$, $X^3$ and $X^4$ are each independently C(R2). Preferably, $X^1$, $X^3$ and $X^4$ are each CH.

L1 is $-NH-CH_2-$.

The group $-NH-CH_2-$ may be present in either orientation. Accordingly, the NH moiety in $-NH-CH_2-$ can be bound to the ring moiety containing E, $X^1$ and $X^2$, and the $CH_2$ moiety in $-NH-CH_2-$ can be bound to the group G. Alternatively, the NH moiety in $-NH-CH_2-$ can be bound to the group G, and the $CH_2$ moiety in $-NH-CH_2-$ can be bound to the ring moiety containing E, $X^1$ and $X^2$. Preferably, the NH moiety in $-NH-CH_2-$ is bound to the ring moiety containing E, $X^1$ and $X^2$, and that the $CH_2$ moiety in $-NH-CH_2-$ is bound to the group G.

G is a heterocyclyl group. Preferably, G is a heteroaryl group. More preferably, G is selected from thiophenyl, benzothiophenyl, indolyl or indazolyl. Even more preferably, G is indolyl (in particular but without limitation, 1H-indolyl, such as, e.g., 1-H-indol-7-yl) or indazolyl (in particular but without limitation, 1H-indazolyl, such as, e.g., 1H-indazol-7-yl). As shown in Formula (I), the group G has n substituents R1.

Each R1 is independently chosen from alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each R1 is independently chosen from alkyl, alkynyl, aryl, amino, amido, nitro, halo, haloalkyl, haloalkoxy, cyano, heterocyclyl (e.g., heteroaryl), sulfonyl, sulfonamide, hydroxyl, or alkoxy. More preferably, each R1 is independently chosen from lower alkyl, lower alkynyl, lower aryl, amino, amido, nitro, halo, lower haloalkyl, cyano, heterocyclyl, sulfonyl, sulfonamide, hydroxyl, or alkoxy. Even more preferably, each R1 is independently chosen from —$CF_3$, —$OCH_3$, halo (in particular, —Cl), —CN, —$CH_3$, —OH, ethynyl, or —C(=O)$NH_2$.

Each R2 is independently chosen from —H, alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Each R2 group has 1, 2, or 3 independently chosen optional substituents (i.e., each R2 group optionally has 1, 2, or 3 independently chosen substituents as defined below). Furthermore, two R2 groups bound to adjacent carbon atoms (i.e., adjacent ring carbon atoms of the ring moiety comprising E, $X^1$ and $X^2$; the adjacent carbon atoms may thus be $X^1$ and $X^2$ or may be $X^3$ and $X^4$) can be taken together to form a heterocyclyl or aryl group having 1, 2, or 3 independently chosen optional substituents. Said optional substituents (i.e., said optional substituents bound to the R2 group or said optional substituents bound to the heterocyclyl or aryl group formed from two R2 groups bound to adjacent carbon atoms) are each independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfinyl, sulfonyl, sulfonamide, urea or carbamate. Preferably, the optional substituents are each independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio.

Preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents (as defined and described herein above). More preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents independently chosen from lower alkyl, lower haloalkyl, lower haloalkoxy, amino(C1-C6)alkyl, halo, lower alkoxy, or amido. Even more preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents independently chosen from chloro, fluoro, —$CH_2NH_2$, —$CH_2CH_2NH_2$, or —$OCH_3$. Even more preferably, each R2 is —H.

Each L2 is independently chosen from alkylene or heteroalkylene. Said alkylene is, for example, a (C1-C6)alkylene (including, e.g., methylene, ethylene, propylene, butylene, pentylene, or hexylene), in particular a linear (C1-C6)alkylene. Said heteroalkylene is, for example, chosen from —$CH_2OCH_2$—, —$CH_2SCH_2$—, —$CH_2NHCH_2$—, —$CH_2S$—, or —$CH_2NCH(CH_3)CH_2$—. Preferably, each L2 is independently chosen from (C1-C6)alkylene, more preferably from linear (C1-C6)alkylene.

n is 0, 1, 2, 3, 4 or 5. Preferably, n is 0, 1, 2, 3, or 4. More preferably, n is 0, 1, 2, or 3. Even more preferably, n is 1 or 2. Even more preferably, n is 1.

The invention further relates to the compound of Formula (I) or a pharmaceutically acceptable salt or solvate thereof, as defined in the above described embodiment, for use as a medicament, for use in the treatment or prevention of cancer (such as, e.g., breast cancer, lung cancer, prostate cancer, colorectal cancer, brain cancer, skin cancer, blood cancer, leukemia or lymphoma), for use in the treatment or prevention of a neurological disease or condition (such as, e.g., depression, Alzheimer disease, Huntington disease, Parkinson disease, or Dementia with Lewy Bodies), for use in the treatment or prevention of a viral infection (such as, e.g., a viral infection caused by and/or associated with HIV, or a herpesvirus infection which may be caused by and/or may be associated with a herpesvirus chosen from HSV-1, HSV-2, or Epstein-Barr virus), or for use in treating or preventing viral reactivation after latency (such as, e.g., reactivation of a herpesvirus after latency, or reactivation of a herpesvirus chosen from HSV-1, HSV-2, and Epstein-Barr virus).

In one embodiment, the invention provides a compound of Formula (I) or a pharmaceutically acceptable salt or solvate thereof, wherein the groups E, $X^1$, $X^2$, L1, G, R1, R2, R3, L2, and n have the following meanings.

E is —N(R3)-, —S—, or —O—.

R3 is —H or (C1-C6)alkyl. Preferably, R3 is —H or (C1-C4)alkyl. More preferably, R3 is —H, methyl or ethyl. Even more preferably, R3 is —H.

$X^1$ and $X^2$ are each independently C(R2) or N. Preferably, one of $X^1$ and $X^2$ is C(R2) or N, and the other one of $X^1$ and $X^2$ is independently C(R2). More preferably, one of $X^1$ and $X^2$ is CH or N, and Inc other one of $X^1$ and $X^2$ is CH.

L1 is —NH—.

G is phenyl. As shown in Formula (I), the group G has n substituents R1.

Each R1 is independently chosen from alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each R1 is independently chosen from alkyl, alkynyl, aryl, amino, amido, nitro, halo, haloalkyl, haloalkoxy, cyano, heterocyclyl (e.g., heteroaryl), sulfonyl, sulfonamide, hydroxyl, or alkoxy. More preferably, each R1 is independently chosen from lower alkyl, lower alkynyl, lower aryl, amino, amido, nitro, halo, lower haloalkyl, cyano, heterocyclyl, sulfonyl, sulfonamide, hydroxyl, or alkoxy. Even more preferably, each R1 is independently chosen from —$CF_3$, —$OCH_3$, halo (in particular, —Cl), —CN, —$CH_3$, —OH, ethynyl, or —C(=O)$NH_2$.

Each R2 is independently chosen from —H, alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Each R2 group has 1, 2, or 3 independently chosen optional substituents (i.e., each R2 group optionally has 1, 2, or 3 independently chosen substituents as defined below). Furthermore, two R2 groups bound to adjacent carbon atoms (i.e., adjacent ring carbon atoms of the ring moiety comprising E, $X^1$ and $X^2$) can be taken together to form a heterocyclyl or aryl group having 1, 2, or 3 independently chosen optional substituents. Said optional substituents (i.e., said optional substituents bound to the R2 group or said optional substituents bound to the heterocyclyl or aryl group formed from two R2 groups bound to adjacent carbon atoms) are each independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfinyl, sulfonyl, sulfonamide, urea or carbamate. Preferably, the optional substituents are each independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio.

Preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents (as defined and described herein above). More preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents independently chosen from lower alkyl, lower haloalkyl, lower haloalkoxy, amino(C1-C6)alkyl, halo, lower alkoxy, or amido. Even more preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents independently chosen from chloro, fluoro, —CH$_2$NH$_2$, —CH$_2$CH$_2$NH$_2$, or —OCH$_3$. Even more preferably, each R2 is —H.

Each L2 is independently chosen from alkylene or heteroalkylene. Said alkylene is, for example, a (C1-C6)alkylene (including, e.g., methylene, ethylene, propylene, butylene, pentylene, or hexylene), in particular a linear (C1-C6)alkylene. Said heteroalkylene is, for example, chosen from —CH$_2$OCH$_2$—, —CH$_2$SCH$_2$—, —CH$_2$NHCH$_2$—, —CH$_2$S—, or —CH$_2$NCH(CH$_3$)CH$_2$—. Preferably, each L2 is independently chosen from (C1-C6)alkylene, more preferably from linear (C1-C6)alkylene.

n is 0, 1, 2, 3, 4 or 5. Preferably, n is 0, 1, 2, 3, or 4. More preferably, n is 0, 1, 2, or 3. In particular, n may be 0.

The invention further relates to the compound of Formula (I) or a pharmaceutically acceptable salt or solvate thereof, as defined in the above described embodiment, for use as a medicament, for use in the treatment or prevention of cancer (such as, e.g., breast cancer, lung cancer, prostate cancer, colorectal cancer, brain cancer, skin cancer, blood cancer, leukemia or lymphoma), for use in the treatment or prevention of a neurological disease or condition (such as, e.g., depression, Alzheimer disease, Huntington disease, Parkinson disease, or Dementia with Lewy Bodies), for use in the treatment or prevention of a viral infection (such as, e.g., a viral infection caused by and/or associated with HIV, or a herpesvirus infection which may be caused by and/or may be associated with a herpesvirus chosen from HSV-1, HSV-2, or Epstein-Barr virus), or for use in treating or preventing viral reactivation after latency (such as, e.g., reactivation of a herpesvirus after latency, or reactivation of a herpesvirus chosen from HSV-1, HSV-2, and Epstein-Barr virus).

In one embodiment, the invention provides a compound of Formula (I) or a pharmaceutically acceptable salt or solvate thereof, wherein the groups E, $X^1$, $X^2$, L1, G, R1, R2, R3, L2, and n have the following meanings.

E is —N(R3)-, —S—, or —O—.

R3 is —H or (C1-C6)alkyl. Preferably, R3 is —H or (C1-C4)alkyl. More preferably, R3 is —H, methyl or ethyl. Even more preferably, R3 is —H.

$X^1$ and $X^2$ are each independently C(R2) or N. Preferably, one of $X^1$ and $X^2$ is C(R2) or N, and the other one of $X^1$ and $X^2$ is independently C(R2). More preferably, one of $X^1$ and $X^2$ is CH or N, and the other one of $X^1$ and $X^2$ is CH.

L1 is —NH—.

G is a heterocyclyl group. Preferably, G is a heteroaryl group. More preferably, G is selected from thiophenyl, benzothiophenyl, indolyl or indazolyl. Even more preferably, G is indolyl (in particular but without limitation, 1H-indolyl, such as, e.g., 1-H-indol-7-yl) or indazolyl (in particular but without limitation, 1H-indazolyl, such as, e.g., 1H-indazol-7-yl). As shown in Formula (I), the group G has n substituents R1.

Each R1 is independently chosen from alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each R1 is independently chosen from alkyl, alkynyl, aryl, amino, amido, nitro, halo, haloalkyl, haloalkoxy, cyano, heterocyclyl (e.g., heteroaryl), sulfonyl, sulfonamide, hydroxyl, or alkoxy. More preferably, each R1 is independently chosen from lower alkyl, lower alkynyl, lower aryl, amino, amido, nitro, halo, lower haloalkyl, cyano, heterocyclyl, sulfonyl, sulfonamide, hydroxyl, or alkoxy. Even more preferably, each R1 is independently chosen from —CF$_3$, —OCH$_3$, halo (in particular, —Cl), —CN, —CH$_3$, —OH, ethynyl, or —C(=O)NH$_2$.

Each R2 is independently chosen from —H, alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Each R2 group has 1, 2, or 3 independently chosen optional substituents (i.e., each R2 group optionally has 1, 2, or 3 independently chosen substituents as defined below). Furthermore, two R2 groups bound to adjacent carbon atoms (i.e., adjacent ring carbon atoms of the ring moiety comprising E, $X^1$ and $X^2$) can be taken together to form a heterocyclyl or aryl group having 1, 2, or 3 independently chosen optional substituents. Said optional substituents (i.e., said optional substituents bound to the R2 group or said optional substituents bound to the heterocyclyl or aryl group formed from two R2 groups bound to adjacent carbon atoms) are each independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonyl, sulfonyl, sulfonamide, urea or carbamate. Preferably, the optional substituents are each independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio.

Preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents (as defined and described herein above). More preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents independently chosen from lower alkyl, lower haloalkyl, lower haloalkoxy, amino(C1-C6)alkyl, halo, lower alkoxy, or amido. Even more preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents independently chosen from chloro, fluoro, —CH$_2$NH$_2$, —CH$_2$CH$_2$NH$_2$, or —OCH$_3$. Even more preferably, each R2 is —H.

Each L2 is independently chosen from alkylene or heteroalkylene. Said alkylene is, for example, a (C1-C6)alkylene (including, e.g., methylene, ethylene, propylene, butylene, pentylene, or hexylene), in particular a linear (C1-C6)alkylene. Said heteroalkylene is, for example, chosen from —CH$_2$OCH$_2$—, —CH$_2$SCH$_2$—, —CH$_2$NHCH$_2$—, —CH$_2$S—, or —CH$_2$NCH(CH$_3$)CH$_2$—. Preferably, each L2 is independently chosen from (C1-C6)alkylene, more preferably from linear (C1-C6)alkylene.

n is 0, 1, 2, 3, 4 or 5. Preferably, n is 0, 1, 2, 3, or 4. More preferably, n is 0, 1, 2, or 3. In particular, n may be 0.

The invention farther relates to the compound of Formula (I) or a pharmaceutically acceptable salt or solvate thereof, as defined in the above described embodiment, for use as a medicament, for use in the treatment or prevention of cancer (such as, e.g., breast cancer, lung cancer, prostate cancer, colorectal cancer, brain cancer, skin cancer, blood cancer, leukemia or lymphoma), for use in the treatment or prevention of a neurological disease or condition (such as, e.g., depression, Alzheimer disease, Huntington disease, Parkinson disease, or Dementia with Lewy Bodies), for use in the treatment or prevention of a viral infection (such as, e.g., a viral infection caused by and/or associated with HIV, or a herpesvirus infection which may be caused by and/or may be associated with a herpesvirus chosen from HSV-1, HSV-2, or Epstein-Barr virus), or for use in treating or preventing viral reactivation after latency (such as, e.g., reactivation of a herpesvirus after latency, or reactivation of a herpesvirus chosen from HSV-1, HSV-2, and Epstein-Barr virus).

In one embodiment, the invention provides a compound of Formula (I) or a pharmaceutically acceptable salt or solvate thereof, wherein the groups E, X', X$^2$, L1, G, R1, R2, R3, L2, and n have the following meanings.

E is —N(R3)-, —S—, or —O—.

R3 is —H or (C1-C6)alkyl. Preferably, R3 is —H or (C1-C4)alkyl. More preferably, R3 is —H, methyl or ethyl. Even more preferably, R3 is —H.

X$^1$ and X$^2$ are each independently C(R2) or N. Preferably, one of X$^1$ and X$^2$ is C(R2) or N, and the other one of X$^1$ and X$^2$ is independently C(R2). More preferably, one of X$^1$ and X$^2$ is CH or N, and the other one of X$^1$ and X$^2$ is CH.

L1 is —NH—CH$_2$—.

The group —NH—CH$_2$— may be present in either orientation. Accordingly, the NH moiety in —NH—CH$_2$— can be bound to the ring moiety containing E, X$^1$ and X$^2$, and the CH$_2$ moiety in —NH—CH$_2$— can be bound to the group G. Alternatively, the NH moiety in —NH—CH$_2$— can be bound to the group G, and the CH$_2$ moiety in —NH—CH$_2$— can be bound to the ring moiety containing E, X$^1$ and X$^2$. Preferably, the NH moiety in —NH—CH$_2$— is bound to the ring moiety containing E, X$^1$ and X$^2$, and that the CH$_2$ moiety in —NH—CH$_2$— is bound to the group G.

G is phenyl. As shown in Formula (I), the group G has n substituents R1.

Each R1 is independently chosen from alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each R1 is independently chosen from alkyl, alkynyl, aryl, amino, amido, nitro, halo, haloalkyl, haloalkoxy, cyano, heterocyclyl (e.g., heteroaryl), sulfonyl, sulfonamide, hydroxyl, or alkoxy. More preferably, each R1 is independently chosen from lower alkyl, lower alkynyl, lower aryl, amino, amido, nitro, halo, lower haloalkyl, cyano, heterocyclyl, sulfonyl, sulfonamide, hydroxyl, or alkoxy. Even more preferably, each R1 is independently chosen from —CF$_3$, —OCH$_3$, halo (in particular, —Cl), —CN, —CH$_3$, —OH, ethynyl, or —C(=O)NH$_2$.

Each R2 is independently chosen from —H, alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Each R2 group has 1, 2, or 3 independently chosen optional substituents (i.e., each R2 group optionally has 1, 2, or 3 independently chosen substituents as defined below). Furthermore, two R2 groups bound to adjacent carbon atoms (i.e., adjacent ring carbon atoms of the ring moiety comprising E, X$^1$ and X$^2$) can be taken together to form a heterocyclyl or aryl group having 1, 2, or 3 independently chosen optional substituents. Said optional substituents (i.e., said optional substituents bound to the R2 group or said optional substituents bound to the heterocyclyl or aryl group formed from two R2 groups bound to adjacent carbon atoms) are each independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfinyl, sulfonyl, sulfonamide, urea or carbamate. Preferably, the optional substituents are each independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio.

Preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents (as defined and described herein above). More preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents independently chosen from lower alkyl, lower haloalkyl, lower haloalkoxy, amino(C1-C6)alkyl, halo, lower alkoxy, or amido. Even more preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents independently chosen from chloro, fluoro, —CH$_2$NH$_2$, —CH$_2$CH$_2$NH$_2$, or —OCH$_3$. Even more preferably, each R2 is —H.

Each L2 is independently chosen from alkylene or heteroalkylene. Said alkylene is, for example, a (C1-C6)alkylene (including, e.g., methylene, ethylene, propylene, butylene, pentylene, or hexylene), in particular a linear (C1-C6)alkylene. Said heteroalkylene is, for example, chosen from —CH$_2$OCH$_2$—, —CH$_2$SCH$_2$—, —CH$_2$NHCH$_2$—, —CH$_2$S—, or CH$_2$NCH(CH$_3$)CH$_2$—. Preferably, each L2 is independently chosen from (C1-C6)alkylene, more preferably from linear (C1-C6)alkylene.

n is 0, 1, 2, 3, 4 or 5. Preferably, n is 0, 1, 2, 3, or 4. More preferably, n is 0, 1, 2, or 3. In particular, n may be 0.

The invention further relates to the compound of Formula (I) or a pharmaceutically acceptable salt or solvate thereof, as defined in the above described embodiment, for use as a medicament, for use in the treatment or prevention of cancer (such as, e.g., breast cancer, lung cancer, prostate cancer, colorectal cancer, brain cancer, skin cancer, blood cancer, leukemia or lymphoma), for use in the treatment or prevention of a neurological disease or condition (such as, e.g., depression, Alzheimer disease, Huntington disease, Parkinson disease, or Dementia with Lewy Bodies), for use in the treatment or prevention of a viral infection (such as, e.g., a viral infection caused by and/or associated with HIV, or a herpesvirus infection which may be caused by and/or may be associated with a herpesvirus chosen from HSV-1, HSV-2, or Epstein-Barr virus), or for use in treating or preventing viral reactivation after latency (such as, e.g., reactivation of a herpesvirus after latency, or reactivation of a herpesvirus chosen from HSV-1, HSV-2, and Epstein-Ban virus).

In one embodiment, the invention provides a compound of Formula (I) or a pharmaceutically acceptable salt or solvate thereof, wherein the groups E, $X^1$, $X^2$, L1, G, R1, R2, R3, L2, and n have the following meanings.

E is —N(R3)-, —S—, or —O—.

R3 is —H or (C1-C6)alkyl. Preferably, R3 is —H or (C1-C4)alkyl. More preferably, R3 is —H, methyl or ethyl. Even more preferably, R3 is —H.

$X^1$ and $X^2$ are each independently C(R2) or N. Preferably, one of $X^1$ and $X^2$ is C(R2) or N, and the other one of $X^1$ and $X^2$ is independently C(R2). More preferably, one of $X^1$ and $X^2$ is CH or N, and the other one of $X^1$ and $X^2$ is CH.

L1 is —NH—CH$_2$—.

The group —NH—CH$_2$— may be present in either orientation. Accordingly, the NH moiety in —NH—CH$_2$— can be bound to the ring moiety containing E, $X^1$ and $X^2$, and the CH$_2$ moiety in —NH—CH$_2$— can be bound to the group G. Alternatively, the NH moiety in —NH—CH$_2$— can be bound to the group G, and the CH$_2$ moiety in —NH—CH$_2$— can be bound to the ring moiety containing E, $X^1$ and $X^2$. Preferably, the NH moiety in —NH—CH$_2$— is bound to the ring moiety containing E, $X^1$ and $X^2$, and that the CH$_2$ moiety in —NH—CH$_2$— is bound to the group G.

G is a heterocyclyl group. Preferably, G is a heteroaryl group. More preferably, G is selected from thiophenyl, benzothiophenyl, indolyl or indazolyl. Even more preferably, G is indolyl (in particular but without limitation, 1H-indolyl, such as, e.g., 1-H-indol-7-yl) or indazolyl (in particular but without limitation, 1H-indazolyl, such as, e.g., 1H-indazol-7-yl). As shown in Formula (I), the group G has n substituents R1.

Each R1 is independently chosen from alkyl, alkenyl, alkynyl, cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Preferably, each R1 is independently chosen from alkyl, alkynyl, aryl, amino, amido, nitro, halo, haloalkyl, haloalkoxy, cyano, heterocyclyl (e.g., heteroaryl), sulfonyl, sulfonamide, hydroxyl, or alkoxy. More preferably, each R1 is independently chosen from lower alkyl, lower alkynyl, lower aryl, amino, amido, nitro, halo, lower haloalkyl, cyano, heterocyclyl, sulfonyl, sulfonamide, hydroxyl, or alkoxy. Even more preferably, each R1 is independently chosen from —CF$_3$, —OCH$_3$, halo (in particular, —Cl), —CN, —CH$_3$, —OH, ethynyl, or —C(=O)NH$_2$.

Each R2 is independently chosen from —H, alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl. Each R2 group has 1, 2, or 3 independently chosen optional substituents (i.e., each R2 group optionally has 1, 2, or 3 independently chosen substituents as defined below). Furthermore, two R2 groups bound to adjacent carbon atoms (i.e., adjacent ring carbon atoms of the ring moiety comprising E, $X^1$ and $X^2$) can be taken together to form a heterocyclyl or aryl group having 1, 2, or 3 independently chosen optional substituents. Said optional substituents (i.e., said optional substituents bound to the R2 group or said optional substituents bound to the heterocyclyl or aryl group formed from two R2 groups bound to adjacent carbon atoms) are each independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonyl, sulfonamide, urea or carbamate. Preferably, the optional substituents are each independently chosen from lower alkyl, lower alkanoyl, lower heteroalkyl, lower heterocyclyl, lower haloalkyl, lower cycloalkyl, lower carbocyclyl, arylalkoxy, heterocyclylalkoxy, aryl, aryloxy, heterocyclyloxy, lower alkoxy, lower haloalkoxy, oxo, lower acyloxy, carbonyl, carboxyl, lower carboxamido, cyano, halogen, hydroxyl, amino, aminoalkyl, amidoalkyl, amido, nitro, thiol, lower alkylthio, or arylthio.

Preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents (as defined and described herein above). More preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents independently chosen from lower alkyl, lower haloalkyl, lower haloalkoxy, amino(C1-C6)alkyl, halo, lower alkoxy, or amido. Even more preferably, each R2 is independently chosen from —H, hydroxyl, haloalkyl, alkoxy, halo, amido, arylalkyl, heterocyclylalkyl, arylalkoxy, or heterocyclylalkoxy, wherein each R2 has 1, 2, or 3 optional substituents independently chosen from chloro, fluoro, —CH$_2$NH$_2$, —CH$_2$CH$_2$NH$_2$, or —OCH$_3$. Even more preferably, each R2 is —H.

Each L2 is independently chosen from alkylene or heteroalkylene. Said alkylene is, for example, a (C1-C6)alkylene (including, e.g., methylene, ethylene, propylene, butylene, pentylene, or hexylene), in particular a linear (C1-C6)alkylene. Said heteroalkylene is, for example, chosen from —CH$_2$OCH$_2$—, —CH$_2$SCH$_2$—, —CH$_2$NHCH$_2$—, —CH$_2$S—, or CH$_2$NCH(CH$_3$)CH$_2$—. Preferably, each L2 is independently chosen from (C1-C6)alkylene, more preferably from linear (C1-C6)alkylene.

n is 0, 1, 2, 3, 4 or 5. Preferably, n is 0, 1, 2, 3, or 4. More preferably, n is 0, 1, 2, or 3. In particular, n may be 0.

The invention further relates to the compound of Formula (I) or a pharmaceutically acceptable salt or solvate thereof, as defined in the above described embodiment, for use as a medicament, for use in the treatment or prevention of cancer (such as, e.g., breast cancer, lung cancer, prostate cancer, colorectal cancer, brain cancer, skin cancer, blood cancer, leukemia or lymphoma), for use in the treatment or prevention of a neurological disease or condition (such as, e.g., depression, Alzheimer disease, Huntington disease, Parkinson disease, or Dementia with Lewy Bodies), for use in the treatment or prevention of a viral infection (such as, e.g., a viral infection caused by and/or associated with HIV, or a herpesvirus infection which may be caused by and/or may be associated with a herpesvirus chosen from HSV-1, HSV-2, or Epstein-Barr virus), or for use in treating or preventing viral reactivation after latency (such as, e.g., reactivation of a herpesvirus after latency, or reactivation of a herpesvirus chosen from HSV-1, HSV-2, and Epstein-Barr virus).

In one preferred embodiment, the invention provides a compound of Formula (I) or a pharmaceutically acceptable salt or solvate thereof, wherein:

E is $-X^3=X^4-$.

$X^1$ is N.

$X^2$, $X^3$ and $X^4$ are each CH.

L 1 is —NH— or —NH—$CH_2$—.

G is a substituted phenyl with one substituent R1, or G is indolyl or indazolyl.

R1 is independently chosen from lower alkyl, lower alkynyl, lower aryl, amino, amido, nitro, halo, lower haloalkyl, cyano, heterocyclyl, sulfonyl, sulfonamide, hydroxyl, or alkoxy. Preferably, R1 is $-CF_3$, $-OCH_3$, halo (in particular, —Cl), —CN, $-CH_3$, —OH, ethynyl, or $-C(=O)NH_2$.

In another preferred embodiment, the invention provides a compound of Formula (I) or a pharmaceutically acceptable salt or solvate thereof, wherein:

E is $-X^3=X^4-$.

$X^1$ is N or CH.

$X^2$, $X^3$ and $X^4$ are each CH.

L1 is —NH— or —NH—$CH_2$—.

G is a substituted phenyl with one substituent R1, or G is indolyl or indazolyl.

R1 is independently chosen from lower alkyl, lower alkynyl, lower aryl, amino, amido, nitro, halo, lower haloalkyl, cyano, heterocyclyl, sulfonyl, sulfonamide, hydroxyl, or alkoxy.

Preferably, R1 is $-CF_3$, $-OCH_3$, halo (in articular, —Cl), —CN, $-CH_3$, —OH, ethynyl, or $-C(=O)NH_2$.

The invention further relates to the compound of Formula (I) or a pharmaceutically acceptable salt or solvate thereof, as defined in the above described embodiment, for use as a medicament, for use in the treatment or prevention of cancer (such as, e.g., breast cancer, lung cancer, prostate cancer, colorectal cancer, brain cancer, skin cancer, blood cancer, leukemia or lymphoma), for use in the treatment or prevention of a neurological disease or condition (such as, e.g., depression, Alzheimer disease, Huntington disease, Parkinson disease, or Dementia with Lewy Bodies), for use in the treatment or prevention of a viral infection (such as, e.g., a viral infection caused by and/or associated with HIV, or a herpesvirus infection which may be caused by and/or may be associated with a herpesvirus chosen from HSV-1, HSV-2, or Epstein-Barr virus) or for use in treating or preventing viral reactivation after latency (such as, e.g., reactivation of a herpesvirus after latency, or reactivation of a herpesvirus chosen from HSV-1, HSV-2, and Epstein-Barr virus).

In one aspect, the invention provides a stereoisomer or a mixture thereof, of a compound of Formula (I).

In another aspect, the invention relates to a derivative or analog of a compound of Formula (I).

In yet another aspect, the invention relates to a solvate or polymorph of a compound of Formula (I).

In another aspect, the invention relates to a salt of a compound of formula (I).

In yet another aspect, the invention relates to a prodrug of a compound of Formula (I).

In yet another aspect, the invention relates to a metabolite of a compound of Formula (I).

In another aspect, the invention provides a method of treating or preventing a disease or condition comprising administering, to a patient (preferably, a human) in need of such treatment or prevention, a therapeutically effective amount of a pharmaceutical composition comprising a compound of Formula (I) as defined above, or a pharmaceutically acceptable salt or solvate thereof and a pharmaceutically acceptable carrier. This aspect can be reformulated as a compound of Formula (I) or a pharmaceutically acceptable salt or solvate thereof for use as a medicine. In a related aspect, the invention provides a pharmaceutical composition for use in treating or preventing a disease or condition wherein said composition comprises a therapeutically effective amount of a compound of Formula (I) sufficient for treating or preventing said disease or condition. In a more specific embodiment the invention provides a compound of Formula (I) for use in the treatment or prevention of a disease associated with LSD1. In another preferred aspect, the therapeutically effective amount of a compound of Formula (I) is an amount sufficient to modulate the level of histone-3 lysine-4 methylation. In another preferred aspect, the therapeutically effective amount of a compound of Formula (I) is an amount sufficient to modulate the level of histone-3 lysine-9 methylation. In another preferred aspect, the therapeutically effective amount of a compound of Formula (I) is an amount sufficient to modulate the level gene expression.

In yet another aspect, the invention provides a pharmaceutical composition comprising a compound of Formula (I) and a pharmaceutically acceptable carrier. In a more specific aspect, the pharmaceutical composition comprises a therapeutically effective amount of a compound of Formula (I). In an even more specific aspect, the therapeutically effective amount of a compound of Formula (I) is an amount effective to inhibit LSD1. In another preferred aspect, the therapeutically effective amount of a compound of Formula (I) is an amount sufficient to modulate the level of histone-3 lysine-4 methylation. In another preferred aspect, the therapeutically effective amount of a compound of Formula (I) is an amount sufficient to modulate the level of histone-3 lysine-9 methylation. In another preferred aspect, the therapeutically effective amount of a compound of Formula (I) is an amount sufficient to modulate the level gene expression.

In again another aspect, the invention provides a method of inhibiting LSD1 activity comprising administering, to a patient in need of treatment, a therapeutically effective amount of a composition comprising a compound of Formula (I) or a pharmaceutically acceptable salt thereof, and a pharmaceutically acceptable carrier sufficient to inhibit LSD1 activity. This aspect can be reformulated as a compound of Formula (I) as herein defined for use as a LSD1 inhibitor. This aspect can also be reformulated as the use of a compound of Formula (I) for the manufacture of a medicament for the treatment or prevention of a disease associated with LSD1. In a related aspect, a method for treating or preventing an individual is provided, said method comprising identifying an individual in need of treatment or prevention and administering to said individual a therapeutically effective amount of a compound of Formula (I). In a preferred aspect, the therapeutically effective amount of a compound of Formula (I) is an amount sufficient to inhibit LSD1. In another preferred aspect, the therapeutically effective amount of a compound of Formula (I) is an amount sufficient to modulate the level of histone-3 lysine-4 methylation. In another preferred aspect, the therapeutically effective amount of a compound of Formula (I) is an amount sufficient to modulate the level of histone-3 lysine-9 methylation. In another preferred aspect, the therapeutically effective amount of a compound of Formula (I) is an amount sufficient to modulate the level gene expression.

Preferred embodiments of the compounds of Formula (I) for use in the composition and method of these aspects of the invention are as defined herein above in the first aspect of the invention.

In still another aspect, the invention provides a method of treating or preventing cancer comprising administering, to a patient in need of such treatment or prevention, a therapeutically effective amount of a pharmaceutical composition comprising a compound of Formula (I) as defined above in the first aspect of the invention, and a pharmaceutically acceptable carrier. This aspect can be reformulated as a compound of Formula (I) as defined above for use in the treatment or prevention of cancer. In a related aspect, the invention provides a pharmaceutical composition for use in treating or preventing cancer wherein said composition comprises a therapeutically effective amount of a compound of Formula (I) sufficient for treating or preventing cancer. In another related aspect, the invention provides a compound of Formula (I) or a pharmaceutical composition for use in the treatment or prevention of cancer, wherein said cancer is chosen from testicular cancer, breast cancer, lung cancer, prostate cancer, colorectal cancer, brain cancer, skin cancer, blood cancer (e.g., leukemia) and lymphoma, wherein said composition comprises a therapeutically effective amount of a compound of Formula (I) sufficient for treating or preventing the said cancer. In a preferred aspect, the therapeutically effective amount of a compound of Formula (I) is an amount sufficient to inhibit LSD1. In another preferred aspect, the therapeutically effective amount of a compound of Formula (I) is an amount sufficient to modulate the level of histone 3 lysine 4 methylation. In another preferred aspect, the therapeutically effective amount of a compound of Formula (I) is an amount sufficient to the level of modulate histone 3 lysine 9 methylation. In another preferred aspect, the therapeutically effective amount of a compound of Formula (I) is an amount sufficient to modulate the level gene expression.

In another preferred embodiment, a therapeutically effective amount of the pharmaceutical composition is administered to an individual in an amount sufficient to prevent or treat a disease. In a more specific aspect, the disease is cancer. In an even more specific aspect, the disease is a cancer chosen from prostate cancer, testicular cancer, brain cancer, colorectal cancer, lung cancer, breast cancer, skin cancer, and blood cancer.

Recent studies have implicated LSD1 in viral infection and reactivation. In particular it was shown that pharmacological inhibitors of LSD1 like parnate and siRNA knock down of LSD1 caused reduced viral infectivity and reduced reactivation after latency (Liang et al. (2009) *Nat. Med.* 15:1312-1317). Therefore it is believed that the compounds of the invention can be used for treating or preventing viral infection. Furthermore, it is believed that the compounds of the invention can treat or prevent viral reactivation after latency.

Thus, in another aspect, the invention provides a method for treating or preventing a viral infection, the method comprising administering to an individual (preferably a human) a compound of Formula (I) as defined above in any of the aspects and embodiments of the invention or a pharmaceutically acceptable salt or solvate thereof. Accordingly, the invention also provides a compound of Formula (I) as defined above in any of the aspects and embodiments of the invention or a pharmaceutically acceptable salt or solvate thereof for use in treating or preventing a viral infection. In one specific embodiment, the viral infection is a herpesvirus infection. In a more specific embodiment, the herpesvirus infection is caused by and/or associated with a herpesvirus chosen from HSV-1, HSV-2, and Epstein-Barr virus. In another embodiment of this seventh aspect, the viral infection is caused by and/or associated with HIV. In even more specific embodiment, the invention provides a method for treating or preventing viral reactivation after latency, the method comprising administering to an individual refer ably a human) a compound of Formula (I) as defined above in any of the aspects and embodiments of the invention or a pharmaceutically acceptable salt or solvate thereof. Accordingly, the invention also provides a compound of Formula (I) as defined above in any of the aspects and embodiments of the invention or a pharmaceutically acceptable salt or solvate thereof for use in treating or preventing viral reactivation after latency. In a specific embodiment, the virus that is reactivating is a herpesvirus. In a more specific embodiment, the herpesvirus that is reactivating is chosen from HSV-1, HSV-2, and Epstein-Barr virus. In an even more specific embodiment, the virus that is reactivating is HSV.

In one embodiment the invention provides a compound Formula (I) or a pharmaceutically acceptable salt or solvate thereof, wherein the compound is chosen from:

5-((trans)-2-aminocyclopropyl)-N-(3-chlorophenyl)pyridin-2-amine;
5-((trans)-2-aminocyclopropyl)-N-(4-chlorophenyl)pyridin-2-amine;
5-((trans)-2-aminocyclopropyl)-N-(4-(trifluoromethyl)phenyl)pyridin-2-amine;
5-((trans)-2-aminocyclopropyl)-N-(3-methoxyphenyl)pyridin-2-amine;
5-((trans)-2-aminocyclopropyl)-N-(4-methoxyphenyl)pyridin-2-amine;
5-((trans)-2-aminocyclopropyl)-N-p-tolylpyridin-2-amine;
5-((trans)-2-aminocyclopropyl)-N-m-tolylpyridin-2-amine;
4-(5-((trans)-2-aminocyclopropyl)pyridin-2-ylamino)benzonitrile;
3-(5-((trans)-2-aminocyclopropyl)pyridin-2-ylamino)benzonitrile;
3-(5-((trans)-2-aminocyclopropyl)pyridin-2-ylamino)benzamide;
4-(5-((trans)-2-aminocyclopropyl)pyridin-2-ylamino)benzamide;
5-((trans)-2-aminocyclopropyl)-N-(3-chlorobenzyl)pyridin-2-amine;
5-((trans)-2-aminocyclopropyl)-N-(4-chlorobenzyl)pyridin-2-amine;
5-((trans)-2-aminocyclopropyl)-N-(3-(trifluoromethyl)benzyl)pyridin-2-amine;
5-((trans)-2-aminocyclopropyl)-N-(4-(trifluoromethyl)benzyl)pyridin-2-amine;
5-((trans)-2-aminocyclopropyl)-N-(3-methylbenzyl)pyridin-2-amine;
5-((trans)-2-aminocyclopropyl)-N-(4-methylbenzyl)pyridin-2-amine;
3-((5-((trans)-2-aminocyclopropyl)pyridin-2-ylamino)methyl)benzonitrile;
4-((5-((trans)-2-aminocyclopropyl)pyridin-2-ylamino)methyl)benzonitrile;
5-((trans)-2-aminocyclopropyl)-N-(3-methoxybenzyl)pyridin-2-amine;

5-((trans)-2-aminocyclopropyl)-N-(4-methoxybenzyl)pyridin-2-amine;
4-(5-((trans)-2-aminocyclopropyl)pyridin-2-ylamino)phenol;
3-((5-((trans)-2-aminocyclopropyl)pyridin-2-ylamino)methyl)benzamide;
4-((5-((trans)-2-aminocyclopropyl)pyridin-2-ylamino)methyl)benzamide;
4-((5-((trans)-2-aminocyclopropyl)pyridin-2-ylamino)methyl)phenol;
5-((trans)-2-aminocyclopropyl)-N-(3-ethynylphenyl)pyridin-2-amine;
N-(5-((trans)-2-aminocyclopropyl)pyridin-2-yl)-1H-indol-7-amine;
N-(5-((trans)-2-aminocyclopropyl)pyridin-2-yl)-1H-indazol-7-amine; or
3-(5-((trans)-2-aminocyclopropyl)pyridin-2-ylamino)phenol.

In another embodiment the invention provides a compound Formula (I) or a pharmaceutically acceptable salt or solvate thereof, wherein the compound is chosen from:
5-((trans)-2-aminocyclopropyl)-N-(3-chlorophenyl)pyridin-2-amine;
5-((trans)-2-aminocyclopropyl)-N-(4-chlorophenyl)pyridin-2-amine;
5-((trans)-2-aminocyclopropyl)-N-(4-(trifluoromethyl)phenyl)pyridin-2-amine;
5-((trans)-2-aminocyclopropyl)-N-(3-methoxyphenyl)pyridin-2-amine;
5-((trans)-2-aminocyclopropyl)-N-(4-methoxyphenyl)pyridin-2-amine;
5-((trans)-2-aminocyclopropyl)-N-p-tolylpyridin-2-amine;
5-((trans)-2-aminocyclopropyl)-N-m-tolylpyridin-2-amine;
4-(5-((trans)-2-aminocyclopropyl)pyridin-2-ylamino)benzonitrile;
3-(5-((trans)-2-aminocyclopropyl)pyridin-2-ylamino)benzonitrile;
3-(5-((trans)-2-aminocyclopropyl)pyridin-2-ylamino)benzamide;
4-(5-((trans)-2-aminocyclopropyl)pyridin-2-ylamino)benzamide;
5-((trans)-2-aminocyclopropyl)-N-(3-chlorobenzyl)pyridin-2-amine;
5-((trans)-2-aminocyclopropyl)-N-(4-chlorobenzyl)pyridin-2-amine;
5-((trans)-2-aminocyclopropyl)-N-(3-(trifluoromethyl)benzyl)pyridin-2-amine;
5-((trans)-2-aminocyclopropyl)-N-(4-(trifluoromethyl)benzyl)pyridin-2-amine;
5-((trans)-2-aminocyclopropyl)-N-(3-methylbenzyl)pyridin-2-amine;
5-((trans)-2-aminocyclopropyl)-N-(4-methylbenzyl)pyridin-2-amine;
3-((5-((trans)-2-aminocyclopropyl)pyridin-2-ylamino)methyl)benzonitrile;
4-((5-((trans)-2-aminocyclopropyl)pyridin-2-ylamino)methyl)benzonitrile;
5-((trans)-2-aminocyclopropyl)-N-(3-methoxybenzyl)pyridin-2-amine;
5-((trans)-2-aminocyclopropyl)-N-(4-methoxybenzyl)pyridin-2-amine;
4-(5-((trans)-2-aminocyclopropyl)pyridin-2-ylamino)phenol;
3-(5-((trans)-2-aminocyclopropyl)pyridin-2-ylamino)methyl)benzamide;
4-((5-((trans)-2-aminocyclopropyl)pyridin-2-ylamino)methyl)benzamide;
4-((5-((trans)-2-aminocyclopropyl)pyridin-2-ylamino)methyl)phenol;
5-((trans)-2-aminocyclopropyl)-N-(3-ethynylphenyl)pyridin-2-amine;
N-(5-((trans)-2-aminocyclopropyl)pyridin-2-yl)-1H-indol-7-amine;
N-(5-((trans)-2-aminocyclopropyl)pyridin-2-yl)-1H-indazol-7-amine;
3-(5-((trans)-2-aminocyclopropyl)pyridin-2-ylamino)phenol;
4-((trans)-2-aminocyclopropyl)-N-(4-methylbenzyl)aniline;
4-((trans)-2-aminocyclopropyl)-N-(4-(trifluoromethyl)benzyl)aniline;
4-((trans)-2-aminocyclopropyl)-N-(3-chlorobenzyl)aniline;
3-((4-((trans)-2-aminocyclopropyl)phenyl)amino)methyl)benzonitrile;
4-((trans)-2-aminocyclopropyl)-N-(p-tolyl)aniline;
4-((trans)-2-aminocyclopropyl)-N-(4-chlorophenyl)aniline;
3-((4-((trans)-2-aminocyclopropyl)phenyl)amino)benzonitrile;
N-(4-((trans)-2-aminocyclopropyl)phenyl)-3-methoxyaniline; or
3-((4-((trans)-2-aminocyclopropyl)phenyl)amino)benzamide.

Definitions

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

As used herein, the term "acyl," refers to a carbonyl attached to an alkenyl, alkyl, aryl, cycloalkyl, heteroaryl, heterocyclyl, or any other moiety where the atom attached to the carbonyl is carbon. An "acetyl" group refers to a —C(=O)CH$_3$ group. An "alkylcarbonyl" or "alkanoyl" group refers to an alkyl group attached to the parent molecular moiety through a carbonyl group. Examples of such groups include, but are not limited to, methylcarbonyl or ethylcarbonyl. Examples of acyl groups include, but are not limited to, formyl, alkanoyl or aroyl.

As used herein, the term "acyloxy," refers to an acyl group attached to the parent moiety through an oxygen atom.

As used herein, the term "alkenyl," refers to a straight-chain or branched-chain hydrocarbon group having one or more double bonds and containing from 2 to 20 carbon atoms. A (C2-C6)alkenyl has from 2 to 6 carbon atoms. Examples of suitable alkenyl groups include, but are not limited to, ethenyl, propenyl, 2-methylpropenyl, or 1,3-butadienyl.

As used herein, the term "alkenylene," refers to a carbon-carbon double bond system attached at two or more positions such as ethenylene e.g., —CH=CH—. Alkenylene groups include, but are not limited to, (C2-C20)alkenylene groups, such as, e.g., ethenylene, propenylene, 2-methylpropenylene, or 1,3-butadienylene.

As used herein, the term "alkoxy," refers to an alkyl ether group, wherein the term alkyl is as defined below. Examples of suitable alkyl ether groups include, but are not limited to, methoxy, ethoxy, n-propoxy, isopropoxy, n-butoxy, iso-butoxy, sec-butoxy, tert-butoxy, or n-pentoxy.

As used herein, the term "alkyl," refers to a straight-chain or branched-chain alkyl group containing from 1 to 20 carbon atoms. A (C1-C10)alkyl has from 1 to 10 carbon atoms and a (C1-C6)alkyl has from 1 to 6 carbon atoms and a (C1-C4)alkyl has from 1 to 4 carbon atoms. Examples of alkyl groups include, but are not limited to, methyl, ethyl, n-propyl, isopropyl, n-butyl, isobutyl, sec-butyl, tert-butyl, pentyl, isopentyl, neo-pentyl, iso-amyl, hexyl, heptyl, octyl, or nonyl.

As used herein, the term "alkylene," refers to a saturated aliphatic group derived from a straight or branched chain saturated hydrocarbon attached at two or more positions. Alkylene groups include, but are not limited to, (C1-C20) alkylene groups, such as, e.g., methylene (—$CH_2$—), ethylene (—$CH_2CH_2$—), propylene (—$CH_2CH_2CH_2$—) or isopropylene (—$CH(CH_3)CH_2$—).

As used herein, the term "alkylamino," refers to an alkyl group as defined herein which is attached to the parent molecular moiety through an amino group. Suitable alkylamino groups may be mono- or dialkylated. Exemplary alkylamino groups include, but are not limited to, N-methylamino, N-ethylamino, N,N-dimethylamino, N,N-ethylmethylamino, N,N-diethylamino, N-propylamino, or N,N-methylpropylamino.

As used herein, the term "alkylidene," refers to an alkenyl group in which one carbon atom of the carbon-carbon double bond belongs to the moiety to which the alkenyl group is attached.

As used herein, the term "alkylthio," refers to an alkyl thioether (R—S—) group wherein the term R is an alkyl is as defined above wherein the group is attached to the parent molecule through the sulfur group. Examples of suitable alkyl thioether groups include, but are not limited to, methylthio, ethylthio, n-propylthio, isopropylthio, n-butylthio, iso-butylthio, sec-butylthio, or tert-butylthio.

As used herein, the term "alkynyl," refers to a straight-chain or branched-chain hydrocarbon group having one or more triple bonds and containing from 2 to 20 carbon atoms. A (C2-C6)alkynyl has from 2 to 6 carbon atoms. A (C2-C4) alkynyl has from 2 to 4 carbon atoms. Examples of alkynyl groups include, but are not limited to, ethynyl, propynyl, butyn-1-yl, Butyn-2-yl, pentyn-1-yl, 3-methylbutyn-1-yl, or hexyn-2-yl.

As used herein, the term "alkynylene," refers to a carbon-carbon triple bond attached at two positions such as ethynylene (—C≡C—). Alkynylene groups include, but are not limited to, (C2-C20)alkynylene groups, such as, e.g., ethynylene or propynylene, As used herein, the terms "amido" and "carbamoyl," refer to an amino group as described below attached to the parent molecular moiety through a carbonyl group (e.g., —C(═O) NR R'), or vice versa (—N(R)C(═O)NR'). "Amido" and "carbamoyl" encompass "C-amido", "N-amido" and "acylamino" as defined herein. R and R' are as defined herein.

As used herein, the term "C-amido," refers to a —C(═O) NRR' group with R and R' as defined herein.

As used herein, the term "N-amido," refers to a R'C(═O) NR— group, with R and R' as defined herein.

As used herein, the term "acylamino," refers to an acyl group attached to the parent moiety through an amino group. An example of an "acylamino" group includes, but is not limited to, acetylamino ($CH_3C$(═O)NH—).

As used herein, the term "amino," refers to —NRR', wherein R and R' are independently selected from the group consisting of hydrogen, alkyl, heteroalkyl, aryl, carbocyclyl, and heterocyclyl. Additionally, R and R' may be combined to form a heterocyclyl.

As used herein, the term "aryl," refers a carbocyclic aromatic system containing one ring, or two or three rings fused together where in the ring atoms are all carbon. The term "aryl" groups includes, but is not limited to groups such as phenyl, naphthyl, or anthracenyl.

As used herein, the term "arylalkenyl" or "aralkenyl," refers to an aryl group attached to the parent molecular moiety through an alkenyl group.

As used herein, the term "arylalkoxy" or "aralkoxy," refers to an aryl group attached to the parent molecular moiety through an alkoxy group. Examples of arylalkoxy groups include, but are not limited to, benzyloxy or phenethoxy.

As used herein, the term "arylalkyl" or "aralkyl," refers to an aryl group attached to the parent molecular moiety through an alkyl group.

As used herein, the term "arylalkynyl" or "aralkynyl," refers to an aryl group attached to the parent molecular moiety through an alkynyl group.

As used herein, the term "arylalkanoyl" or "aralkanoyl" or "aroyl," refers to an acyl group derived from an aryl-substituted alkanecarboxylic acid including, but not limited to, benzoyl, napthoyl, phenylacetyl, 3-phenylpropionyl (hydrocinnamoyl), 4-phenylbutyryl, (2-naphthyl)acetyl, or 4-chlorohydrocinnamoyl.

As used herein, the term "aryloxy," refers to an aryl group attached to the parent molecular moiety through an oxy (—O—).

As used herein, the terms "benzo" and "bent," refer to the divalent group $C_6H_4$=derived from benzene. Examples include, but are not limited to, benzothiophene or benzimidazole.

As used herein, the term "carbamate," refers to an O-carbamyl or N-carbamyl group as defined herein.

As used herein, the term "O-carbamyl" refers to a —OC (═O)NRR', group-with R and R' as defined herein.

As used herein, the term "N-carbamyl" refers to a ROC (═O)NR'— group, with R and R' as defined herein.

As used herein, the term "carbonyl," when alone includes formyl —C(═O)H and in combination is a —C(═O)— group.

As used herein, the term "carboxyl" or "carboxy" refers to —C(═O)OH or the corresponding "carboxylate" anion, such as is in a carboxylic acid salt. An "O-carboxy" group refers to a RC(═O)O— group, where R is as defined herein. A "C-carboxy" group refers to a —C(═O)OR groups where R is as defined herein.

As used herein, the term "cyano" refers to —CN.

As used herein, the term "carbocyclyl" refers to a saturated or partially saturated monocyclic or a fused bicyclic or tricyclic group wherein the ring atoms of the cyclic system are all carbon and wherein each cyclic moiety contains from 3 to 12 carbon atom ring members. "Carbocyclyl" encompasses benzo fused to a carbocyclyl ring system. One group of carbocyclyls have from 5 to 7 carbon atoms. Examples of carbocyclyl groups include, but are not limited to, cyclopropyl, cyclobutyl, cyclopentyl, cyclohexyl, and cycloheptyl, tetrahydronapthyl, indanyl, octahydronaphthyl, 2,3-dihydro-1H-indenyl, or adamantyl.

As used herein, the term "cycloalkyl" refers to a saturated monocyclic, bicyclic or tricyclic group wherein the ring atoms of the cyclic system are all carbon and wherein each cyclic moiety contains from 3 to 12 carbon atom ring members. One group of cycloalkyls has from 5 to 7 carbon atoms. Examples of cycloalkyl groups include, but are not limited to, cyclopropyl, cyclobutyl, cyclopentyl, cyclohexyl, cycloheptyl, or adamantyl.

As used herein, the term "cycloalkenyl" refers to a partially saturated monocyclic, bicyclic or tricyclic group wherein the ring atoms of the cyclic system are all carbon and wherein each cyclic moiety contains from 3 to 12 carbon atom ring members. One group of carboalkenyls have from 5 to 7 carbon atoms. Examples of cycloalkenyl groups include, but are not limited to, cyclobutenyl, cyclopentenyl, or cyclohexenyl.

As used herein, the term "cyclyl" refers to an aryl, heterocyclyl, or carbocyclyl group as defined herein.

As used herein, the term "ester" refers to a carboxy group bridging two moieties linked at carbon atoms.

As used herein, the term "ether" refers to an oxy group bridging two moieties linked at carbon atoms.

As used herein, the term "halo" or "halogen" refers to fluorine, chlorine, bromine, or iodine.

As used herein, the term "haloalkoxy" refers to a haloalkyl group attached to the parent molecular moiety through an oxygen atom. Examples of haloalkoxy groups include, but are not limited to, trifluoromethoxy, 2-fluoroethoxy, or 3-chloropropoxy.

As used herein, the term "haloalkyl" refers to an alkyl group having the meaning as defined above wherein one or more hydrogens are replaced with a halogen. Specifically embraced are monohaloalkyl, dihaloalkyl or polyhaloalkyl groups. A monohaloalkyl group, for one example, may have an iodo, bromo, chloro or fluoro atom within the group. Dihalo or polyhaloalkyl groups may have two or more of the same halo atoms or a combination of different halo groups. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl or dichloropropyl.

As used herein, "haloalkylene" refers to a haloalkyl group attached at two or more positions. Examples include, but are not limited to, fluoromethylene (—CFH—), difluoromethylene (—CF$_2$—), or chloromethylene (—CHCl—).

As used herein, the term "heteroalkyl" refers to a stable straight or branched alkyl chain, wherein one, two, or three carbons forming the alkyl chain are replaced by 1, 2, or 3 heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_7$—NH—OCH$_3$.

As used herein, the term "heteroalkylene" refers to a heteroalkyl group attached at two or more positions. Examples include, but are not limited to, —CH$_2$OCH$_2$—, —CH$_2$SCH$_2$—, —CH$_2$NHCH$_2$—, —CH$_2$S—, or —CH$_2$NCH(CH$_3$)CH$_2$—.

As used herein, the term "heteroaryl," refers to a 3 to 7 membered unsaturated monocyclic ring, or a fused monocyclic, bicyclic, or tricyclic ring system in which the rings are aromatic and which at least one ring contains at least one atom selected from the group consisting of O, S, and N. One group of heteroaryls has from 5 to 7 carbon atoms. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, or furopyridinyl.

As used herein, the term "heterocyclyl" or "heterocycle," each refer to a saturated, partially unsaturated, or fully unsaturated monocyclic, bicyclic, or tricyclic heterocyclic group containing at least one heteroatom as a ring member, wherein each said heteroatom may be independently selected from the group consisting of nitrogen, oxygen, and sulfur wherein the nitron or sulfur atoms may be oxidized (e.g., —N=O, —S(=O)—, or —S(=O)$_2$—). Additionally, 1, 2, or 3 of the carbon atoms of the heterocyclyl may be optionally oxidized (e.g., to give an oxo group or =O). One group of heterocyclyls has from 1 to 4 heteroatoms as ring members. Another group of heterocyclyls has from 1 to 2 heteroatoms as ring members. One group of heterocyclyls has from 3 to 8 ring members in each ring. Yet another group of heterocyclyls has from 3 to 7 ring members in each ring. Again another group of heterocyclyls has from 5 to 6 ring members in each ring. "Heterocyclyl" is intended to encompass a heterocyclyl group fused to a carbocyclyl or benzo ring systems. Examples of heterocyclyl groups include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, or imidazolidinyl. Examples of heteroaryls that are heterocyclyls include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, or furopyridinyl.

As used herein, the term "heterocycloalkyl," refers to a heterocyclyl group that is not fully saturated e.g., one or more of the rings systems of a heterocycloalkyl is not aromatic. Examples of heterocycloalkyls include piperazinyl, morpholinyl, piperidinyl, or pyrrolidinyl.

As used herein, the term "hydroxyl," as used herein, refers to —OH.

As used herein, the term "hydroxyalkyl," as used herein, refers to a hydroxy group attached to the parent molecular moiety through an alkyl group.

As used herein, the phrase "in the main chain," refers to the longest contiguous or adjacent chain of carbon atoms starting at the point of attachment of a group to the compounds of any one of the formulas disclosed herein.

As used herein, the term "isocyanato," refers to a —N=C=O group.

As used herein, the term "isothiocyanato," refers to a —N=C=S group.

As used herein, the term phrase "linear chain of atoms" refers to the longest straight chain of atoms independently selected from carbon, nitrogen, oxygen and sulfur.

As used herein, the term "lower," where not otherwise specifically defined, means containing from 1 to and including 6 carbon atoms.

As used herein, the term "lower alkynyl" refers to a straight-chain or branched-chain hydrocarbon group having one or more triple bonds and containing from 2 to 6 carbon atoms. Examples of lower alkynyl groups include, but are not limited to, ethynyl, propynyl, butyn-1-yl, butyn-2-yl, pentyn-1-yl, 3-methylbutyn-1-yl, or hexyn-2-yl.

As used herein, the term "lower aryl," means phenyl or naphthyl.

As used herein, the term "lower heteroaryl," means monocyclic heteroaryl comprising five or six ring members, of which between one and four of said ring members may be heteroatoms selected from O, S, or N.

As used herein, the term "lower cycloalkyl," refers to a monocyclic cycloalkyl having between three and six ring members. Examples of lower cycloalkyl include, but are not limited to, cyclopropyl, cyclobutyl, cyclopentyl, and cyclohexyl.

As used herein, the term "lower carbocyclyl" refers to a saturated or partially saturated monocyclic group, the ring atoms of which are all carbon atoms, wherein said monocyclic group contains from 3 to 6 carbon atom ring members. Examples of lower carbocyclyl groups include, but are not limited to, cyclopropyl, cyclobutyl, cyclopentyl, or cyclohexyl.

As used herein, the term "lower heterocyclyl," refers to a monocyclic heterocyclyls having between three and six ring members, of which between one and four may be heteroatoms selected from the group consisting of O, S, and N wherein the N and S group may be optionally oxidized (e.g., —N(=O)—, —S(=O)—, and —S(=O)$_2$—)). Examples of lower heterocyclyls include, but are not limited to, pyrrolidinyl, imidazolidinyl, pyrazolidinyl, piperidinyl, piperazinyl, and morpholinyl. Lower heterocyclyls may be saturated or partially unsaturated which is a lower heterocycloalkyl.

As used herein, the term "lower amino," refers to —NRR', wherein R and R' are independently selected from the group consisting of hydrogen, lower alkyl, and lower heteroalkyl. Additionally, the R and R' of a lower amino group may combine to form a five- or six-membered heterocycloalkyl.

As used herein, the term "mercaptyl," refers to an RS— group, where R is as defined herein.

As used herein, the term "nitro," refers to —NO$_2$.

As used herein, the terms "oxy" or "oxa," refer to —O—.

As used herein, the term "oxo," refers to =O.

As used herein, the terms "sulfonate" "sulfonic acid" and "sulfonic," refers to the —SO$_3$H group and its anion as the sulfonic acid is used in salt formation.

As used herein, the term "sulfanyl," to —S—.

As used herein, the term "sulfinyl," refers to —S(=O) (R)—, with R as defined herein.

As used herein, the term "sulfonyl," refers to —S(=O)$_2$R, with R as defined herein.

As used herein, the term "sulfonamide", refers to an N-sulfonamido or S-sulfonamido group as defined herein.

As used herein, the term "N-sulfonamido," refers to a RS(=O)$_2$N(R')— group with R and R' as defined herein.

As used herein, the term "S-sulfonamido," refers to a —S(=O)$_2$NRR', group, with R and R' as defined herein.

As used herein, the terms "thia" and "thio," refer to a —S— group or anether wherein the oxygen is replaced with sulfur. The oxidized derivatives of the thio group, namely sulfinyl and sulfonyl, are included in the definition of thia and thio.

As used herein, the term "thiol," refers to an —SH group.

As used herein, the term "thiocarbonyl," when alone includes thioformyl —C(S)R group with R as defined herein.

As used herein, the term "N-thiocarbamyl," refers to an ROC(=S)N(R')— group, with R and R' as defined herein.

As used herein, the term "O-thiocarbamyl," refers to a —OC(=S)NRR' group with R and R' as defined herein.

As used herein, the term "thiocyanato," refers to a —SCN group.

As used herein, the term "trihalomethanesulfonamido," refers to a X$_3$CS(=O)$_2$N(R)— group where X is an independently chosen halogen and R as defined herein.

As used herein, the term "trihalomethanesulfonyl," refers to a X$_3$CS(O)$_2$— group where X is an independently chosen halogen.

As used herein, the term "trihalomethoxy," refers to a X$_3$CO— group where X is an independently chosen halogen.

As used herein, the term "trisubstituted silyl," refers to a silicone group substituted at its three free valences with groups as listed herein under the definition of for R and R'. Examples include, but are not limited to, trimethysilyl, tert-butyldimethylsilyl, or triphenylsilyl.

As used herein, the term "urea," refers to a —N(R)C(=O)N(R') group wherein R and R' are as defined herein.

As used herein, the term "optionally substituted" means the preceding or anteceding group may be substituted or unsubstituted. When substituted, the substituents of an "optionally substituted" group may include, without limitation and unless defined otherwise, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, aminoalkyl, amido, nitro, thiol, lower alkylthio, lower haloalkylthio, lower perhaloalkylthio, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, carbamate, and urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with." In one specific definition, the optional substituents are chosen from hydroxyl, halo, alkyl, alkoxy, haloalkyl, haloalkoxy, —N((C1-C3)alkyl)$_2$, —NH((C1-C3)alkyl), —NHC(=O)((C1-C3)alkyl), C(=O)OH, —C(=O)O((C1-C3)alkyl), —C(=O)(C1-C3)alkyl), —C(=O)NH$_2$, —C(=O)NH(C1-C3)alkyl), —C(=O)NH(cycloalkyl), —C(=O)N(C1-C3)alkyl)$_2$, —S(=O)$_2$((C1-C3)alkyl), —S(=O)$_2$NH$_2$, —S(=O)$_2$N((C1-C3)alkyl)$_2$, —S(=O)$_2$NH((C1-C3)alkyl), —CHF$_2$, —OCHF$_2$, SCF$_3$, —CF$_3$, —CN, —NH$_2$, —NO$_2$, or tetrazolyl.

The term R or the term R', appearing by itself and without a number designation, unless otherwise defined, refers to a moiety selected from the group consisting of hydrogen, alkyl, cycloalkyl, heteroalkyl, haloalkyl, aryl, heteroaryl and heterocycloalkyl. Whether an R group has a number designation or not, every R group, including R, R' and RP where p=(1, 2, 3, . . . p), every substituent, and every term should be understood to be independent of every other in terms of selection from a group. Should any variable, substituent, or term (e.g., aryl, heterocyclyl, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(=O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms. The compounds of formula I may exist in different physical forms, i.e. amorphous and crystalline forms. Moreover, the compounds of the invention may have the ability to crystallize in more than one form, a characteristic which is known as polymorphism. Polymorphs can be distinguished by various physical properties well known in the art such as X-ray diffraction pattern, melting point or solubility. All physical forms of the compounds of formula I, including all polymorphic forms ("polymorphs") thereof, are included within the scope of the invention.

As used herein, the term "preventing an increase in a symptom," refers to both not allowing a symptom to increase or worsen, as well as reducing the rate of increase in the symptom. For example, a symptom can be measured as the amount of particular disease marker, i.e., a protein (e.g., cancer biomarker). In another example the symptom can be cognitive decline. Preventing an increase, according to the definition provided herein, means that the amount of symptom (e.g., protein or cognitive decline) does not increase or that the rate at which it increases is reduced.

As used herein, the term "treating a disease or disorder," refers to a slowing of or a reversal of the progress of the disease. Treating a disease or disorder includes treating a symptom and/or reducing the symptoms of the disease.

As used herein, the term "preventing a disease or disorder," refers to a slowing of the disease or of the onset of the disease or the symptoms thereof. Preventing a disease or disorder can include stopping the onset of the disease or symptoms thereof. As used herein, the term "unit dosage form" refers to a physically discrete unit, such as a capsule or tablet suitable as a unitary dosage for a human patient. Each unit contains a predetermined quantity of a compound of Formula (I), which was discovered or believed to produce the desired pharmacokinetic profile which yields the desired therapeutic effect. The dosage unit is composed of a compound of Formula (I), in association with at least one pharmaceutically acceptable carrier, salt, excipient, or combination thereof.

As used herein, the term "subject" or "patient" or "individual", such as the subject in need of treatment or prevention, refers to, e.g., a eukaryote, an animal, a vertebrate animal, a mammal, a rodent (e.g. a guinea pig, a hamster, a rat, a mouse), a murine (e.g. a mouse), a canine (e.g. a dog), a feline (e.g. a cat), an equine (e.g. a horse), a primate, a simian (e.g. a monkey or ape), a monkey (e.g. a marmoset, a baboon), an ape (e.g. gorilla, chimpanzee, orangutang, gibbon), or a human. The meaning of the terms "eukaryote", "animal", "mammal", etc. is well known in the art and can, for example, be deduced from Wehner and Gehring (1995; Thieme Verlag). In the context of this invention, it is particularly envisaged that animals are to be treated which are economically, agronomically or scientifically important. Scientifically important organisms include, but are not limited to, mice, rats, and rabbits. Lower organisms such as, e.g., fruit flies like *Drosophila melagonaster* and nematodes like *Caenorhabditis elegans* may also be used in scientific approaches. Non-limiting examples of agronomically important animals are sheep, cattle and pig, while, for example, cats and dogs may be considered as economically important animals. Preferably, the subject/patient is a mammal; more preferably, the subject/patient is a human or a non-human mammal (such as, e.g., a guinea pig, a hamster, a rat, a mouse, a rabbit, a dog, a cat, a horse, a monkey, an ape, a marmoset, a baboon, a gorilla, a chimpanzee, an orangutang, a gibbon, a sheep, cattle, or a pig); even more preferably, the subject/patient is a human.

As used herein, the term "dose" or "dosage," refers the amount of active ingredient that an individual takes or is administered at one time. For example, a 40 mg dose of a compound of Formula (I) refers to, in the case of a twice-daily dosage regimen, a situation where the individual takes 40 mg of a compound of Formula (I) twice a day, e.g., 40 mg in the morning and 40 mg in the evening. The 40 mg of a compound of Formula (I) dose can be divided into two or more dosage units, e.g., two 20 mg dosage units of a compound of Formula (I) in tablet form or two 20 mg dosage units of a compound of Formula (I) in capsule form.

As used herein, a "pharmaceutically acceptable prodrug" is a compound that may be converted under physiological conditions or by solvolysis to the specified compound or to a pharmaceutically acceptable salt of such compound.

As used herein, a "pharmaceutically active metabolite" is intended to mean a pharmacologically active product produced through metabolism in the body of a specified compound or salt thereof. Metabolites of a compound may be identified using routine techniques known in the art and their activities determined using tests such as those described herein.

As used herein, a "pharmaceutically acceptable salt" is intended to mean a salt that retains the biological effectiveness of the free acids and bases of the specified compound and that is not biologically or otherwise undesirable. A compound for use in the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrophosphates, dihydrophosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4 dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, gamma-hydroxybutyrates, glycollates, tartrates, methane-sulfonates, propanesulfonates, naphthalene-1-sulfonates, naphthalene-2-sulfonates, or mandelates.

As used herein, a "pharmaceutically acceptable carrier" refers to a non-API (API refers to Active Pharmaceutical Ingredient) substances such as disintegrators, binders, fillers, and lubricants used in formulating pharmaceutical products. They are generally safe for administering to humans according to established governmental standards, including those promulgated by the United States Food and Drug Administration and the European Medical Agency.

As is understood by the skilled artisan, certain variables in the list of substituents are repetitive (different name for the same substituent), generic to other terms in the list, and/or partially overlap in content with other terms. In the compounds of the invention, the skilled artisan recognizes that substituents may be attached to the remainder of the molecule via a number of positions and the preferred positions are as illustrated in the Examples.

Additionally, the compound of Formula (I) can contain asymmetric carbon atoms and can therefore exist in racemic and optically active forms. Thus, optical isomers or enantiomers, racemates, tautomers, and diastereomers are also encompassed in the compounds of Formula (I). The methods of present invention include the use of all such isomers and mixtures thereof. Methods of separation of enantiomeric and diastereomeric mixtures are well known to one skilled in the art. For example, racemic forms can be resolved by physical methods, such as, e.g., fractional crystallization, separation or crystallization of diastereomeric derivatives or separation by chiral column chromatography. The individual optical isomers can be obtained from the racemates using conventional methods, such as, e.g., salt formation with an optically active acid followed by crystallization. The present invention encompasses any isolated racemic or optically active form of compounds described in Formula (I), or any mixture thereof. In one aspect, the compounds of the invention have a trans configuration around the cyclopropyl ring as in trans-phenylcyclopropylamine. In one aspect, the compounds of the invention have a cis configuration around the cyclopropyl ring as in cis-phenylcyclopropylamine. In a preferred aspect, the compounds of Formula (I) have the trans configuration.

Typically, compounds according to Formula (I) can be effective at an amount of from about 0.01 µg/kg to about 100 mg/kg per day based on total body weight. The active ingredient may be administered at once, or may be divided into a number of smaller doses to be administered at predetermined intervals of time. The suitable dosage unit for each administration can be, e.g., from about 1 µg to about 2000 mg, preferably from about 5 µg to about 1000 mg.

It should be understood that the dosage ranges set forth above are exemplary only and are not intended to limit the scope of this invention. The therapeutically effective amount for each active compound can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like, as will be apparent to a skilled artisan. The amount of administration can be adjusted as the various factors change over time.

For oral delivery, the active compounds can be incorporated into a formulation that includes pharmaceutically acceptable carriers such as binders (e.g., gelatin, cellulose, gum tragacanth), excipients (e.g., starch, lactose), lubricants (e.g., magnesium stearate, silicon dioxide), disintegrating agents (e.g., alginate, Primogel, and corn starch), and sweetening or flavoring agents (e.g., glucose, sucrose, saccharin, methyl salicylate, and peppermint) The formulation can be orally delivered in the form of enclosed gelatin capsules or compressed tablets. Capsules and tablets can be prepared in any conventional techniques. The capsules and tablets can also be coated with various coatings known in the art to modify the flavors, tastes, colors, and shapes of the capsules and tablets. In addition, liquid carriers such as fatty oil can also be included in capsules.

Suitable oral formulations can also be in the form of suspension, syrup, chewing gum, wafer, elixir, and the like. If desired, conventional agents for modifying flavors, tastes, colors, and shapes of the special forms can also be included. In addition, for convenient administration by enteral feeding tube in patients unable to swallow, the active compounds can be dissolved in an acceptable lipophilic vegetable oil vehicle such as olive oil, corn oil and safflower oil.

The active compounds can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacteria agents, surfactants, and antioxidants can all be included. For example, useful components include sodium chloride, acetates, citrates or phosphates buffers, glycerin, dextrose, fixed oils, methyl parabens, polyethylene glycol, propylene glycol, sodium bisulfate, benzyl alcohol, ascorbic acid, and the like. The parenteral formulations can be stored in any conventional containers such as vials and ampoules.

Routes of topical administration include nasal, bucal, mucosal, rectal, or vaginal applications. For topical administration, the active compounds can be formulated into lotions, creams, ointments, gels, powders, pastes, sprays, suspensions, drops and aerosols. Thus, one or more thickening agents, humectants, and stabilizing agents can be included in the formulations. Examples of such agents include, but are not limited to, polyethylene glycol, sorbitol, xanthan gum, petrolatum, beeswax, or mineral oil, lanolin, squalene, and the like. A special form of topical administration is delivery by a transdermal patch. Methods for preparing transdermal patches are disclosed, e.g., in Brown, et al. (1988) *Ann. Rev. Med.* 39:221-229 which is incorporated herein by reference.

Subcutaneous implantation for sustained release of the active compounds may also be a suitable route of administration. This entails surgical procedures for implanting an active compound in any suitable formulation into a subcutaneous space, e.g., beneath the anterior abdominal wall. See, e.g., Wilson et al. (1984) *J. Clin. Psych.* 45:242-247. Hydrogels can be used as a carrier for the sustained release of the active compounds. Hydrogels are generally known in the art. They are typically made by crosslinking high molecular weight biocompatible polymers into a network, which swells in water to form a gel like material. Preferably, hydrogels are biodegradable or biosorbable. For purposes of this invention, hydrogels made of polyethylene glycols, collagen, or poly (glycolic-co-L-lactic acid) may be useful. See, e.g., Phillips et al. (1984) *J. Pharmaceut. Sci.,* 73: 1718-1720.

The active compounds can also be conjugated, to a water soluble non-immunogenic non-peptidic high molecular weight polymer to form a polymer conjugate. For example, an active compound is covalently linked to polyethylene glycol to form a conjugate. Typically, such a conjugate exhibits improved solubility, stability, and reduced toxicity and immunogenicity. Thus, when administered to a patient, the active compound in the conjugate can have a longer half-life in the body, and exhibit better efficacy. See generally, Burnham (1994) *Am. J. Hosp. Pharm.* 15:210-218. PEGylated proteins are currently being used in protein replacement therapies and for other therapeutic uses. For example, PEGylated interferon (PEG-INTRON A®) is clinically used for treating Hepatitis B. PEGylated adenosine deaminase (ADAGEN®) is being used to treat severe combined immunodeficiency disease (SCIDS). PEGylated L-asparaginase (ONCAPSPAR®) is being used to treat acute lymphoblastic leukemia (ALL). It is preferred that the covalent linkage between the polymer and the active compound and/or the polymer itself is hydrolytically degradable under physiological conditions. Such conjugates known as "prodrugs" can readily release the active compound inside the body. Controlled release of an active compound can also be achieved by incorporating the active ingredient into microcapsules, nanocapsules, or hydrogels generally known in the art. Other pharmaceutically acceptable prodrugs of the compounds of this invention include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters.

Liposomes can also be used as carriers for the active compounds of the present invention. Liposomes are micelles made of various lipids such as cholesterol, phospholipids, fatty acids, and derivatives thereof. Various modified lipids can also be used. Liposomes can reduce the toxicity of the active compounds, and increase their stability. Methods for preparing liposomal suspensions containing active ingredients therein are generally known in the art. See, e.g., U.S. Pat. No. 4,522,811; Prescott, Ed., Methods in Cell Biology, Volume XIV, Academic Press, New York, N.Y. (1976).

The active compounds can also be administered in combination with another active agent that synergistically treats or prevents the same symptoms or is effective for another disease or symptom in the patient treated so long as the other active agent does not interfere with or adversely affect the effects of the active compounds of this invention. Such other active agents include but are not limited to anti-inflammation agents, antiviral agents, antibiotics, antifungal agents, anti-thrombotic agents, cardiovascular drugs, cholesterol lowering agents, anti-cancer drugs, hypertension drugs, and the like.

Examples of antineoplastic agents that can be used in combination with the compounds and methods of the present invention include, in general, and as appropriate, alkylating agents, anti-metabolites, epidophyllotoxins, antineoplastic enzymes, topoisomerase inhibitors, procarbazines, mitoxantrones, platinum coordination complexes, biological response modifiers and growth inhibitors, hormonal/anti-hormonal therapeutic agents and haematopoietic growth factors. Exemplary classes of antineoplastic include the anthracyclines, vinca drugs, mitomycins, bleomycins, cytotoxic nucleosides, epothilones, discodermolides, pteridines, diynenes and podophyllotoxins. Particularly useful members of those classes include, for example, caminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, carboplatin, cyclophosphamide, bleomycin, gemcitibine, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

General Synthetic Route Description

The compounds of formula (I) can be obtained by following the processes described below. As it will be obvious to one skilled in the art, the exact method used to prepare a given compound may vary depending on its chemical structure. Unless otherwise stated, in the methods described below the meanings of the different substituents are the meanings described above with regard to a compound of formula (I).

The compounds of Formula (I) can be synthesized, for example, by the general route described in the Scheme 1:

SCHEME 1:

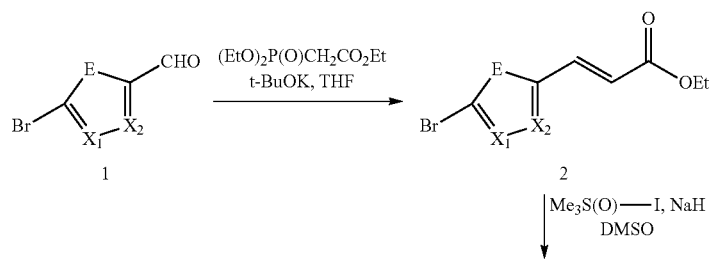

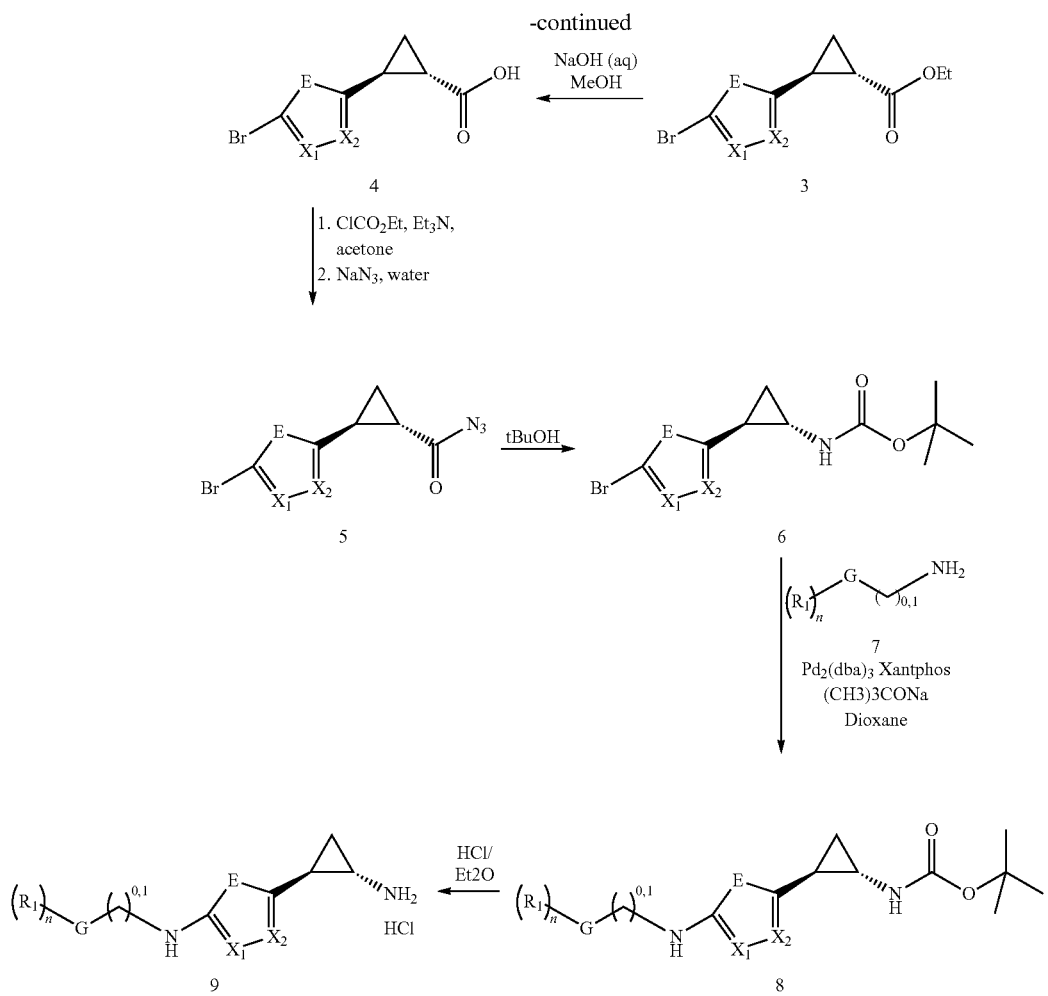

DMSO (Dimethyl sulfoxide), Pd$_2$(dba)$_3$ (Tris(dibenzylideneacetone)dipalladium(0)), THF (Tetrahydrofurane), Xantphos (4,5-Bis(diphenylphosphino)-9,9-dimethylxanthene).

Aldehydes of Formula (1) are subjected to a Horner-Wadsworth-Emmons reaction under standard conditions, well known in the art, such as using triethyl phosphono acetate and a strong base preferably potassium tert-butoxide in a suitable solvent such as tetrahydrofurane at a suitable temperature preferably around 0° C. to get the ethyl acrylate derivatives of formula (2), which are then subjected to cyclopropanation reaction using trimethylsulfoxonium iodide and sodium hydride in dimethyl sulfoxide as a solvent at a suitable temperature, preferably around room temperature, leading to (trans)-ethyl cyclopropanecarboxylate derivatives of formula (3) (as a racemic mixture of the (1S,2R) and (1R,2S) isomers). Hydrolysis to the corresponding (trans)-cyclopropanecarboxylic acid derivatives of formula (4) can be performed under basic conditions using for example NaOH in a suitable solvent such as MeOH at room temperature. The subsequent reaction of compound (4), first with ethyl chloroformate and triethylamine in acetone at low temperature, e.g. −15° C., and later with sodium azide in water at low temperature, e.g. −10° C., leads to the formation of (trans)-cyclopropanecarbonyl azide derivatives of formula (5). Reaction with tert-butanol results in the formation of tert-butyl (trans)-cyclopropylcarbamate derivatives of formula (6). The reaction of compound (6) with amine derivatives of formula (7) using Xantphos, Tris(dibenzylideneacetone)dipalladium(0) as catalyst, and a base such as sodium tert-butoxide in a suitable solvent such as dioxane at a suitable temperature such as for example around 80° C. leads to the formation of tert-butyl (trans)-cyclopropylcarbamate derivatives of formula (8). Deprotection of the Boc-group in acidic conditions, for example using HCl 2M in diethyl ether or dioxane in a suitable solvent such as diethyl ether or dioxane, respectively, leads to the formation of the (trans)-cyclopropanamine derivatives of formula (9), which correspond to a compound of the present invention as defined above.

Individual isomers (1S,2R) and (1R,2S) can be obtained by chiral separation of the trans racemic mixture of compounds (9) thus obtained. Alternatively, the separation of the trans racemic mixture into the individual trans (1S,2R) and (1R,2S) isomers can be performed upon the inteiinediate (3) and then the above synthetic pathway from compound (3) onwards is performed using the single (1S,2R) or (1R,2S) isomers of (3) to render directly the (1S,2R) or (1R,2S) isomers of compound (9), respectively.

Aldehydes of formula (1) and amines of formula (7) are commercially available or can be prepared using well known synthetic procedures starting from readily available starting materials.

The compounds of Formula (I) can also be prepared in accordance with the following examplary method described in Scheme 2:

SCHEME 2:

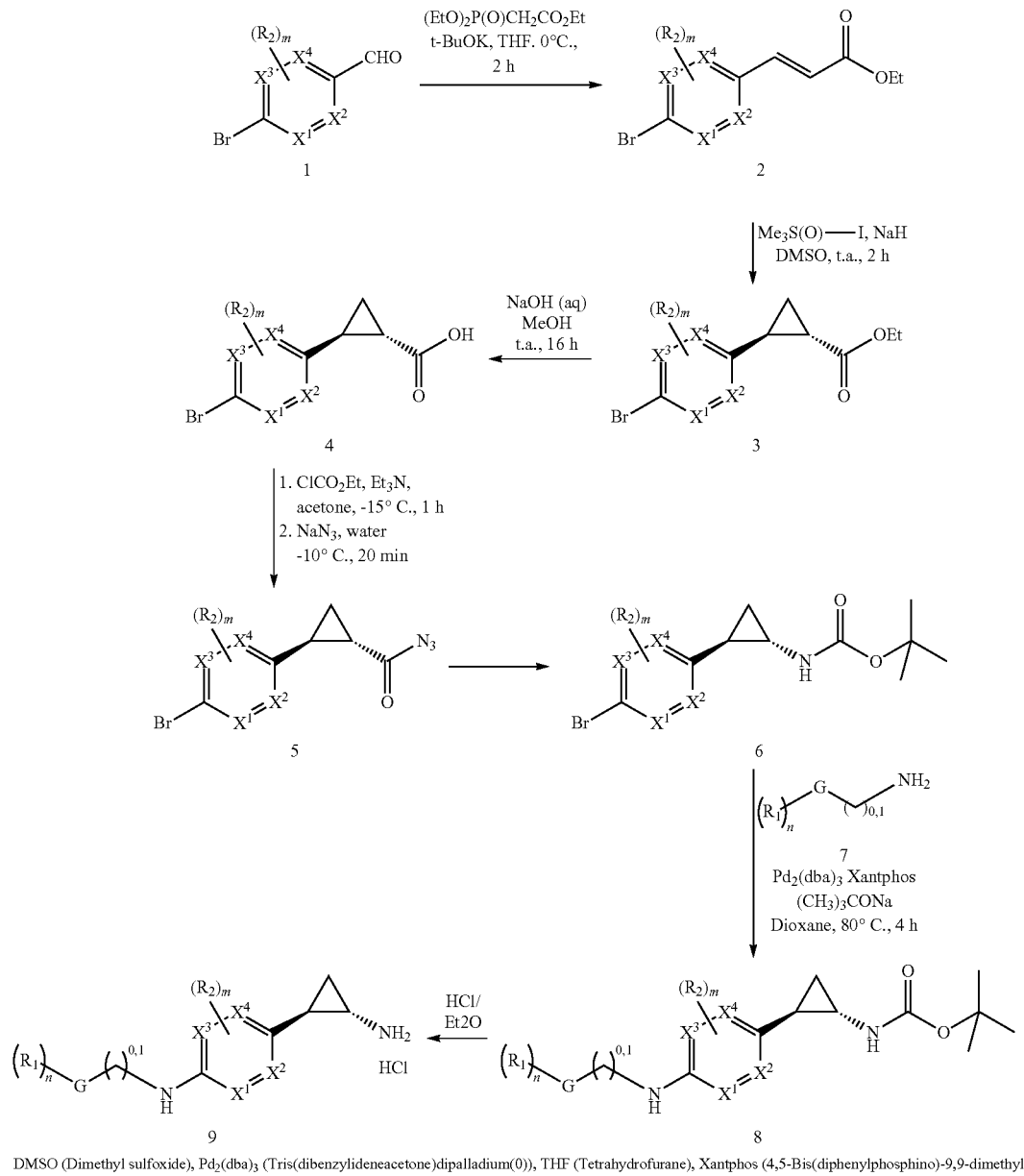

DMSO (Dimethyl sulfoxide), Pd₂(dba)₃ (Tris(dibenzylideneacetone)dipalladium(0)), THF (Tetrahydrofurane), Xantphos (4,5-Bis(diphenylphosphino)-9,9-dimethylxanthene).

Commercially available aldehydes of Formula (1) have been subjected to a Horner-Wadsworth-Emmons reaction using triethyl phosphono acetate and potassium tert-butoxide in tetrahydrofurane at 0° C. to get the ethyl acrylate derivatives of formula (2) which is subjected to cyclopropanation reaction using trimethylsulfoxonium iodide and sodium hydride in dimethyl sulfoxide as a solvent leading to (trans)-ethyl cyclopropanecarboxylate derivatives of formula (3) (being trans ((1S,2R), (1R,2S)) mixture although the individual diastereoisomers corresponding to (1S,2R) and (1R,2S) can be used). Hydrolysis to the corresponding (trans)-cyclopropanecarboxylic acid derivatives of formula (4) was performed using NaOH in MeOH. The reaction, first with ethyl chloroformate and triethylamine in acetone and later with sodium azide in water leads to the formation of (trans)-cyclopropanecarbonyl azide derivatives of formula (5). Reaction with tert-butanol results in the formation of tert-butyl (trans)-cyclopropylcarbamate derivatives of formula (6). Their reaction with commercially available amine derivatives of formula (7) using Xantphos, Tris(dibenzylideneacetone)dipalladium(0) as a catalyst, sodium tert-butoxide as a base and dioxane as a solvent leads to the formation of tert-butyl (trans)-cyclopropylcarbamate derivatives of formula (8). Deprotection of the Boc-group using HCl 2M in diethyl ether using diethyl ether as a solvent leads to the formation of the corresponding hydrochloride salt of the (trans)-cyclopropanamine derivatives of formula (9), which are subject of the present invention as defined above.

The compounds of Formula (I), in which E is —N(R3)-, —S— or —O—, can be prepared in accordance with the synthetic route described in Scheme 2 above, using commercially available, five-membered ring reagents (particularly five-membered ring aldehydes), such as, e.g., suitably substituted thiophene derivatives, thiazole derivatives, etc., as starting materials.

EXAMPLES

The program used to generate the names corresponding to the structures in the Example compounds below was ChemBioDraw Ultra 11.0.1. This program named the molecules as the (1S,2R) configuration due to the configuration of the input structure and the "trans" term has been substituted in the place of the (1S,2R) term specified by the program. The structures depicted for the Example compounds below are shown as having one particular stereochemical configuration around the cyclopropyl carbon atoms of the cyclylcyclopropylamine (e.g., phenylcyclopropylamine) core (1S,2R). All the compounds synthesized in the Examples are mixtures having both configurations (1R,2S) and (1S,2R), that is to say they are "trans" in respect to the cyclopropyl ring of the cyclopropyl ring system. This is due to the fact the cyclopropyl derivatives used as starting material are "trans". It is contemplated that the cis configuration starting material or the individual diastereoisomers could be used as starting material, all of which are either commercially or synthetically available. Thus, the invention relates to compounds of Formula (I) and those of the examples that have specific stereochemical configurations around the cyclopropyl ring e.g., trans ((1R,2S) and/or (1S,2R)) and cis ((1R,2S) and/or (1S,2S)). A preferred stereochemical configuration around the cyclopropyl ring is trans.

The compounds of the examples can also be synthesized or provided in a salt form. The skilled artisan is aware and capable of making salt forms and/or converting salt forms of the compounds of the invention, e.g., compounds of Formula (I) and those of the Examples. In some cases the compounds of Formula (I) and the Examples can be more stable as salt forms as compared to free base.

In reference to the synthetic schemes described herein the following intermediates (and analogous intermediates or derivatives thereof can be made using the following procedures.

Intermediate A (E)-ethyl 3-(6-bromopyridin-3-yl)acrylate

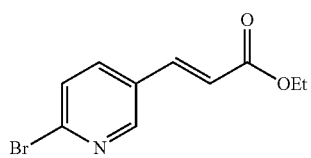 [SMILES: CCOC(=O)/C=C/c1ccc(Br)nc1]

Triethyl phosphonoacetate (26.6 g, 118.8 mmol) was added slowly dropwise to a mixture of Potassium-tert-butoxide (14.5 g, 129.6 mmol) in dry THF (200 mL) at −5° C., stirred for 20 min and then a solution of 6-bromopyridine-3-carboxaldehyde (20 g, 108 mmol) in dry THF (100 mL) was added slowly dropwise at −5° C. and stirred for 30 min. After completion, the reaction mixture was poured into ice water (350 mL) and extracted with EtOAc (2×300 mL). The combined organic extracts were washed with saturated NaHCO$_3$ solution (250 mL), water (250 mL) and brine (250 mL) and dried over anhydrous Na$_2$SO$_4$, filtered and evaporated to get (E)-ethyl 3-(6-bromopyridin-3-yl) acrylate (20 g, 72.9%) as brown color liquid. This is carried to next step without further purification.

Intermediate B (Trans)-ethyl-2-(6-bromopyridin-3-yl)cyclopropanecarboxylate

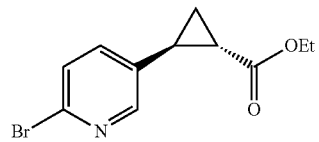 [SMILES: CCOC(=O)[C@H]1C[C@@H]1c1ccc(Br)nc1]

Trimethyl sulfoxonium iodide (20.8 g, 94.7 mmol) was added in small portions to a suspension of sodium hydride (4 g, 170.6 mmol) in dry DMSO (400 mL) at rt., stirred for 1 h until clear solution was obtained. A solution of (E)-ethyl 3-(6-bromopyridin-3-yl) acrylate (Intermediate A, 20 g, 78.7 mmol) in dry DMSO (20 mL) was added and stirred for 4 h. After completion, the reaction mixture was poured into ice water (700 mL), extracted with EtOAc (2×350 mL). The combined organic extracts were washed with water (250 mL), brine (250 mL) and dried over anhydrous Na$_2$SO$_4$, filtered and evaporated to give (trans)-ethyl-2-(6-bromopyridin-3-yl) cyclopropanecarboxylate (10 g, 47%) as brown liquid.

Intermediate C (Trans)-2-(6-bromopyridin-3-yl)cyclopropanecarboxylic acid hydrochloride

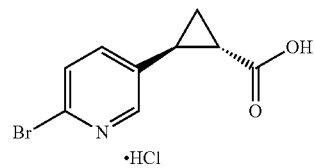 [SMILES: O=C(O)[C@H]1C[C@@H]1c1ccc(Br)nc1 ; Cl]

NaOH 4N solution (60 mL) was added to a solution of (trans)-ethyl-2-(6-bromopyridin-3-yl)cyclopropanecarboxylate (Intermediate B, 10 g, 37.1 mmol) in methanol (100 mL) and the reaction mixture was stirred at RT for 4 h. After completion, the solvent was evaporated and the residue was diluted with ice water (250 mL) and acidified with 4 N HCl solution, the aqueous layer was extracted with EtOAc (2×350 mL). The combined organic extracts were washed with water (250 mL), brine (250 mL) and dried over anhydrous Na$_2$SO$_4$, filtered and evaporated to give (trans)-2-(6-bromopyridin-3-yl)cyclopropanecarboxylic acid hydrochloride (5 g, 55.8%) as a light brown color solid.

Intermediate D (Trans)-2-(6-bromopyridin-3-yl)cyclopropanecarbonyl azide

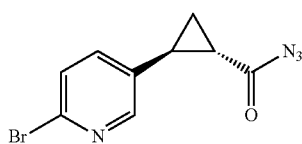 [SMILES: [N-]=[N+]=NC(=O)[C@H]1C[C@@H]1c1ccc(Br)nc1]

Ethyl chloroformate (5.8 mL, 62 mmol) was added to a solution of (trans)-2-(6-bromopyridin-3-yl)cyclopropanecarboxylic acid hydrochloride (Intermediate C, 5 g, 20.7 mmol) and Et$_3$N (14.2 mL, 103.7 mmol) in Acetone (100 mL) at −5° C., then reaction mixture was stirred at −5° C. for 1 h, then a solution of NaN$_3$ (2.7 g, 41.4 mmol) in water (10 mL) was added and stirred for 30 mins at RT. After completion the solvent was evaporated under vacuum. The crude residue was dissolved in ethyl acetate (200 mL), washed with water (80 mL), brine (80 mL), dried over anhydrous Na$_2$SO$_4$, filtered and evaporated to get (trans)-2-(6-bromopyridin-3-yl)cyclopropanecarbonyl azide (2.5 g, 45.5%) as a brown color gummy liquid.

Intermediate E tert-butyl (trans)-2-(6-bromopyridin-3-yl)cyclopropylcarbamate

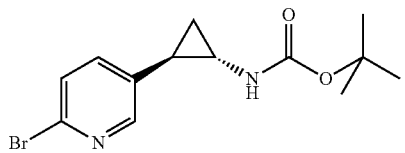 [SMILES: CC(C)(C)OC(=O)N[C@H]1C[C@@H]1c1ccc(Br)nc1]

A solution of (trans)-2-(6-bromopyridin-3-yl)cyclopropanecarbonyl azide (Intermediate D, 2.5 g, 9.36 mmol) in tert-butanol (80 mL) was heated at 90° C. for 16 h. After completion, the solvent was evaporated under vacuum and the residue was taken in water (100 mL) and extracted with EtOAc (2×100 mL). The combined organic extracts were washed with water (100 mL), brine (100 mL) and dried over anhydrous Na$_2$SO$_4$, filtered and evaporated. The crude residue was purified by flash column chromatography (SiO$_2$) by eluting with EtOAc:Hexane (2:8) to get tert-butyl (trans)-2-(6-bromopyridin-3-yl)cyclopropylcarbamate (1.1 g, 37.5%) as a light yellow solid. $^1$H-NMR (CDCl$_3$) δ (ppm): 1.16 (q, 1H), 1.23 (quin, 1H), 1.45 (s, 9H), 2.01 (m, 1H), 2.69 (m, 1H), 4.88 (br, 1H), 7.36 (s, 2H), 8.20 (s, 1H).

Example 1

5-((trans)-2-aminocyclopropyl)-N-(3-chlorophenyl)pyridin-2-amine hydrochloride

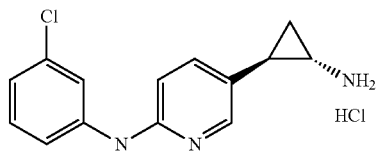

Step 1:
A solution of tert-butyl (trans)-2-(6-bromopyridin-3-yl) cyclopropylcarbamate (Intermediate E, 250 mg, 0.798 mmol), 3-chloroaniline (122 mg, 0.958 mmol), Sodium tert-butoxide (115 mg, 1.198 mmol) in 1,4-dioxane (5 mL) was degassed for 30 min, tris(dibenzylidene acetone)dipalladium (0) (36 mg, 0.039 mmol) and 4,5-Bis(diphenyl phosphino)-9,0-dimethyl xanthene (138 mg, 0.39 mmol) was added and heated for 4 h at 80° C. After completion, the solvent was evaporated; the residue was poured into ice cold water (10 mL) and extracted with EtOAc (2×20 mL). The combined extracts were washed with water (10 mL), brine (10 mL), dried over anhydrous Na$_2$SO$_4$, filtered and evaporated. The crude residue was purified by flash chromatography to give tert-butyl (trans)-2-(6-(3-chlorophenylamino)pyridin-3-yl) cyclopropylcarbamate (180 mg, 63%) as white solid.
Step 2:
HCl in dioxane (2 ml) was added to a solution of tert-butyl (trans)-2-(6-(3-chlorophenylamino) pyridin-3-yl)cyclopropyl carbamate (180 mg, 0.501 mmol) in 1,4-dioxane (2 mL) at 0° C. and stirred at RT for 4 h. After completion, the solvent was evaporated and the residue was triturated with diethyl ether (5 mL) followed by n-pentane (5 mL) to give 5-((trans)-2-aminocyclopropyl)-N-(3-chlorophenyl) pyridin-2-amine hydrochloride (120 mg, 81%) as off-white solid. $^1$H-NMR (400 MHz, DMSO-d6) δ: 1.2 (br, 1H), 1.4 (br, 1H), 2.3 (br, 1H), 2.8 (br, 1H), 7.0 (br, 2H), 7.31 (t, 1H), 7.42 (d, 1H), 7.54 (br, 1H), 7.87 (s, 1H), 8.06 (s, 1H), 8.59 (br, 2H), 9.82 (br, 1H); MS (M+H): 260.1

The following compounds can be synthesized following the method described for example 1 using the corresponding commercial available anilines.

Example 2

5-((trans)-2-aminocyclopropyl)-N-(4-chlorophenyl)pyridin-2-amine hydrochloride

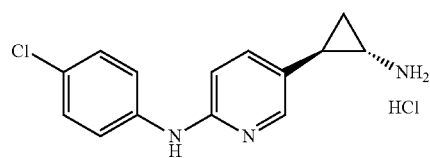 [SMILES: N[C@H]1C[C@@H]1c1ccc(Nc2ccc(Cl)cc2)nc1 ; Cl]

¹H-NMR (400 MHz, DMSO-d6) δ: 1.2 (q, 1H), 1.4 (quin, 1H), 2.3 (m, 1H), 2.8 (m, 1H), 6.95 (br, 1H), 7.37 (d, 2H), 7.55 (br, 1H), 7.61 (d, 2H), 8.02 (s, 1H), 8.55 (br, 2H), 9.78 (br, 1H); MS (M+H): 260.1

Example 3

5-((trans)-2-aminocyclopropyl)-N-(4-(trifluoromethyl)phenyl)pyridin-2-amine hydrochloride

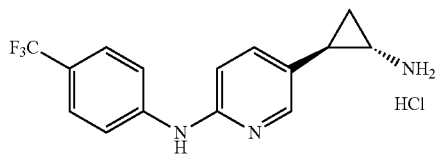 [SMILES: N[C@H]1C[C@@H]1c1ccc(Nc2ccc(C(F)(F)F)cc2)nc1 ; Cl]

¹H-NMR (400 MHz, DMSO-d6) δ: 1.2 (q, 1H), 1.4 (quin, 1H), 2.3 (m, 1H), 2.8 (m, 1H), 6.93 (br, 1H), 7.47 (br, 1H), 7.59 (d, 2H), 7.85 (d, 2H), 8.11 (s, 1H), 8.51 (br, 2H), 9.71 (br, 1H); MS (M+H): 294.1

Example 4

5-((trans)-2-aminocyclopropyl)-N-(3-methoxyphenyl)pyridin-2-amine hydrochloride

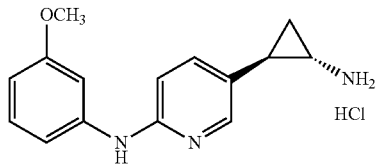 [SMILES: COc1cccc(Nc2ccc([C@H]3C[C@@H]3N)cn2)c1 ; Cl]

¹H-NMR (400 MHz, DMSO-d6) δ: 1.23 (q, 1H), 1.42 (quin, 1H), 2.35 (br, 1H), 2.82 (br, 1H), 3.76 (s, 3H), 6.73 (br, 1H), 7.0-7.2 (m, 3H), 7.30 (t, 1H), 7.70 (br, 1H), 7.99 (s, 1H), 8.66 (br, 3H), 10.25 (br, 1H); MS (M+H): 256.1

Example 5

5-((trans)-2-aminocyclopropyl)-N-(4-methoxyphenyl)pyridin-2-amine hydrochloride

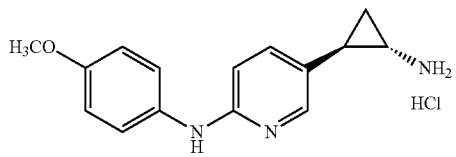 [SMILES: COc1ccc(Nc2ccc([C@H]3C[C@@H]3N)cn2)cc1 ; Cl]

¹H-NMR (400 MHz, DMSO-d6) δ: 1.22 (q, 1H), 1.42 (quin, 1H), 2.36 (m, 1H), 2.80 (m, 1H), 3.78 (s, 3H), 7.01 (d, 3H), 7.34 (d, 2H), 7.75 (d, 1H), 7.88 (s, 1H), 8.66 (br, 2H), 10.22 (br, 1H); MS (M+H): 256.2

Example 6

5-((trans)-2-aminocyclopropyl)-N-p-tolylpyridin-2-amine hydrochloride

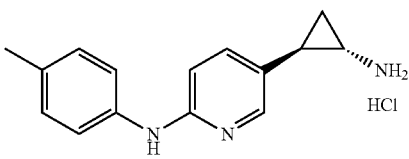 [SMILES: Cc1ccc(Nc2ccc([C@H]3C[C@@H]3N)cn2)cc1 ; Cl]

¹H-NMR (400 MHz, DMSO-d6) δ: 1.23 (q, 1H), 1.40 (quin, 1H), 2.30 (s, 3H), 2.33 (br, 1H), 2.80 (m, 1H), 7.00 (br, 1H), 7.20 (d, 2H), 7.35 (d, 2H), 7.67 (br, 1H), 7.93 (s, 1H), 8.58 (br, 3H), 10.00 (br, 1H); MS (M+H): 240.2

Example 7

5-((trans)-2-aminocyclopropyl)-N-m-tolylpyridin-2-amine hydrochloride

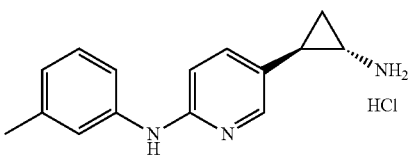 [SMILES: Cc1cccc(Nc2ccc([C@H]3C[C@@H]3N)cn2)c1 ; Cl]

¹H-NMR (400 MHz, DMSO-d6) δ: 1.23 (q, 1H), 1.42 (quin, 1H), 2.31 (s, 3H), 2.38 (br, 1H), 2.82 (m, 1H), 6.95 (br, 1H), 7.10 (br, 1H), 7.28 (m, 3H), 7.70 (br, 1H), 7.97 (s, 1H), 8.61 (br, 3H), 10.05 (br, 1H); MS (M+H): 240.2

Example 8

4-(5-((trans)-2-aminocyclopropyl)pyridin-2-ylamino)benzonitrile hydrochloride

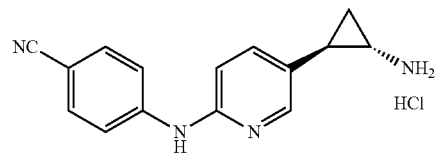 [SMILES: N#Cc1ccc(Nc2ccc([C@H]3C[C@@H]3N)cn2)cc1 ; Cl]

¹H-NMR (400 MHz, DMSO-d6) δ: 1.19 (q, 1H), 1.38 (quin, 1H), 2.32 (m, 1H), 2.79 (m, 1H), 6.95 (t, 1H), 7.47 (br, 1H), 7.67 (d, 2H), 7.85 (d, 2H), 8.13 (s, 1H), 8.54 (br, 3H), 9.85 (br, 1H); MS (M+H): 251.2

Example 9

3-(5-((trans)-2-aminocyclopropyl)pyridin-2-ylamino)benzonitrile hydrochloride

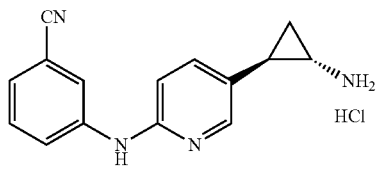 [SMILES: N#Cc1cccc(Nc2ccc([C@H]3C[C@@H]3N)cn2)c1 ; Cl]

¹H-NMR (400 MHz, DMSO-d6) δ: 1.22 (q, 1H), 1.38 (quin, 1H), 2.30 (br, 1H), 2.80 (br, 1H), 6.91 (br, 1H), 7.32 (s, 1H), 7.47 (m, 2H), 7.78 (d, 1H), 8.10 (s, 1H), 8.28 (s, 1H), 8.50 (br, 3H), 9.75 (br, 1H); MS (M+H): 251.2

Example 10

3-(5-((trans)-2-aminocyclopropyl)pyridin-2-ylamino)benzamide hydrochloride

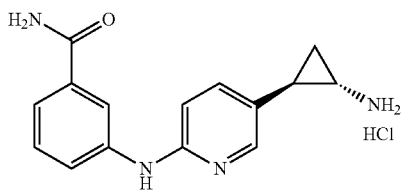 [SMILES: NC(=O)c1cccc(Nc2ccc([C@H]3C[C@@H]3N)cn2)c1 ; Cl]

¹H-NMR (400 MHz, DMSO D6) δ: 1.29 (q, 1H), 1.46 (quin, 1H), 2.42 (m, 1H), 2.89 (m, 1H), 7.45 (d, 1H), 7.54 (t, 1H), 7.70 (d, 1H), 7.82 (d, 1H), 7.91 (br, 1H), 8.10 (d, 1H), 8.32 (s, 1H), 8.59 (br, 3H), 11.05 (br, 1H); MS (M+H): 269.2

Example 11

4-(5-((trans)-2-aminocyclopropyl)pyridin-2-ylamino)benzamide hydrochloride

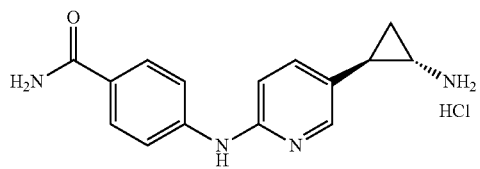 [SMILES: NC(=O)c1ccc(Nc2ccc([C@H]3C[C@@H]3N)cn2)cc1 ; Cl]

¹H-NMR (400 MHz, DMSO-d6) δ: 1.32 (q, 1H), 1.48 (quin, 1H), 2.44 (br, 1H), 2.91 (m, 1H), 6.74 (m, 2H), 7.90 (m, 2H), 8.09 (m, 1H), 8.10 (d, 1H), 8.32 (s, 1H), 8.60 (br, 3H), 11.21 (br, 1H); MS (M+H): 269.2

Example 12

5-((trans)-2-aminocyclopropyl)-N-(3-chlorobenzyl)pyridin-2-amine hydrochloride

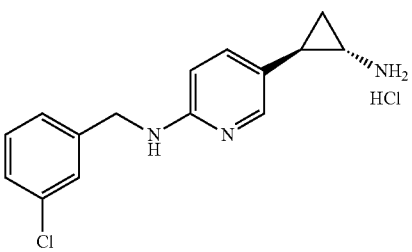 [SMILES: N[C@H]1C[C@@H]1c1ccc(NCc2cccc(Cl)c2)nc1 ; Cl]

Step 1:

A solution of tert-butyl (trans)-2-(6-bromopyridin-3-yl) cyclopropylcarbamate (Intermediate E, 350 mg, 1.118 mmol), 3-chlorobenzylamine (237 mg, 1.677 mmol), Sodium tert-butoxide (161 mg, 1.677 mmol) in 1,4-dioxane (7 mL) was degassed for 30 min, tris(dibenzylidene acetone)dipalladium(0) (51 mg, 0.055 mmol), 4,5-Bis(diphenyl phosphino)-9,0-dimethyl xanthene (193 mg, 0.335 mmol) was added and heated for 4 h at 80° C. After completion, the solvent was removed, the residue was poured into ice cold water (10 mL) and extracted with EtOAc (2×20 mL). The combined extracts were washed with water (10 mL), brine (10 mL), dried over anhydrous Na₂SO₄, filtered and evaporated. The crude residue was purified by flash chromatography to give tert-butyl (trans)-2-(6-(3-chlorobenzylamino) pyridin-3-yl)cyclopropyl carbamate (100 mg, yield: 24%) as white solid.

Step 2:

HCl in Dioxane (1 ml) was added to a solution of tert-butyl (trans)-2-(6-(3-chlorobenzylamino) pyridin-3-yl)cyclopropyl carbamate (100 mg, 0.268 mmol) in 1,4-dioxane (1 mL) at 0° C., stirred at RT for 4 h. After completion, the solvent was removed and the residue was triturated with diethyl ether (5 mL) followed by n-pentane (5 mL) to give 5-((trans)-2-aminocyclopropyl)-N-(3-chlorobenzyl)pyridin-2-amine hydrochloride (60 mg, yield: 72.2%) as off-white solid. ¹H-NMR (400 MHz, DMSO-d6) δ: 1.21 (q, 1H); 1.38 (quin, 1H), 2.32 (m, 1H), 2.81 (m, 1H), 4.67 (s, 2H), 7.04 (d, 1H), 7.40 (m, 3H), 7.49 (s, 1H), 7.74 (d, 1H), 7.86 (s, 1H), 8.57 (br, 3H), 9.06 (br, 1H). Mass (M+H): 274.2

The following compounds can be synthesized following the method described for example 12 using the corresponding commercial available amines.

Example 13

5-((trans)-2-aminocyclopropyl)-N-(4-chlorobenzyl)pyridin-2-amine hydrochloride

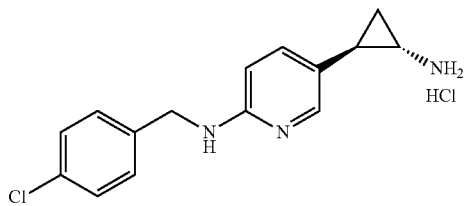 [SMILES: N[C@H]1C[C@@H]1c1ccc(NCc2ccc(Cl)cc2)nc1 ; Cl]

¹H-NMR (400 MHz, DMSO-d6) δ: 1.26 (q, 1H); 1.37 (quin, 1H), 2.32 (m, 1H), 2.81 (m, 1H), 4.60 (s, 2H), 7.05 (d, 1H), 7.43 (q, 4H), 7.74 (d, 1H), 7.82 (s, 1H), 8.62 (br, 3H), 9.16 (br, 1H). Mass (M+H): 274.2

Example 14

5-((trans)-2-aminocyclopropyl)-N-(3-(trifluoromethyl)benzyl)pyridin-2-amine hydrochloride

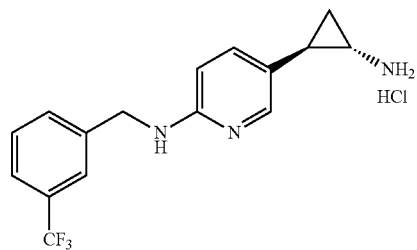 [SMILES: N[C@H]1C[C@@H]1c1ccc(NCc2cccc(C(F)(F)F)c2)nc1 ; Cl]

¹H-NMR (400 MHz, DMSO-d6) δ: 1.22 (q, 1H); 1.39 (quin, 1H), 2.33 (m, 1H), 2.81 (m, 1H), 4.76 (s, 2H), 7.07 (d, 1H), 7.6-7.78 (m, 4H), 7.80 (s, 1H), 7.86 (s, 1H), 8.58 (br, 3H), 9.06 (br, 1H). Mass (M+H): 308.2

Example 15

5-((trans)-2-aminocyclopropyl)-N-(4-(trifluoromethyl)benzyl)pyridin-2-amine hydrochloride

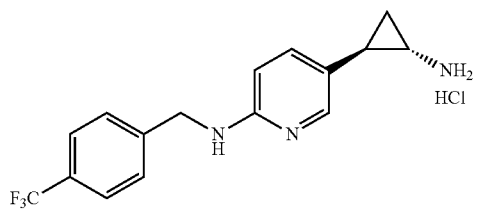 [SMILES: N[C@H]1C[C@@H]1c1ccc(NCc2ccc(C(F)(F)F)cc2)nc1 ; Cl]

¹H-NMR (400 MHz, CD3OD) δ: 1.40 (q, 1H); 1.45 (quin, 1H), 2.39 (m, 1H), 2.92 (m, 1H), 4.71 (s, 2H), 7.09 (d, 1H), 7.60 (d, 2H), 7.69 (d, 2H), 7.80 (s, 1H), 7.83 (d, 1H). Mass (M+H): 308.2

Example 16

5-((trans)-2-aminocyclopropyl)-N-(3-methylbenzyl)pyridin-2-amine hydrochloride

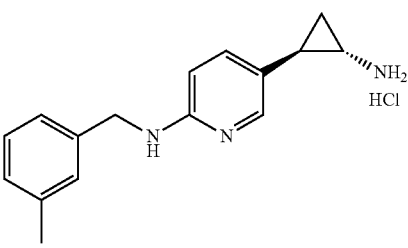 [SMILES: Cc1cccc(CNc2ccc([C@H]3C[C@@H]3N)cn2)c1 ; Cl]

¹H-NMR (400 MHz, CD3OD) δ: 1.38 (q, 1H); 1.45 (quin, 1H), 2.34 (s, 3H), 2.38 (m, 1H), 2.91 (m, 1H), 4.54 (s, 2H), 7.07 (d, 1H), 7.16 (d, 2H), 7.21 (s, 1H), 7.27 (m, 1H), 7.76 (s, 1H), 7.81 (d, 1H). Mass (M+H): 254.2

Example 17

5-((trans)-2-aminocyclopropyl)-N-(4-methylbenzyl)pyridin-2-amine hydrochloride

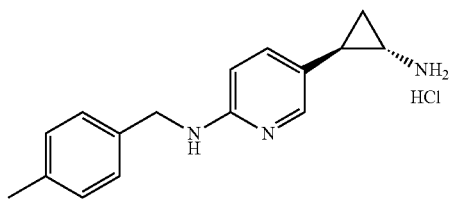 [SMILES: Cc1ccc(CNc2ccc([C@H]3C[C@@H]3N)cn2)cc1 ; Cl]

¹H-NMR (400 MHz, CD3OD) δ: 1.38 (q, 1H); 1.43 (quin, 1H), 2.33 (s, 3H), 2.38 (m, 1H), 2.91 (m, 1H), 4.53 (s, 2H) 7.06 (d, 1H), 7.20 (d, 2H), 7.26 (d, 2H), 7.76 (s, 1H), 7.78 (d, 1H). Mass (M+H): 254.2

Example 18

3-((5-((trans)-2-aminocyclopropyl)pyridin-2-ylamino)methyl)benzonitrile hydrochloride

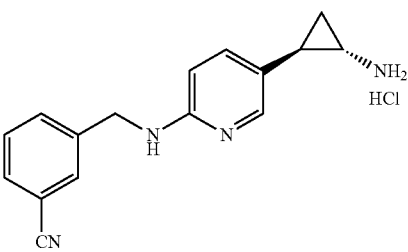 [SMILES: N#Cc1cccc(CNc2ccc([C@H]3C[C@@H]3N)cn2)c1 ; Cl]

¹H-NMR (400 MHz, D₂O) δ: 1.41 (q, 1H); 1.53 (quin, 1H), 2.47 (m, 1H), 2.96 (m, 1H), 4.74 (s, 2H), 7.06 (d, 1H), 7.63 (t, 1H), 7.75 (s, 2H), 7.78-7.85 (m, 3H). Mass (M+H): 265.2

Example 19

4-((5-((trans)-2-aminocyclopropyl)pyridin-2-ylamino)methyl)benzonitrile hydrochloride

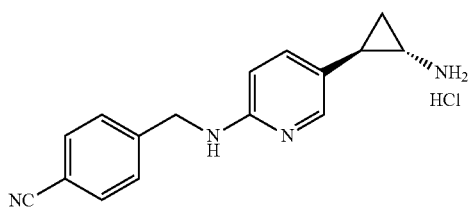 [SMILES: N#Cc1ccc(CNc2ccc([C@H]3C[C@@H]3N)cn2)cc1 ; Cl]

¹H-NMR (400 MHz, DMSO-d6) δ: 1.18 (q, 1H); 1.31 (quin, 1H), 2.24 (m, 1H), 2.78 (m, 1H), 4.68 (s, 2H), 6.85 (br, 1H), 7.54 (d, 3H), 7.82 (d, 3H), 8.35 (s, 3H). Mass (M+H): 265.2

Example 20

5-((trans)-2-aminocyclopropyl)-N-(3-methoxybenzyl)pyridin-2-amine hydrochloride

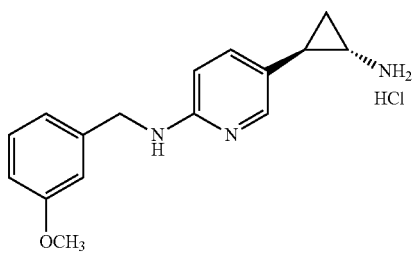 [SMILES: COc1cccc(CNc2ccc([C@H]3C[C@@H]3N)cn2)c1 ; Cl]

¹H-NMR (400 MHz, DMSO-d6) δ: 1.22 (q, 1H); 1.39 (quin, 1H), 2.33 (m, 1H), 2.81 (m, 1H), 3.74 (s, 3H), 4.61 (s, 2H), 6.88 (d, 1H), 6.95 (d, 1H), 7.01 (s, 1H), 7.06 (m, 1H), 7.31 (t, 1H), 7.76 (d, 1H), 7.86 (s, 1H), 8.58 (br, 3H), 9.12 (br, 1H). Mass (M+H): 270.2

Example 21

5-((trans)-2-aminocyclopropyl)-N-(4-methoxybenzyl)pyridin-2-amine hydrochloride

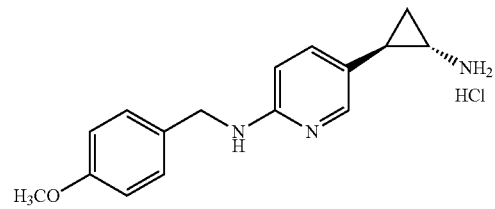 [SMILES: COc1ccc(CNc2ccc([C@H]3C[C@@H]3N)cn2)cc1 ; Cl]

¹H-NMR (400 MHz, DMSO-d6) δ: 1.22 (q, 1H); 1.38 (quin, 1H), 2.32 (m, 1H), 2.80 (m, 1H), 3.74 (s, 3H), 4.55 (s, 2H), 6.93 (d, 2H), 7.03 (s, 1H), 7.06 (m, 1H), 7.33 (d, 2H), 7.73 (d, 1H), 7.85 (s, 1H), 8.59 (s, 3H), 9.02 (br, 1H). Mass (M+H): 270.2

The following compounds can be synthesized following the method described in Scheme 1.

Example 22

4-(5-((trans)-2-aminocyclopropyl)pyridin-2-ylamino)phenol hydrochloride

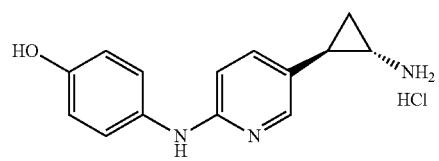 [SMILES: N[C@H]1C[C@@H]1c1ccc(Nc2ccc(O)cc2)nc1 ; Cl]

Example 23

3-((5-((trans)-2-aminocyclopropyl)pyridin-2-ylamino)methyl)benzamide hydrochloride

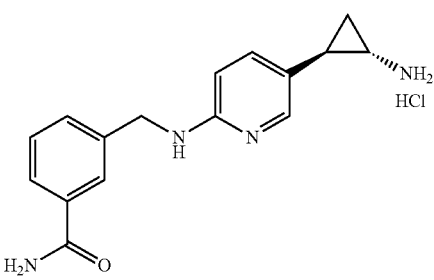 [SMILES: NC(=O)c1cccc(CNc2ccc([C@H]3C[C@@H]3N)cn2)c1 ; Cl]

Example 24

4-((5-((trans)-2-aminocyclopropyl)pyridin-2-ylamino)methyl)benzamide hydrochloride

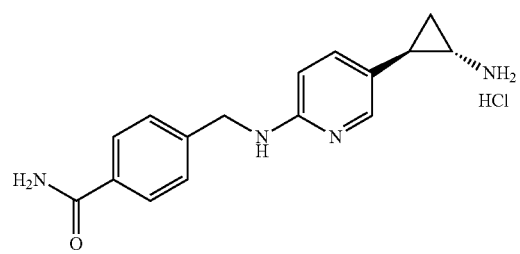 [SMILES: NC(=O)c1ccc(CNc2ccc([C@H]3C[C@@H]3N)cn2)cc1 ; Cl]

Example 25

4-((5-((trans)-2-aminocyclopropyl)pyridin-2-ylamino)methyl)phenol hydrochloride

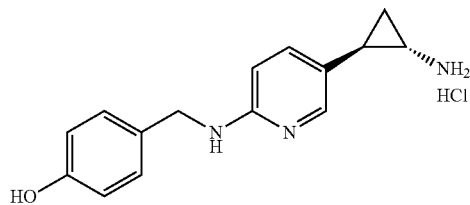

Example 26

5-((trans)-2-aminocyclopropyl)-N-(3-ethynylphenyl)pyridin-2-amine (or a hydrochloride salt thereof)

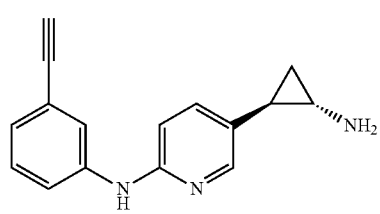 [SMILES: C#Cc1cccc(Nc2ccc([C@H]3C[C@@H]3N)cn2)c1]

Example 27

N-(5-((trans)-2-aminocyclopropyl)pyridin-2-yl)-1H-indol-7-amine (or a hydrochloride salt thereof)

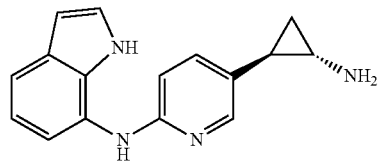 [SMILES: N[C@H]1C[C@@H]1c1ccc(Nc2cccc3cc[nH]c23)nc1]

Example 28

N-(5-((trans)-2-aminocyclopropyl)pyridin-2-yl)-1H-indazol-7-amine (or a hydrochloride salt thereof)

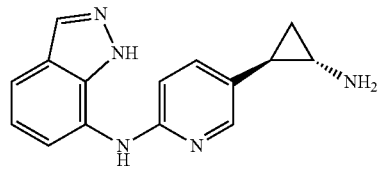 [SMILES: N[C@H]1C[C@@H]1c1ccc(Nc2cccc3cn[nH]c23)nc1]

Example 29

3-(5-((trans)-2-aminocyclopropyl)pyridin-2-ylamino)phenol (or a hydrochloride salt thereof)

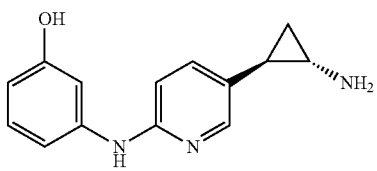 [SMILES: N[C@H]1C[C@@H]1c1ccc(Nc2cccc(O)c2)nc1]

Example 30

4-((trans)-2-aminocyclopropyl)-N-(4-methylbenzyl)aniline hydrochloride

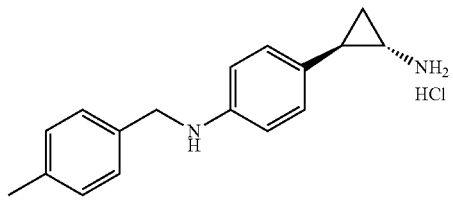 [SMILES: Cc1ccc(CNc2ccc([C@H]3C[C@@H]3N)cc2)cc1 ; Cl]

Example 31

4-((trans)-2-aminocyclopropyl)-N-(4-(trifluoromethyl)benzyl)aniline hydrochloride

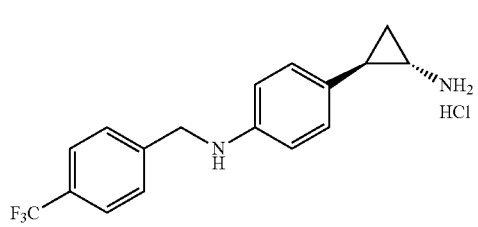 [SMILES: N[C@H]1C[C@@H]1c1ccc(NCc2ccc(C(F)(F)F)cc2)cc1 ; Cl]

Example 32

4-((trans)-2-aminocyclopropyl)-N-(3-chlorobenzyl)aniline hydrochloride

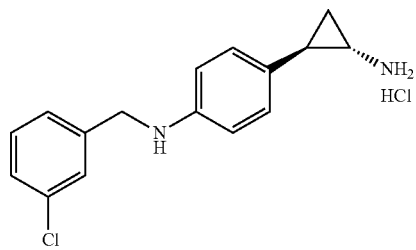 [SMILES: N[C@H]1C[C@@H]1c1ccc(NCc2cccc(Cl)c2)cc1 ; Cl]

Example 33

3-(((4-((trans)-2-aminocyclopropyl)phenyl)amino)methyl)benzonitrile hydrochloride

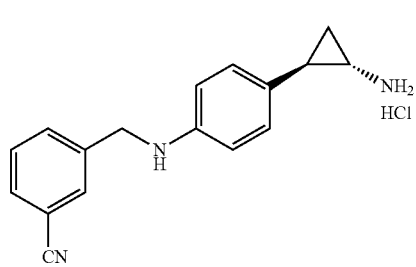 [SMILES: N#Cc1cccc(CNc2ccc([C@H]3C[C@@H]3N)cc2)c1 ; Cl]

Example 34

4-((trans)-2-aminocyclopropyl)-N-(p-tolyl)aniline hydrochloride

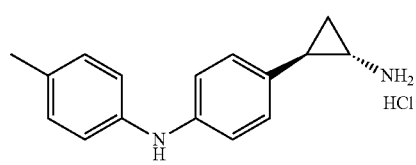 [SMILES: Cc1ccc(Nc2ccc([C@H]3C[C@@H]3N)cc2)cc1 ; Cl]

Example 35

4-((trans)-2-aminocyclopropyl)-N-(4-chlorophenyl)aniline hydrochloride

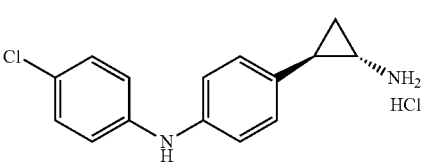 [SMILES: N[C@H]1C[C@@H]1c1ccc(Nc2ccc(Cl)cc2)cc1 ; Cl]

Example 36

3-((4-((trans)-2-aminocyclopropyl)phenyl)amino)benzonitrile hydrochloride

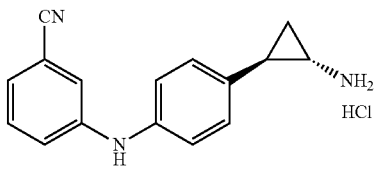 [SMILES: N#Cc1cccc(Nc2ccc([C@H]3C[C@@H]3N)cc2)c1 ; Cl]

Example 37

N-(4-((trans)-2-aminocyclopropyl)phenyl)-3-methoxyaniline hydrochloride

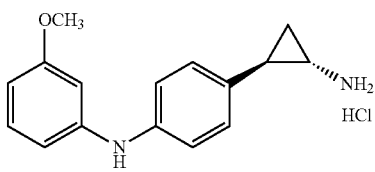 [SMILES: COc1cccc(Nc2ccc([C@H]3C[C@@H]3N)cc2)c1 ; Cl]

Example 38

3-((4-((trans)-2-aminocyclopropyl)phenyl)amino)benzamide hydrochloride

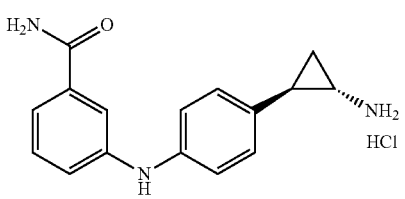 [SMILES: NC(=O)c1cccc(Nc2ccc([C@H]3C[C@@H]3N)cc2)c1 ; Cl]

Example 39

Biological Assays—Inhibition of LSD1

The compounds of the invention can be tested for their ability to inhibit LSD1. The ability of the compounds of the invention to inhibit LSD1 can be tested as follows. Human recombinant LSD1 protein was purchased from BPS Bioscience Inc. In order to monitor LSD1 enzymatic activity and/or its inhibition rate by our inhibitor(s) of interest, dimethylated H3-K4 peptide (Millipore) was chosen as a substrate. The demethylase activity was estimated, under aerobic conditions, by measuring the release of $H_2O_2$ produced during the catalytic process, using the Amplex® Red peroxide/peroxidase-coupled assay kit (Invitrogen).

Briefly, a fixed amount of LSD1 was incubated on ice for 15 minutes, in the absence and/or in the presence of various concentrations of inhibitor (e.g., from 0 to 75 μM, depending on the inhibitor strength). Tranylcypromine (Biomol International) was used as a control for inhibition. Within the experiment, each concentration of inhibitor was tested in triplicate. After leaving the enzyme interacting with the inhibitor, 12.5 μM of di-methylated H3-K4 peptide was added to each reaction and the experiment was left for 1 hour at 37° C. in the dark. The enzymatic reactions were set up in a 50 mM sodium phosphate, pH 7.4 buffer. At the end of the incubation, Amplex® Red reagent and horseradish peroxidase (HPR) solution were added to the reaction according to the recommendations provided by the supplier (Invitrogen), and left to incubate for 30 extra minutes at room temperature in the dark. A 1 μM $H_2O_2$ solution was used as a control of the kit efficiency. The conversion of the Amplex® Red reagent to resorufin due to the presence of $H_2O_2$ in the assay, was monitored by fluorescence (excitation at 540 nm, emission at 590 nm) using a microplate reader (Infinite 200, Tecan). Arbitrary units were used to measure level of $H_2O_2$ produced in the absence and/or in the presence of inhibitor.

The maximum demethylase activity of LSD1 was obtained in the absence of inhibitor and corrected for background fluorescence in the absence of LSD1. The Ki (IC50) of each inhibitor was estimated at half of the maximum activity.

The results presented in Table 1 below show the results of the LSD1 inhibition studies for a number of the Example compounds. Parnate (tranylcypromine; i.e., 2-trans phenylcyclopropylamine) was found to have a Ki of from about 15 to 35 micromolar depending on the enzyme preparation. The studies show that the compounds of the invention have unexpectedly potent LSD1 inhibition.

Example 40

Biological Assays—Monoamine Oxidase Assays for determining the selectivity of the compounds of the invention for LSD1

Human recombinant monoamine oxidase proteins MAO-A and MAO-B were purchased from Sigma Aldrich. MAOs catalyze the oxidative deamination of primary, secondary and tertiary amines. In order to monitor MAO enzymatic activities and/or their inhibition rate by inhibitor(s) of interest, a fluorescence-based (inhibitor)-screening assay was set up. 3-(2-Aminophenyl)-3-oxopropanamine (kynuramine dihydrobromide, Sigma Aldrich), a non fluorescent compound was chosen as a substrate. Kynuramine is a non-specific substrate for both MAO-A and MAO-B activities. While undergoing oxidative deamination by MAO activities, kynuramine is converted into 4-hydroxyquinoline (4-HQ), a resulting fluorescent product.

The monoamine oxidase activity was estimated by measuring the conversion of kynuramine into 4-hydroxyquinoline. Assays were conducted in 96-well black plates with clear bottom (Corning) in a final volume of 100 μL. The assay buffer was 100 mM HEPES, pH 7.5. Each experiment was performed in triplicate within the same experiment.

Briefly, a fixed amount of MAO (0.25 μg for MAO-A and 0.5 μg for MAO-B) was incubated on ice for 15 minutes in the reaction buffer, in the absence and/or in the presence of various concentrations of inhibitor (e.g., from 0 to 50 μM, depending on the inhibitor strength). Tranylcypromine (Biomol International) was used as a control for inhibition.

After leaving the enzyme(s) interacting with the inhibitor, 60 to 90 μM of kynuramine was added to each reaction for MAO-B and MAO-A assay respectively, and the reaction was left for 1 hour at 37° C. in the dark. The oxidative deamination of the substrate was stopped by adding 50 μL (v/v) of NaOH 2N. The conversion of kynuramine to 4-hydroxyquinoline, was monitored by fluorescence (excitation at 320 nm, emission at 360 nm) using a microplate reader (Infinite 200, Tecan). Arbitrary units were used to measure levels of fluorescence produced in the absence and/or in the presence of inhibitor.

The maximum of oxidative deamination activity was obtained by measuring the amount of 4-hydroxyquinoline formed from kynuramine deamination in the absence of inhibitor and corrected for background fluorescence in the absence of MAO enzymes. The Ki (IC50) of each inhibitor was determined at Vmax/2.

TABLE 1

Summary of Data from MAO-A, MAO-B, and LSD1 Inhibition Studies (Examples 39 and 41)

| Example No. | MAO-A (Ki) | MAO-B (Ki) | LSD1 (Ki) |
| --- | --- | --- | --- |
| 1 | I | III | II |
| 2 | I | III | II |
| 3 | I | II | II |
| 4 | I | I | II |
| 5 | I | II | II |
| 6 | I | I | II |
| 7 | I | II | II |
| 9 | I | II | II |
| 10 | I | I | II |
| 12 | I | I | II |
| 15 | I | I | II |
| 16 | I | I | II |
| 17 | I | I | II |
| 18 | I | I | II |

The ranges for the Ki value reported in Table 1 are for MAO-A, MAO-B and LSD1: I=between 1 μM and 40 μM; II=between 0.1 μM and 1 μM; III=between 0.001 μM and 0.1 μM.

Generally compounds of the Examples were found to have particularly low Ki (IC50) values for MAO-B and LSD1, as compared to MAO-A. For some of the compounds of the Examples, Ki (IC50) values for LSD1 were lower than 0.5 μM.

Some compounds of the Examples have been tested for antiproliferative/cytotoxic activity and been found to have activity in the micromolar to low micromolar range against cancer cell lines including HCT-116.

Previous reports of LSD1 have found that it is involved in cell proliferation and growth. Some studies have implicated LSD1 as a therapeutic target for cancer. Huang et al. (2007) *PNAS* 104:8023-8028 found that polyamine inhibitors of LSD1 modestly cause the reexpression of genes aberrantly silenced in cancer cells and particularly colorectal cancer (Huang et al. *Clin Cancer Res*. (2009) December 1; 15(23): 7217-28. Epub Nov. 24, 2009. PMID: 19934284). Scoumanne et al. ((2007) *J. Biol. Chem*. May 25; 282(21):15471-5) found that deficiency in LSD1 leads to a partial cell cycle arrest in G2/M and sensitizes cells to growth suppression induced by DNA damage. Kahl et al. ((2006) *Cancer Res*. 66(23):11341-7.) found that LSD1 expression is correlated with prostate cancer aggressiveness. Metzger et al. reported that LSD1 modulation by siRNA and pargyline regulates androgen receptor (AR) and may have therapeutic potential in cancers where AR plays a role, like prostate, testis, and brain cancers. Lee et al. ((2006) *Chem. Biol*. 13:563-567) reported that tranylcypromine derepresses Egr-1 gene expression in some cancer lines. A body of evidence is accumulating that Egr-1 is a tumor suppressor gene in many contexts (see e.g., Calogero et al. (2004) *Cancer Cell International* 4:1 exogenous expression of EGR-1 resulted in growth arrest and eventual cell death in primary cancer cell lines; Lucerna et al. (2006) *Cancer Research* 66, 6708-6713 show that sustained expression of Egr-1 causes antiangiogenic effects and inhibits tumor growth in some models; Ferraro et al. ((2005) *J. Clin. Oncol.* March 20; 23(9):1921-6) reported that Egr-1 is down-regulated in lung cancer patients with a higher risk of recurrence and may be more resistant to therapy. Thus, increasing Egr-1 expression via inhibition of LSD1 is a therapeutic approach for some cancers. Recent studies have also implicated LSD1 in brain cancer (Schulte et al. (2009) *Cancer Res.* March 1; 69(5):2065-71). Other studies have implicated LSD1 in breast cancer (Lims et al. Carcinogenesis. Dec. 30, 2009. [Epub ahead of print] PMID: 20042638).

Thus, a body of evidence has implicated LSD1 in a number of cancers, which suggests that LSD1 is a therapeutic target for cancer. The instant inventors have discovered a class of LSD1 inhibitors that can be used to treat diseases where LSD1 is implicated as a therapeutic target like cancer. Accordingly, the compounds of the invention can be used to treat such diseases.

Recent studies have also implicated LSD1 in viral infection and reactivation. In particular it was shown that pharmacological inhibitors of LSD1 like parnate and siRNA knock down of LSD1 caused reduced viral infectivity and reduced reactivation after latency (Liang et al. (2009) *Nat. Med.* 15:1312-1317). Therefore it is believed that the compounds of the invention can be used for treating or preventing viral infection. Furthermore, it is believed that the compounds of the invention can treat or prevent viral reactivation after latency.

Thus, without being bound by theory, the inventors have identified a new class of cyclylcyclopropylamine containing LSD1 inhibitors with unexpected potency for LSD1, a biologically relevant target in oncology and other diseases.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be obvious that certain changes and modifications may be practiced within the scope of the appended claims.

The invention claimed is:
1. A compound of Formula (I):

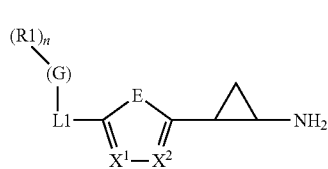

(I)

wherein;
E is —$X^3$=$X^4$—;
one of $X^1$, $X^2$, $X^3$, and $X^4$ is N and the other ones of $X^1$, $X^2$, $X^3$, and $X^4$ are each independently C(R2);
L1 is —NH—CH$_2$—;
G is phenyl, indolyl, or indazolyl;

each R1 is independently chosen from alkyl, alkenyl, alkynyl, cyclyl, -L2 cyclyl, -L2-amino, -L2-hydroxyl, amino, amide, nitro, halo, haloalkyl, haloalkoxy, cyano, sulfinyl, sulfonyl, sulfonamide, hydroxyl, alkoxy, urea, carbamate, acyl, and carboxyl;
each R2 is —H;
each L2 is independently chosen from alkylene and heteroalkylehe; and
n is 0, 1, 2, 3, 4 or 5;
or a pharmaceutically acceptable salt or solvate thereof.

2. The compound of claim 1, wherein G is phenyl.
3. The compound of claim 1, wherein $X^1$ is N, and $X^2$, $X^3$ and $X^4$ are each independently C(R2).
4. The compound of claim 1, wherein each R1 is independently chosen from lower alkyl, lower alkynyl, amido, halo, lower haloalkyl, cyano, hydroxyl, and alkoxy.
5. The compound of claim 1, wherein n is 0 or 1.
6. The compound of claim 1, wherein the compound of Formula (I) is in the trans configuration in respect of the substituents on the cyclopropyl ring.
7. The compound of claim 1, wherein said compound is chosen from:
   5-((trans)-2-aminocyclopropyl)-N-(3-chlorobenzyl)pyridin-2-amine;
   5-((trans)-2-amninocyclopropyl)-N-(4-chlorobenzyl)pyridin-2-amine;
   5-((trans)-2-aminocyclopropyl)-N-(3-(trifluoromethyl) benzyl)pyridin-2-amine;
   5-((trans)-2-aminocyclopropyl)-N-(4-(trifluoromethyl) benzyl)pyridin-2-amine;
   5-((trans)-2-aminocyclopropyl)-N-(3-methylbenzyl)pyridin-2-amine;
   5-((trans)-2-aminocyclopropyl)-N-(4-methylbenzyl)pyridin-2-amine;
   3-((5((trans)-2-aminocyclopropyl)pyridin-2-ylamino)methyl)benzonitrile;
   4((5-(trans)-2-aminocyclopropyl)pyridin-2-ylamino)methyl)benzonitrile;
   5-((trans)-2-aminocyclopropyl)-N-(3-methoxybenzyl)pyridin-2-amine;
   5-((trans)-2-aminocyclopropyl)-N-(4-methoxybenzyl)pyridin-2-amine;
   3-((5(trans)-2-aminocyclopropyl)pyridin-2-ylamino)methyl)benzamide;
   4-((5(trans)-2-aminocyclopropyl)pyridin-2-ylamino)methyl)benzamide;
   4-((5(trans)-2-aminocyclopropyl)pyridin-2-ylamino)methyl)phenol;
   or pharmaceutically acceptable salts or solvates thereof.
8. A pharmaceutical composition comprising the compound of claim 1 and a pharmaceutically acceptable carrier.
9. A compound of Formula (I):

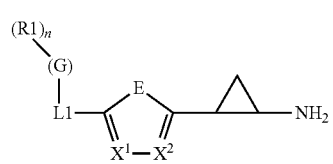

(I)

wherein:
E is —$X^3$=$X^4$—;
one of $X^1$, $X^2$, $X^3$, and $X^4$ is N and the other ones of $X^1$, $X^2$, $X^3$, and $X^4$ are each independently C(R2);
L1 is —NH— or —NH—CH$_2$—;

G is phenyl, indolyl, or indazolyl;
each R1 is independently chosen from alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, and carboxyl;
each R2 is —H;
each L2 is independently chosen from alkylene and heteroalkylene; and
n is 0, 1, 2, 3, 4 or 5;
or a pharmaceutically acceptable salt or solvate thereof.

10. The compound of claim 9, wherein $X^1$ is N, and $X^2$, $X^3$ and $X^4$ are each independently C(R2).

11. The compound of claim 9, wherein each R1 is independently chosen from lower alkyl, lower alkynyl, amido, halo, lower haloalkyl, cyano, hydroxyl, and alkoxy.

12. The compound of claim 9, wherein n is 0 or 1.

13. The compound of claim 9, wherein the compound of Formula (I) is in the trans configuration in respect of the substituents on the cyclopropyl ring.

14. The compound of claim 9, wherein said compound is chosen from:
5-((trans)-2-aminocyclopropyl)-N-(3-chlorophenyl)pyridin-2-amine;
5-((trans)-2-amninocyclopropyl)-N-(4-chlorophenyl)pyridin-2-amine;
5-((trans)-2-aminocyclopropyl)-N-(4-(trifluoromethyl)phenyl)pyridin-2-amine:
5-((trans)-2-aminocyclopropyl)-N-(3-methoxyphenyl)pyridin-2-amine;
5-((trans)-2-aminocyclopropyl)-N-(4-methoxyphenyl)pyridin-2-amine;
5-((trans)-2-aminocyclopropyl)-N-p-tolylpyridin-2-amine;
5-((trans)-2-aminocyclopropyl)-N-m-tolylpyridin-2-amine;
4-(5-((trans)-2-aminocyclopropyl)pyridin-2-ylamino)benzonitrile;
3-(5-((trans)-2-aminocyclopropyl)pyridin-2-ylamino)benzonitrile;
3-(5-((trans)-2-aminocyclopropyl)pyridin-2-ylamino)benzamide;
4-(5-((trans)-2-aminocyclopropyl)pyridin-2-ylamino)benzamide;
5-((trans)-2-aminocyclopropyl)-N-(3-chlorobenzyl)pyridin-2-amine;
5-((trans)-2-aminocyclopropyl)-N-(4-chlorobenzyl)pyridin-2-amine;
5-((trans)-2-aminocyclopropyl)-N-(3-(trifluoromethyl)benzyl)pyridin-2-amine;
5-((trans)-2-amninocyclopropyl)-N-(4-(trifluoromethyl)benzyl)pyridin-2-amine;
5-((trans)-2-aminocyclopropyl)-N-(3-methylbenzyl)pyridin-2-amine;
5-((trans)-2-aminocyclopropyl)-N-(4-methylbenzyl)pyridin-2-amine;
3-((5-((trans)-2-aminocyclopropyl)pyridin-2-ylamino)methyl)benzonitrile;
4-((5-((trans)-2-aminocyclopropyl)pyridin-2-ylamino)methyl)benzonitrile;
5-((trans)-2-aminocyclopropyl)-N-(3-methoxybenzyl)pyridin-2-amine;
5-((trans)-2-aminocyclopropyl)-N-(4-methoxybenzyl)pyridin-2-amine;
4-(5-((trans)-2-aminocyclopropyl)pyridin-2-ylamino)phenol;
3-((5-((trans)-2-aminocyclopropyl)pyridin-2-ylamino)methyl)benzamide;
4-((5-((trans)-2-aminocyclopropyi)pyridin-2-ylamino)methyl)benzamide,
4-((5-((trans)-2-aminocyclopropyl)pyridin-2-ylamino)methyl)phenol;
5-((trans)-2-aminocyclopropyl)-N-(3-ethynylphenyl)pyridin-2-amine;
N-(5-((trans)-2-aminocyclopropyl)pyridin-2-yl)-1H-indol-7-amine:
N-(5-((trans)-2-aminocyclopropyl)pyridin-2-yl)-1H-indazol-7-amine;
3-(5-((trans)-2-aminocyclopropyl)pyridin-2-ylamino)phenol;
or pharmaceutically acceptable salts or solvates thereof.

15. A pharmaceutical composition comprising the compound of claim 9 and a pharmaceutically acceptable carrier, 16. A compound of Formula (I):

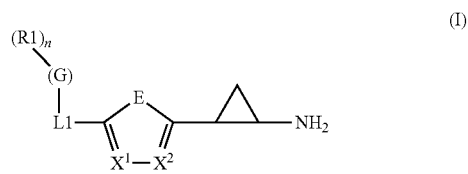

wherein:
E is —$X^3$=$X^4$—;
one of $X^1$, $X^2$, $X^3$, and $X^4$ is N or C(R2) and the other ones of $X^1$, $X^2$, $X^3$, and $X^4$ are each independently C(R2);
L1 is —NH— or —NH—$CH_2$—;
G is indolyl or indazolyl;
each R1 is independently chosen from alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, and carboxyl;
each R2 is —H;
each L2 is independently chosen from alkylene and heteroalkylene; and
n is 0, 1, 2, 3, 4 or 5;
or a pharmaceutically acceptable salt or solvate thereof.

17. The compound of claim 16, wherein one of $X^1$, $X^2$, $X^3$ and $X^4$ is N and the other ones of $X^1$, $X^2$, $X^3$ and $X^4$ are each independently C(R2).

18. The compound of claim 17, wherein $X^1$ is N, and $X^2$, $X^3$ and $X^4$ are each independently C(R2).

19. The compound of claim 16, wherein each R1 is independently chosen from lower alkyl, lower alkynyl, amido, halo, lower haloalkyl, cyano, hydroxyl, and alkoxy.

20. The compound of claim 16, wherein n is 0 or 1.

21. The compound of claim 16, wherein the compound of Formula (I) is in the trans configuration in respect of the substituents on the cyclopropyl ring.

22. A pharmaceutical composition comprising the compound of claim 16 and a pharmaceutically acceptable carrier.

* * * * *